(12) United States Patent
Green et al.

(10) Patent No.: US 6,429,303 B1
(45) Date of Patent: Aug. 6, 2002

(54) NUCLEIC ACIDS ENCODING MEMBERS OF THE HUMAN B LYMPHOCYTE ACTIVATION ANTIGEN B7 FAMILY AND METHODS OF USING THE SAME

(75) Inventors: Cynthia Green, Madison, CT (US); Victor Kotelianski, Boston, MA (US); Antonin de Fougerolles, Brookline, MA (US); John Carulli, Southborough, MA (US); Catherine Hession, Hingham, MA (US)

(73) Assignees: CuraGen Corporation, New Haven, CT (US); Biogen, Inc., Cambridge, MA (US)

( * ) Notice: Subject to any disclaimer, the term of this patent is extended or adjusted under 35 U.S.C. 154(b) by 0 days.

(21) Appl. No.: 09/651,200

(22) Filed: Aug. 30, 2000

Related U.S. Application Data

(60) Provisional application No. 60/152,383, filed on Sep. 3, 1999, provisional application No. 60/172,909, filed on Dec. 21, 1999, and provisional application No. 60/183,578, filed on Feb. 18, 2000.

(51) Int. Cl.[7] .................. C07H 21/04; C12N 15/09; C12N 15/63; A61K 48/00
(52) U.S. Cl. .................. 536/23.5; 536/23.1; 514/44; 435/69.1; 435/455; 435/320.1; 435/810
(58) Field of Search ............... 536/23.1, 23.5; 514/44; 435/69.1, 455, 370.1, 810

(56) References Cited

FOREIGN PATENT DOCUMENTS

| WO | WO 99/46281 | 9/1999 |
|----|-------------|--------|
| WO | WO 00/68266 | 11/2000 |

OTHER PUBLICATIONS

Chapoval et al. Nature Immunol. Mar. 2001; 2(3):269–274.*
Voet et al. In Biochemistry. John Wiley & Sons. 1990, vol. 1, pp. 126–128, and p. 230.*
Branch TIBS; 23:45–50.*
Mountain TIBTECH 18:119–128, 2000.*
Greenfield et al. Crit. Rev. Immunol. 1998; 18:389–418.*
Thompson Cell 1995; 81:979–982.*
Skolnick et al. Trends in Biotech., 18(1):34–39, 2000.*
Abbas et al. Nature Med. 1999; 5:1345–1346.*
Freeman, G. et al. (1991). *J. Exp. Med.* 174: 625–631. Abstract Only.
Nishimura, Y. et al. (2000). *Eur. J. Immunogen.* 27: 427–430.
Swallow, M. et al. (1999). *Immunity* 11: 423–432.
Zhang, D. and Johnson, R. (1997). *Cell Immunol.* 177: 9–17. Abstract Only.
Dong et al. (1999). *Nature Medicine* 5: 1365–1369.
Ling et al. (2000). *J. Immunol.* 1653–1657.
Linsley, P. S., et al. "Extending the B7 (CD80) gene family." *Protein Sci* 3(8): 1341–3 (1994).
Selvakumar, A., et al. "Genomic organization and chromosomal location of the human gene encoding the B–lymphocyte activation antigen B7." *Immunogenetics* 36(3): 175–81 (1992).
"Immunobiology—The Immune System in Health and Disease", Third edition, chapter 7, Janeway, C.A. et al., eds., Garland Publishing Inc., New York (1997), pp. 7:1–7:44.

* cited by examiner

*Primary Examiner*—Phillip Gambel
*Assistant Examiner*—Jessica H. Roark
(74) *Attorney, Agent, or Firm*—Mintz,Levin,Cohn,Ferris,Glovsky and Popeo, P.C.; Ivor R. Elrifi, Esq.; Christina V. Karnakis, Esq.

(57) ABSTRACT

An isolated BLAA polynucleotide and the membrane-associated or secreted polypeptide encoded by the BLAA polynucleotide are disclosed. Also disclosed are the antibodies that immunospecifically bind to a BLAA polypeptide or any derivative, variant, mutant or fragment of the BLAA polypeptide, polynucleotide or antibody. Also disclosed are nucleic acid vectors and host cells containing the nucleic acid sequence of the invention.

9 Claims, 13 Drawing Sheets

Translated Protein-Frame: 3-Nucleotide 111 to 1130
mz5004_vh.seq Length: 2691 24/Aug/1999

```
  1 GCGGCCGCGTGACCATCACGTGCTCCAGCTACCAGGGCTACCCTG
 46 AGGCTGAGGTGTTCTGGCAGGATGGGCAGGGTGTGCCCCTGACTG
 91 GCAACGTGACCACGTCGCAGATGGCCAACGAGCAGGGCTTGTTTG
    MetAlaAsnGluGlnGlyLeuPheA
136 ATGTGCACAGCATCCTGCGGGTGGTGCTGGGTGCAAATGGCACCT
    spValHisSerIleLeuArgValValLeuGlyAlaAsnGlyThrT
181 ACAGCTGCCTGGTGCGCAACCCCGTGCTGCAGCAGGATGCGCACA
    yrSerCysLeuValArgAsnProValLeuGlnGlnAspAlaHisS
226 GCTCTGTCACCATCACACCCCAGAGAAGCCCCACAGGAGCCGTGG
    erSerValThrIleThrProGlnArgSerProThrGlyAlaValG
271 AGGTCCAGGTCCCTGAGGACCCGGTGGTGGCCCTAGTGGGCACCG
    luValGlnValProGluAspProValValAlaLeuValGlyThrA
316 ATGCCACCCTGCACTGCTCCTTCTCCCCGAGCCTGGCTTCAGCC
    spAlaThrLeuHisCysSerPheSerProGluProGlyPheSerL
361 TGACACAGCTCAACCTCATCTGGCAGCTGACAGACACCAAACAGC
    euThrGlnLeuAsnLeuIleTrpGlnLeuThrAspThrLysGlnL
406 TGGTGCACAGTTTCACCGAAGGCCGGGACCAGGGCAGCGCCTATG
    euValHisSerPheThrGluGlyArgAspGlnGlySerAlaTyrA
451 CCAACCGCACGGCCCTCTTCCCGGACCTGCTGGCACAAGGCAATG
    laAsnArgThrAlaLeuPheProAspLeuLeuAlaGlnGlyAsnA
496 CATCCCTGAGGCTGCAGCGCGTGCGTGTGGCGGACGAGGGCAGCT
    laSerLeuArgLeuGlnArgValArgValAlaAspGluGlySerP
541 TCACCTGCTTCGTGAGCATCCGGGATTTCGGCAGCGCTGCCGTCA
    heThrCysPheValSerIleArgAspPheGlySerAlaAlaValS
586 GCCTGCAGGTGGCCGCTCCCTACTCGAAGCCCAGCATGACCCTGG
    erLeuGlnValAlaAlaProTyrSerLysProSerMetThrLeuG
631 AGCCCAACAAGGACCTGCGGCCAGGGGACACGGTGACCATCACGT
    luProAsnLysAspLeuArgProGlyAspThrValThrIleThrC
676 GCTCCAGCTACCGGGGCTACCCTGAGGCTGAGGTGTTCTGGCAGG
    ysSerSerTyrArgGlyTyrProGluAlaGluValPheTrpGlnA
721 ATGGGCAGGGTGTGCCCCTGACTGGCAACGTGACCACGTCGCAGA
    spGlyGlnGlyValProLeuThrGlyAsnValThrThrSerGlnM
766 TGGCCAACGAGCAGGGCTTGTTTGATGTGCACAGCGTCCTGCGGG
    etAlaAsnGluGlnGlyLeuPheAspValHisSerValLeuArgV
```

Fig. 1

```
 811 TGGTGCTGGGTGCGAATGGCACCTACAGCTGCCTGGTGCGCAACC
     alValLeuGlyAlaAsnGlyThrTyrSerCysLeuValArgAsnP

856 CCGTGCTGCAGCAGGATGCGCACGGCTCTGTCACCATCACAGGGC
     roValLeuGlnGlnAspAlaHisGlySerValThrIleThrGlyG

901 AGCCTATGACATTCCCCCCAGAGGCCCTGTGGGTGACCGTGGGGC
     lnProMetThrPheProProGluAlaLeuTrpValThrValGlyL

946 TCTCTGTCTGTCTCATTGCACTGCTGGTGGCCCTGGCTTTCGTGT
     euSerValCysLeuIleAlaLeuLeuValAlaLeuAlaPheValC

991 GCTGGAGAAAGATCAAACAGAGCTGTGAGGAGGAGAATGCAGGAG
     ysTrpArgLysIleLysGlnSerCysGluGluGluAsnAlaGlyA

1036 CCGAGGACCAGGATGGGGAGGGAGAAGGCTCCAAGACAGCCCTGC
     laGluAspGlnAspGlyGluGlyGluGlySerLysThrAlaLeuG

1081 AGCCTCTGAAACACTCTGACAGCAAAGAAGATGATGGACAAGAAA
     lnProLeuLysHisSerAspSerLysGluAspAspGlyGlnGluI

1126 TAGCCTGACCATGAGGACCAGGGAGCTGCTACCCCTCCCTACAGC
     leAla

1171 TCCTACCCTCTGGCTGCAATGGGGCTGCACTGTGAGCCCTGCCCC
1216 CAACAGATGCATCCTGCTCTGACAGGTGGGCTCCTTCTCCAAAGG
1261 ATGCGATACACAGACCACTGTGCAGCCTTATTTCTCCAATGGACA
1306 TGATTCCCAAGTCATCCTGCTGCCTTTTTTCTTATAGACACAATG
1351 AACAGACCACCCACAACCTTAGTTCTCTAAGTCATCCTGCCTGCT
1396 GCCTTATTTCACAGTACATACATTTCTTAGGGACACAGTACACTG
1441 ACCACATCACCACCCTCTTCTTCCAGTGCTGCGTGGACCATCTGG
1486 CTGCCTTTTTTCTCCAAAAGATGCAATATTCAGACTGACTGACCC
1531 CCTGCCTTATTTCACCAAAGACACGATGCATAGTCACCCCGGCCT
1576 TGTTTCTCCAATGGCCGTGATACACTAGTGATCATGTTCAGCCCT
1621 GCTTCCACCTGCATAGAATCTTTTCTTCTCAGACAGGGACAGTGC
1666 GGCCTCAACATCTCCTGGAGTCTAGAAGCTGTTTCCTTTCCCCTC
1711 CTTCCTCCTCTTGCTCTAGCCTTAATACTGGCCTTTTCCCTCCCT
1756 GCCCCAAGTGAAGACAGGGCACTCTGCGCCCACCACATGCACAGC
1801 TGTGCATGGAGACCTGCAGGTGCACGTGCTGGAACACGTGTGGTT
1846 CCCCCCTGGCCCAGCCTCCTCTGCAGTGCCCCTCTCCCTGCCCA
1891 TCCTCCCCACGGAAGCATGTGCTGGTCACACTGGTTCTCCAGGGG
1936 TCTGTGATGGGCCCCTGGGGGTCAGCTTCTGTCCCTCTGCCTTC
1981 TCACCTCTTTGTTCCTTTCTTTTCATGTATCCATTCAGTTGATGT
2026 TTATTGAGCAACTACAGATGTCAGCACTGTGTTAGGTGCTGGGGG
2071 CCCTGCGTGGGAAGATAAAGTTCCTCCCTCAAGGACTCCCCATCC
2116 AGCTGGGAGACAGACAACTAACTACACTGCACCCTGCGGTTTGCA
2161 GGGGGCTCCTGCCTGGCTCCCTGCTCCACACCTCCTCTGTGGCTC
2206 AAGGCTTCCTGGATACCTCACCCCCATCCCACCCATAATTCTTAC
2251 CCAGAGCATGGGGTTGGGGCGGAAACCTGGAGAGAGGGACATAGC
2296 CCCTCGCCACGGCTAGAGAATCTGGTGGTGTCCAAAATGTCTGTC
2341 CAGGTGTGGGCAGGTGGGCAGGCACCAAGGCCCTCTGGACCTTTC
2386 ATAGCAGCAGAAAAGGCAGAGCCTGGGGCAGGGCAGGGCCAGGAA
2431 TGCTTTGGGGACACCGAGGGGACTGCCCCCCACCCCCACCATGGT
2476 GCTATTCTGGGGCTGGGGCAGTCTTTTCCTGGCTTGCCTCTGGCC
2521 AGCTCCCGGCCTCTGGTAGAGTGAGACTTCAGACGTTCTGATGCC
```

Fig. 1 Continued

```
2566  TTCCGGATGTCATCTCTCCCTGCCCCAGGAATGGAAGATGTGAGG
2611  ACTTCTAATTTAAATGTGGGACTCGGAGGGATTTTGTAAACTGGG
2656  GGTATATTTTGGGGAAAATAAATGTCTTTGTAAAAA
```

Fig. 1 Continued

Translated Protein-Frame: 2-Nucleotide 2 to 1324
Mz5004 12/16/99

1
CCCTCTTCCCGGACCTGCTGGCACAGGGCAACGCATCCCTGAGGC
ProLeuProGlyProAlaGlyThrGlyGlnArgIleProGluAl

46
TGCAGCGCGTGCGTGTAGCGGACGAGGGCAGCTTCACCTGCTTCG
aAlaAlaArgAlaCysSerGlyArgGlyGlnLeuHisLeuLeuAr

91
TGAGCATCCGGGATTTCGGCAGCGCTGCCGTCAGCCTGCAGGTGG
gGluHisProGlyPheArgGlnArgCysArgGlnProAlaGlyGl

136
CCGCTCCCTACTCGAAGCCCAGCATGACCCTGGAGCCCAACAAGG
yArgSerLeuLeuGluAlaGlnHisAspProGlyAlaGlnGlnGl

181
ACCTGCGGCCAGGGGACACGGTGTGACCATCACGTGCTCCAGCTA
yProAlaAlaArgGlyHisGlyValThrIleThrCysSerSerTy

226
CCAGGGCTACCCTGAGGCTGAGGTGTTCTGGCAGGATGGGCAGGG
rGlnGlyTyrProGluAlaGluValPheTrpGlnAspGlyGlnGl

271
TGTGCCCCTGACTGGCAACGTGACCACGTCGCAGATGGCCAACGA
yValProLeuThrGlyAsnValThrThrSerGlnMetAlaAsnGl

316
GCAGGGCTTGTTTGATGTGCACAGCATCCTGCGGGTGGTGCTGGG
uGlnGlyLeuPheAspValHisSerIleLeuArgValValLeuGl

361
TGCAAATGGCACCTACAGCTGCCTGGTGCGCAACCCCGTGCTGCA
yAlaAsnGlyThrTyrSerCysLeuValArgAsnProValLeuGl

406
GCAGGATGCGCACAGCTCTGTCACCATCACACCCCAGAGAAGCCC
nGlnAspAlaHisSerSerValThrIleThrProGlnArgSerPr

451
CACAGGAGCCGTGGAGGTCCAGGTCCCTGAGGACCCGGTGGTGGC
oThrGlyAlaValGluValGlnValProGluAspProValValAl

496
CCTAGTGGGCACCGATGCCACCCTGCACTGCTCCTTCTCCCCCGA
aLeuValGlyThrAspAlaThrLeuHisCysSerPheSerProGl

541
GCCTGGCTTCAGCCTGACACAGCTCAACCTCATCTGGCAGCTGAC
uProGlyPheSerLeuThrGlnLeuAsnLeuIleTrpGlnLeuTh

586
AGACACCAAACAGCTGGTGCACAGTTTCACCGAAGGCCGGGACCA
rAspThrLysGlnLeuValHisSerPheThrGluGlyArgAspGl

631
GGGCAGCGCCTATGCCAACCGCACGGCCCTCTTCCCGGACCTGCT
nGlySerAlaTyrAlaAsnArgThrAlaLeuPheProAspLeuLe

676
GGCACAAGGCAATGCATCCCTGAGGCTGCAGCGCGTGCGTGTGGC
uAlaGlnGlyAsnAlaSerLeuArgLeuGlnArgValArgValAl

721
GGACGAGGGCAGCTTCACCTGCTTCGTGAGCATCCGGGATTTCGG
aAspGluGlySerPheThrCysPheValSerIleArgAspPheGl

Fig. 2

766
CAGCGCTGCCGTCAGCCTGCAGGTGGCCGCTCCCTACTCGAAGCC
ySerAlaAlaValSerLeuGlnValAlaAlaProTyrSerLysPr

811
CAGCATGACCCTGGAGCCCAACAAGGACCTGCGGCCAGGGGACAC
oSerMetThrLeuGluProAsnLysAspLeuArgProGlyAspTh

856
GGTGACCATCACGTGCTCCAGCTACCGGGGCTACCCTGAGGCTGA
rValThrIleThrCysSerSerTyrArgGlyTyrProGluAlaGl

901
GGTGTTCTGGCAGGATGGGCAGGGTGTGCCCCTGACTGGCAACGT
uValPheTrpGlnAspGlyGlnGlyValProLeuThrGlyAsnVa

946
GACCACGTCGCAGATGGCCAACGAGCAGGGCTTGTTTGATGTGCA
lThrThrSerGlnMetAlaAsnGluGlnGlyLeuPheAspValHi

991
CAGCGTCCTGCGGGTGGTGCTGGGTGCGAATGGCACCTACAGCTG
sSerValLeuArgValValLeuGlyAlaAsnGlyThrTyrSerCy

1036
CCTGGTGCGCAACCCCGTGCTGCAGCAGGATGCGCACGGCTCTGT
sLeuValArgAsnProValLeuGlnGlnAspAlaHisGlySerVa

1081
CACCATCACAGGGCAGCCTATGACATTCCCCCCAGAGGCCCTGTG
lThrIleThrGlyGlnProMetThrPheProProGluAlaLeuTr

1126
GGTGACCGTGGGGCTCTCTGTCTGTCTCATTGCACTGCTGGTGGC
pValThrValGlyLeuSerValCysLeuIleAlaLeuLeuValAl

1171
CCTGGCTTTCGTGTGCTGGAGAAAGATCAAACAGAGCTGTGAGGA
aLeuAlaPheValCysTrpArgLysIleLysGlnSerCysGluGl

1216
GGAGAATGCAGGAGCCGAGGACCAGGATGGGGAGGGAGAAGGCTC
uGluAsnAlaGlyAlaGluAspGlnAspGlyGluGlyGluGlySe

1261
CAAGACAGCCCTGCAGCCTCTGAAACACTCTGACAGCAAAGAAGA
rLysThrAlaLeuGlnProLeuLysHisSerAspSerLysGluAs

1306
TGATGGACAAGAAATAGCCTGACCATGAGGACCAGGGAGCTGCTA
pAspGlyGlnGluIleAla

1351
CCCCTCCCTACAGCTCCTACCCTCTGGCTGCAATGGGGCTGCACT

1396
GTGAGCCCTGCCCCCAACAGATGCATCCTGCTCTGACAGGTGGGC

1441
TCCTTCTCCAAAGGATGCGATACACAGACCACTGTGCAGCCTTAT

1486
TTCTCCAATGGACATGATTCCCAAGTCATCCTGCTGCCTTTTTTC

1531
TTATAGACACAATGAACAGACCACCCACAACCTTAGTTCTCTAAG

1576
TCATCCTGCCTGCTGCCTTATTTCACAGTACATACATTTCTTAGG

1621
GACACAGTACACTGACCACATCACCACCCTCTTCTTCCAGTGCTG

1666
CGTGGACCATCTGGCTGCCTTTTTTCTCCAAAAGATGCAATATTC

Fig. 2 Continued

```
1711 AGACTGACTGACCCCCTGCCTTATTTCACCAAAGACACGATGCAT
1756 AGTCACCCCGGCCTTGTTTCTCCAATGGCCGTGATACACTAGTGA
1801 TCATGTTCAGCCCTGCTTCCACCTGCATAGAATCTTTTCTTCTCA
1846 GACAGGGACAGTGCGGCCTCAACATCTCCTGGAGTCTAGAAGCTG
1891 TTTCCTTTCCCCTCCTTCCTCCTCTTGCTCTAGCCTTAATACTGG
1936 CCTTTTCCCTCCCTGCCCCAAGTGAAGACAGGGCACTCTGCGCCC
1981 ACCACATGCACAGCTGTGCATGGAGACCTGCAGGTGCACGTGCTG
2026 GAACACGTGTGGTTCCCCCCTGGCCCAGCCTCCTCTGCAGTGCCC
2071 CTCTCCCCTGCCCATCCTCCCCACGGAAGCATGTGCTGGTCACAC
2116 TGGTTCTCCAGGGGTCTGTGATGGGGCCCCTGGGGGTCAGCTTCT
2161 GTCCCTCTGCCTTCTCACCTCTTTGTTCCTTTCTTTTCATGTATC
2206 CATTCAGTTGATGTTTATTGAGCAACTACAGATGTCAGCACTGTG
2251 TTAGGTGCTGGGGCCCTGCGTGGGAAGATAAAGTTCCTCCCTCA
2296 AGGACTCCCCATCCAGCTGGGAGACAGACAACTAACTACACTGCA
2341 CCCTGCGGTTTGCAGGGGGCTCCTGCCTGGCTCCCTGCTCCACAC
2386 CTCCTCTGTGGCTCAAGGCTTCCTGGATACCTCACCCCCATCCCA
2431 CCCATAATTCTTACCCAGAGCATGGGGTTGGGGCGGAAACCTGGA
2476 GAGAGGGACATAGCCCCTCGCCACGGCTAGAGAATCTGGTGGTGT
2521 CCAAAATGTCTGTCCAGGTGTGGGCAGGTGGGCAGGCACCAAGGC
2566 CCTCTGGACCTTTCATAGCAGCAGAAAAGGCAGAGCCTGGGGCAG
2611 GGCAGGGCCAGGAATGCTTTGGGGACACCGAGGGGACTGCCCCCC
2656 ACCCCCACCATGGTGCTATTCTGGGGCTGGGGCAGTCTTTTCCTG
2701 GCTTGCCTCTGGCCAGCTCCCGGCCTCTGGTAGAGTGAGACTTCA
2746 GACGTTCTGATGCCTTCCGGATGTCATCTCTCCCTGCCCCAGGAA
2791 TGGAAGATGTGAGGACTTCTAATTTAAATGTGGGACTCGGAGGGA
2836 TTTTGTAAACTGGGGGTATATTTTGGGGAAAATAAATGTCTTTGT
2881 AAAAA
```

Fig. 2 Continued

Translated Protein 534 aa-Frame: 3-Nucleotide 60 to 1661
2/14/00

```
  1
     GCGGCCGCGGGGCAGCCTTCCACCACGGGGAGCCCAGCTGTCAGC
 46
     CGCCTCACAGGAAGATGCTGCGTCGGCGGGGCAGCCCTGGCATGG
                    MetLeuArgArgArgGlySerProGlyMetG
 91
     GTGTGCATGTGGGTGCAGCCCTGGGAGCACTGTGGTTCTGCCTCA
     lyValHisValGlyAlaAlaLeuGlyAlaLeuTrpPheCysLeuT
136
     CAGGAGCCCTGGAGGTCCAGGTCCCTGAAGACCCAGTGGTGGCAC
     hrGlyAlaLeuGluValGlnValProGluAspProValValAlaL
181
     TGGTGGGCACCGATGCCACCCTGTGCTGCTCCTTCTCCCCTGAGC
     euValGlyThrAspAlaThrLeuCysCysSerPheSerProGluP
226
     CTGGCTTCAGCCTGGCACAGCTCAACCTCATCTGGCAGCTGACAG
     roGlyPheSerLeuAlaGlnLeuAsnLeuIleTrpGlnLeuThrA
271
     ATACCAAACAGCTGGTGCACAGCTTTGCTGAGGGCCAGGACCAGG
     spThrLysGlnLeuValHisSerPheAlaGluGlyGlnAspGlnG
316
     GCAGCGCCTATGCCAACCGCACGGCCCTCTTCCCGGACCTGCTGG
     lySerAlaTyrAlaAsnArgThrAlaLeuPheProAspLeuLeuA
361
     CACAGGGCAACGCATCCCTGAGGCTGCAGCGCGTGCGTGTGGCGG
     laGlnGlyAsnAlaSerLeuArgLeuGlnArgValArgValAlaA
406
     ACGAGGGCAGCTTCACCTGCTTCGTGAGCATCCGGGATTTCGGCA
     spGluGlySerPheThrCysPheValSerIleArgAspPheGlyS
451
     GCGCTGCCGTCAGCCTGCAGGTGGCCGCTCCCTACTCGAAGCCCA
     erAlaAlaValSerLeuGlnValAlaAlaProTyrSerLysProS
496
     GCATGACCCTGGAGCCCAACAAGGACCTGCGGCCAGGGGACACGG
     erMetThrLeuGluProAsnLysAspLeuArgProGlyAspThrV
541
     TGACCATCACGTGCTCCAGCTACCAGGGCTACCCTGAGGCTGAGG
     alThrIleThrCysSerSerTyrGlnGlyTyrProGluAlaGluV
586
     TGTTCTGGCAGGATGGGCAGGGTGTGCCCCTGACTGGCAACGTGA
     alPheTrpGlnAspGlyGlnGlyValProLeuThrGlyAsnValT
631
     CCACGTCGCAGATGGCCAACGAGCAGGGCTTGTTTGATGTGCACA
     hrThrSerGlnMetAlaAsnGluGlnGlyLeuPheAspValHisS
676
     GCATCCTGCGGGTGGTGCTGGGTGCAAATGGCACCTACAGCTGCC
     erIleLeuArgValValLeuGlyAlaAsnGlyThrTyrSerCysL
721
     TGGTGCGCAACCCCGTGCTGCAGCAGGATGCGCACAGCTCTGTCA
     euValArgAsnProValLeuGlnGlnAspAlaHisSerSerValT
```

Fig. 3

```
766  CCATCACACCCCAGAGAAGCCCCACAGGAGCCGTGGAGGTCCAGG
     hrIleThrProGlnArgSerProThrGlyAlaValGluValGlnV
811  TCCCTGAGGACCCGGTGGTGGCCCTAGTGGGCACCGATGCCACCC
     alProGluAspProValValAlaLeuValGlyThrAspAlaThrL
856  TGCGCTGCTCCTTCTCCCCGAGCCTGGCTTCAGCCTGGCACAGC
     euArgCysSerPheSerProGluProGlyPheSerLeuAlaGlnL
901  TCAACCTCATCTGGCAGCTGACAGACACCAAACAGCTGGTGCACA
     euAsnLeuIleTrpGlnLeuThrAspThrLysGlnLeuValHisS
946  GTTTCACCGAAGGCCGGGACCAGGGCAGCGCCTATGCCAACCGCA
     erPheThrGluGlyArgAspGlnGlySerAlaTyrAlaAsnArgT
991  CGGCCCTCTTCCCGGACCTGCTGGCACAAGGCAATGCATCCCTGA
     hrAlaLeuPheProAspLeuLeuAlaGlnGlyAsnAlaSerLeuA
1036 GGCTGCAGCGCGTGCGTGTGGCGGACGAGGGCAGCTTCACCTGCT
     rgLeuGlnArgValArgValAlaAspGluGlySerPheThrCysP
1081 TCGTGAGCATCCGGGATTTCGGCAGCGCTGCCGTCAGCCTGCAGG
     heValSerIleArgAspPheGlySerAlaAlaValSerLeuGlnV
1126 TGGCCGCTCCCTACTCGAAGCCCAGCATGACCCTGGAGCCCAACA
     alAlaAlaProTyrSerLysProSerMetThrLeuGluProAsnL
1171 AGGACCTGCGGCCAGGGGACACGGTGACCATCACGTGCTCCAGCT
     ysAspLeuArgProGlyAspThrValThrIleThrCysSerSerT
1216 ACCGGGGCTACCCTGAGGCTGAGGTGTTCTGGCAGGATGGGCAGG
     yrArgGlyTyrProGluAlaGluValPheTrpGlnAspGlyGlnG
1261 GTGTGCCCCTGACTGGCAACGTGACCACGTCGCAGATGGCCAACG
     lyValProLeuThrGlyAsnValThrThrSerGlnMetAlaAsnG
1306 AGCAGGGCTTGTTTGATGTGCACAGCGTCCTGCGGGTGGTGCTGG
     luGlnGlyLeuPheAspValHisSerValLeuArgValValLeuG
1351 GTGCGAATGGCACCTACAGCTGCCTGGTGCGCAACCCCGTGCTGC
     lyAlaAsnGlyThrTyrSerCysLeuValArgAsnProValLeuG
1396 AGCAGGATGCGCACGGCTCTGTCACCATCACAGGGCAGCCTATGA
     lnGlnAspAlaHisGlySerValThrIleThrGlyGlnProMetT
1441 CATTCCCCCCAGAGGCCCTGTGGGTGACCGTGGGGCTGTCTGTCT
     hrPheProProGluAlaLeuTrpValThrValGlyLeuSerValC
1486 GTCTCATTGCACTGCTGGTGGCCCTGGCTTTCGTGTGCTGGAGAA
     ysLeuIleAlaLeuLeuValAlaLeuAlaPheValCysTrpArgL
1531 AGATCAAACAGAGCTGTGAGGAGGAGAATGCAGGAGCTGAGGACC
     ysIleLysGlnSerCysGluGluGluAsnAlaGlyAlaGluAspG
1576 AGGATGGGGAGGGAGAAGGCTCCAAGACAGCCCTGCAGCCTCTGA
     lnAspGlyGluGlyGluGlySerLysThrAlaLeuGlnProLeuL
```

Fig. 3 Continued

```
1621 AACACTCTGACAGCAAAGAAGATGATGGACAAGAAATAGCCTGAC
     ysHisSerAspSerLysGluAspAspGlyGlnGluIleAla
1666 CATGAGGACCAGGGAGCTGCTACCCCTCCCTACAGCTCCTACCCT
1711 CTGGCTGCAATGGGGCTGCACTGTGAGCCCTGCCCCAACAGATG
1756 CATCCTGCTCTGACAGGTGGGCTCCTTCTCCAAAGGATGCGATAC
1801 ACAGACCACTGTGCAGCCTTATTTCTCCAATGGACATGATTCCCA
1846 AGTCATCCTGCTGCCTTTTTTCTTATAGACACAATGAACAGACCA
1891 CCCACAACCTTAGTTCTCTAAGTCATCCTGCCTGCTGCCTTATTT
1936 CACAGTACATACATTTCTTAGGGACACAGTACACTGACCACATCA
1981 CCACCCTCTTCTTCCAGTGCTGCGTGGACCATCTGGCTGCCTTTT
2026 TTCTCCAAAAGATGCAATATTCAGACTGACTGACCCCCTGCCTTA
2071 TTTCACCAAAGACACGATGCATAGTCACCCCGACCTTGTTTCTCC
2116 AATGGCCGTGATACACTAGTGATCATGTTCAGCCCTGCTTCCACC
2161 TGCATAGAATCTTTTCTTCTCAGACAGGGACAGTGCGGCCTCAAC
2206 ATCTCCTGGAGTCTAGGCGGCCGC
```

Fig. 3 Continued

Multible Alignment:

```
B7-1_HUMAN                --MGHTRRQGTSPSKCPYLNFFQLLVLAGLS--HFCSGVIHVTKEVKEVATLSCGHNVSV
Q28499_rhesus_B7-1        --MGHTRRQEISPSKCPYLKFFQLLVLAGLS--HFCSGVIHVTKEVKEVATLSCGHNVSV
B7-1_RABIT                --MGHTLRPGTPLPECLELKLCQLLVLAGLA---HFSSGISQMTKSVAEVATLSCGHNISI
U57755_cat_B7-1           --MGHAAKMKTPLLKHPYPKLFPDLLLASGS--YFCSGIIQMTKTVREVATLSCGQNMISI
B7_1_MOUSE                MACNCQLMQDTPLLGFPCPRLILLFVLLIRLSQVSSDVDEQLSKSVKDKVLLPCRYNSPH
AF157827_cat_B7-2         ---------MGICDSTMGISRTDLVVALS----LSGVSSMKSQAYFNKTECPCHITMSQ
aaf17297_dog_B7-2         ----------MYILCTMGESNHLFVVVLL----LYGMASMKSQAYFNKTGECPCHITNSQ
l76088_pig_B7-2           ----------MGISNHLFVVVLL----LSGAASLKSQAYFNETGECPCHITNSQ
u04343_hu_B7-2            ----------MGHTRKHFLVVLLVLL----LSGAAFLKSQAYFNETADECPCQIANSQ
P42082_mus_B7-2           --------MDPECTMGHAILGFVTVLL----LSDAVSVETQAYFNGTADLECPFTKAQ
aac52336_mus_B7-2_alt.spl ----------MGHAILGFVTVLL----LSDAVSVETQAYFNGTADLECPFTKAQ
mz5020.protein            ----MLRRRGSPGMGVHVGAALGANWFCLTGALEVQVPEDPVVALVGTDATLCCSFSPEP
Q99420q99420_put_hum_B7-3 ----MASFLAFLLLNFERTCLLLLQLLMPHSAQFSVLGPSGRIAMVGEDADLPCHLFPDM B7-1_HUMAN                E-EDAQTRIYQKEKEMVLTCGNSN---DMNPEYNNRTIFDITNN----LSIVILAL
Q28499_rhesus_B7-1        E-EDAQTRIYQKEKEMVLTCGNSN---DMNPEYNNRTIFDITNN----LSIVILAL
B7-1_RABIT                D-ETARSRIYQKDQQSVLSIDS---GQVE---VMPEYKNRMIFPDILNN----LSCMILAL
U57755_cat_B7-1           K-ELTEDRIYQKDDEAVLAVMS---GKVQ---VMPEYNNSRPTEVTIDN----HSTVQMAL
B7_1_MOUSE                E-DESEDRIYQKEDNVVLSVHA---GKLK---VMPEYKNRTLIAPNTT----ASNILGGL
AF157827_cat_B7-2         NISLSEEMVTFKQDQQKLVAYELCR---GKENPQNVIHKYGRTSFDKIN----VLREEN
aaf17297_dog_B7-2         NISLSEEMVLFKQDQQKLVAYECR---GKENPQNVIHKYGRTSFDKIN----VLREEN
l76088_pig_B7-2           NLSLSEEMVLFKQDQQKLVAYELCR---GKEPHNVASKYAGRTSFDQAT----VLREEN
u04343_hu_B7-2            NQSLSEEMVLFKQDQQNLVAYELCR---GKEKFDSVNYKYAGRTSFDSDS----VLREEN
P42082_mus_B7-2           NISLSEEMVLFKQDQQNLVAYELCR---GTEKLDSVNAKYLGRTSFDRKN----VLREEN
aac52336_mus_B7-2_alt.spl NISLSEEMVLFKQDQQNLVAYELCR---GTEKLDSVNAKYLGRTSFDRKN----VLREEN
mz5020.protein            GFSLAQLNLIWQLTDTKQLVHSFAEGQD----GSAVANRTALFPDLLAQGNASLRLQRV
Q99420q99420_put_hum_B7-3 S--AETELRVRVSSSLRQVNVNYADGREVEDRQSAPGGRTSILRDGITAGKAAFRIQNV B7-1_HUMAN                RPSDEGTYECVVLKYEKDAFKREHLAEVTLSVKADFPTPSISDFEIPPSN---IRRIICS
Q28499_rhesus_B7-1        RPSDEGTYECVVLKYEKDAFKREHLAEVMLSVKADFPTPSIDSEIPPSN---IRRIICS
B7-1_RABIT                RESDKGTYTCVMQKNENGSFRREHLTSVTLSHRADFPVPDMDIGHPDPN---IKRIFGS
U57755_cat_B7-1           REKSDAGKYTCIELQNIEKGSYKVKPLTSVMLIVRADFVPSITDLGNFPAN---IKRIMCL
B7_1_MOUSE                VESDRGIYSCVMQKNKSRGTYEVKPLAVMLSTRADFPNPSIESGNPSAD---TKRITCF
AF157827_cat_B7-2         QRRKDEGAYHCEFHYGPKGLVPMIQMSSDLSVTANFSQPEIVTSNRTENSG--HDNLTCS
aaf17297_dog_B7-2         QRRKDEGAYHCEFHHKGPKGLVPMIQMRSDLSVTANFSQPEIVTSNRTENSG--HDNLTCS
l76088_pig_B7-2           QRRKDEGSYQCEFHHKGPKELVPIDQMSSDLSVTANFSQPENLLTNHTENS--VIHNLTCS
u04343_hu_B7-2            QRKDEGLYQCIIHHHKPTEMIRIHQMSSDLSVTANFSQPEIVPISRITENV---IHNLTCS
P42082_mus_B7-2           QRKDMGSYDCFQQKKPPTLSIILQQTLTELSVIANFSPPEIELAQNVGTGNS--GINTCS
aac52336_mus_B7-2_alt.spl QRKDMGSYDCFQQKKPPTLSIILQQTLTELSVIANFSPPEIELAQNVGTGNS--GINTCS
mz5020.protein            RQADEGSWTCFVSIREFG-------SAAVSKVAPKSGSPEPNKILRPGDVTLTCS
Q99420q99420_put_hum_B7-3 TGSDKNYLCLVFDGGFY-----EKAAIVEKVAALGSDLHVEKGYKDGG---LH-LECR B7-1_HUMAN                NSGGYPEPHLSWLENGE--ELNAINTTVS--QDPETELYAVSSKLDFNMTTNH----SFMC
Q28499_rhesus_B7-1        NSGGYPEPHLSWLENGE--ELNAISTTVS--QDPETELYTVSSKLDFNTTTNH----SFMC
B7-1_RABIT                ASGGFPEPHLAWLKDGE--ELNAVNTTVD--QDLDTELYSSSELDFNPTNMH----SCVC
U57755_cat_B7-1           LSGGYPKPHLSWLENEE--ELNAINTIVS--QDPETELYTISSEEDFNTGTNH----SFVC
B7_1_MOUSE                ASGGFPKPRFSWLENGR--ELPGINTTVS--QDPESELYTISSQLDFNTTRNH----TIKC
AF157827_cat_B7-2         SIQGYPEPKMYFQLNFTENSSTKYDTVKKSQNNVIELYAVSISLPPSVPEAH--NVSVFC
aaf17297_dog_B7-2         SIQGYPEPKMYFPLVKTENSSTKYDTVKKSQNNVIELYAVSISLSESVPEAS--NVSVFC
l76088_pig_B7-2           SIGGPEPRMYLLNTKNSTTEHDADKKSQNNVIELYAVSIRVSLPIPPET--NVSVFC
u04343_hu_B7-2            SIHGYPEPKMSVLLRTKNSTIEYDGIVKQSDNVIELYDVSISLSVSFPDVTSNMCVFC
P42082_mus_B7-2           SKQGFPKPKMYFLITN--STNEYGDMQISODNVIELYSLSNSLSLSFPDGVWHMCVVC
aac52336_mus_B7-2_alt.spl SKQGFPKPKMYFLITN--STNEYGDMQISODNVIELYSLSNSLSLSFPDGVWHMCVVC
mz5020.protein            SYQGYPEAEVFWQDGQG---VPLTGNVTTSQMANEQGLFDVHSIRVVLGANG----VYSC
Q99420q99420_put_hum_B7-3 SSGWYPEPQIQWSNNKG----ENIPVEAPVVADGVGLYAVAASVIMRGSSGE---GVSC
```

```
B7-1_HUMAN                  ------------------------------------------------------
Q28499_rhesus_B7-1          ------------------------------------------------------
B7-1_RABIT                  ------------------------------------------------------
U57755_cat_B7_1             ------------------------------------------------------
B7-1_MOUSE                  ------------------------------------------------------
AF157827_cat_B7-2           ------------------------------------------------------
aaf17297_dog_B7-2           ------------------------------------------------------
176088-pig_B7-2             ------------------------------------------------------
u04343_hu_B7-2              ------------------------------------------------------
P42082_mus_B7_2             ------------------------------------------------------
aac52336_mus_B7-2_alt.spl   ------------------------------------------------------
mz5020.protein              GQPMTFPPEALWVTVGLSVCLIALLVALAFVCWRKIKQSCEEENAGAEDQDGEGEGSKTA
Q99420q99420_put_hum_B7-3   ------------------------------------------------------

B7-1_HUMAN                  ------------------
Q28499_rhesus_B7-1          ------------------
B7-1_RABIT                  ------------------
U57755_cat_B7_1             ------------------
B7-1_MOUSE                  ------------------
AF157827_cat_B7-2           ------------------
aaf17297_dog_B7-2           ------------------
176088-pig_B7-2             ------------------
u04343_hu_B7-2              ------------------
P42082_mus_B7_2             ------------------
aac52336_mus_B7-2_alt.spl   ------------------
mz5020.protein              LQPLKHSDSKEDDGQEIA
Q99420q99420_put_hum_B7-3   ------------------
```

Fig. 4 Continued

SEQUENCE LISTING

```
<160> NUMBER OF SEQ ID NOS: 25

<210> SEQ ID NO 1
<211> LENGTH: 2691
<212> TYPE: DNA
<213> ORGANISM: Homo sapiens
<220> FEATURE:
<221> NAME/KEY: CDS
<222> LOCATION: (111)..(1130)

<400> SEQUENCE: 1
gcggccgcgt gaccatcacg tgctccagct accagggcta ccctgaggct gaggtgttct          60
ggcaggatgg gcagggtgtg cccctgactg gcaacgtgac cacgtcgcag atg gcc          116
                                                          Met Ala
                                                          1 aac gag cag ggc ttg ttt gat gtg cac agc atc ctg cgg gtg gtg ctg          164
Asn Glu Gln Gly Leu Phe Asp Val His Ser Ile Leu Arg Val Val Leu
        5                  10                  15 ggt gca aat ggc acc tac agc tgc ctg gtg cgc aac ccc gtg ctg cag          212
Gly Ala Asn Gly Thr Tyr Ser Cys Leu Val Arg Asn Pro Val Leu Gln
 20                  25                  30 cag gat gcg cac agc tct gtc acc atc aca ccc cag aga agc ccc aca          260
Gln Asp Ala His Ser Ser Val Thr Ile Thr Pro Gln Arg Ser Pro Thr
 35                  40                  45                  50 gga gcc gtg gag gtc cag gtc cct gag gac ccg gtg gtg gcc cta gtg          308
Gly Ala Val Glu Val Gln Val Pro Glu Asp Pro Val Val Ala Leu Val
                 55                  60                  65 ggc acc gat gcc acc ctg cac tgc tcc ttc tcc ccc gag cct ggc ttc          356
Gly Thr Asp Ala Thr Leu His Cys Ser Phe Ser Pro Glu Pro Gly Phe
         70                  75                  80 agc ctg aca cag ctc aac ctc atc tgg cag ctg aca gac acc aaa cag          404
Ser Leu Thr Gln Leu Asn Leu Ile Trp Gln Leu Thr Asp Thr Lys Gln
     85                  90                  95 ctg gtg cac agt ttc acc gaa ggc cgg gac cag ggc agc gcc tat gcc          452
Leu Val His Ser Phe Thr Glu Gly Arg Asp Gln Gly Ser Ala Tyr Ala
 100                 105                 110 aac cgc acg gcc ctc ttc ccg gac ctg ctg gca caa ggc aat gca tcc          500
Asn Arg Thr Ala Leu Phe Pro Asp Leu Leu Ala Gln Gly Asn Ala Ser
115                 120                 125                 130 ctg agg ctg cag cgc gtg cgt gtg gcg gac gag ggc agc ttc acc tgc          548
Leu Arg Leu Gln Arg Val Arg Val Ala Asp Glu Gly Ser Phe Thr Cys
                135                 140                 145
```

-continued

| | |
|---|---|
| ttc gtg agc atc cgg gat ttc ggc agc gct gcc gtc agc ctg cag gtg<br>Phe Val Ser Ile Arg Asp Phe Gly Ser Ala Ala Val Ser Leu Gln Val<br>150                       155                    160 | 596 |
| gcc gct ccc tac tcg aag ccc agc atg acc ctg gag ccc aac aag gac<br>Ala Ala Pro Tyr Ser Lys Pro Ser Met Thr Leu Glu Pro Asn Lys Asp<br>     165                   170                      175 | 644 |
| ctg cgg cca ggg gac acg gtg acc atc acg tgc tcc agc tac cgg ggc<br>Leu Arg Pro Gly Asp Thr Val Thr Ile Thr Cys Ser Ser Tyr Arg Gly<br>180                       185                    190 | 692 |
| tac cct gag gct gag gtg ttc tgg cag gat ggg cag ggt gtg ccc ctg<br>Tyr Pro Glu Ala Glu Val Phe Trp Gln Asp Gly Gln Gly Val Pro Leu<br>195                       200                   205                210 | 740 |
| act ggc aac gtg acc acg tcg cag atg gcc aac gag cag ggc ttg ttt<br>Thr Gly Asn Val Thr Thr Ser Gln Met Ala Asn Glu Gln Gly Leu Phe<br>               215                    220                    225 | 788 |
| gat gtg cac agc gtc ctg cgg gtg gtg ctg ggt gcg aat ggc acc tac<br>Asp Val His Ser Val Leu Arg Val Val Leu Gly Ala Asn Gly Thr Tyr<br>230                       235                    240 | 836 |
| agc tgc ctg gtg cgc aac ccc gtg ctg cag cag gat gcg cac ggc tct<br>Ser Cys Leu Val Arg Asn Pro Val Leu Gln Gln Asp Ala His Gly Ser<br>245                       250                    255 | 884 |
| gtc acc atc aca ggg cag cct atg aca ttc ccc cca gag gcc ctg tgg<br>Val Thr Ile Thr Gly Gln Pro Met Thr Phe Pro Pro Glu Ala Leu Trp<br>260                       265                    270 | 932 |
| gtg acc gtg ggg ctc tct gtc tgt ctc att gca ctg ctg gtg gcc ctg<br>Val Thr Val Gly Leu Ser Val Cys Leu Ile Ala Leu Leu Val Ala Leu<br>275                       280                    285                290 | 980 |
| gct ttc gtg tgc tgg aga aag atc aaa cag agc tgt gag gag gag aat<br>Ala Phe Val Cys Trp Arg Lys Ile Lys Gln Ser Cys Glu Glu Glu Asn<br>               295                    300                    305 | 1028 |
| gca gga gcc gag gac cag gat ggg gag gga gaa ggc tcc aag aca gcc<br>Ala Gly Ala Glu Asp Gln Asp Gly Glu Gly Glu Gly Ser Lys Thr Ala<br>310                       315                    320 | 1076 |
| ctg cag cct ctg aaa cac tct gac agc aaa gaa gat gat gga caa gaa<br>Leu Gln Pro Leu Lys His Ser Asp Ser Lys Glu Asp Asp Gly Gln Glu<br>     325                   330                      335 | 1124 |
| ata gcc tgaccatgag gaccagggag ctgctacccc tccctacagc tcctaccctc<br>Ile Ala<br>    340 | 1180 |
| tggctgcaat ggggctgcac tgtgagccct gcccccaaca gatgcatcct gctctgacag | 1240 |
| gtgggctcct tctccaaagg atgcgataca cagaccactg tgcagcctta tttctccaat | 1300 |
| ggacatgatt cccaagtcat cctgctgcct ttttcttat agacacaatg aacagaccac | 1360 |
| ccacaacctt agttctctaa gtcatcctgc ctgctgcctt atttcacagt acatacattt | 1420 |
| cttagggaca cagtacactg accacatcac caccctcttc ttccagtgct gcgtggacca | 1480 |
| tctggctgcc ttttttctcc aaaagatgca atattcagac tgactgaccc cctgccttat | 1540 |
| ttcaccaaag acacgatgca tagtcacccc ggccttgttt ctccaatggc cgtgatacac | 1600 |
| tagtgatcat gttcagccct gcttccacct gcatagaatc ttttcttctc agacagggac | 1660 |
| agtgcggcct caacatctcc tggagtctag aagctgtttc ctttcccctc cttcctcctc | 1720 |
| ttgctctagc cttaatactg gccttttccc tccctgcccc aagtgaagac agggcactct | 1780 |
| gcgcccacca catgcacagc tgtgcatgga gacctgcagg tgcacgtgct ggaacacgtg | 1840 |
| tggttccccc ctggcccagc ctcctctgca gtgcccctct ccctgccca tcctccccac | 1900 |
| ggaagcatgt gctggtcaca ctggttctcc agggg tctgt gatgggcccc ctgggggtca | 1960 |
| gcttctgtcc ctctgccttc tcacctcttt gttcctttct tttcatgtat ccattcagtt | 2020 |

```
gatgtttatt gagcaactac agatgtcagc actgtgttag gtgctggggg ccctgcgtgg      2080
gaagataaag ttcctccctc aaggactccc catccagctg ggagacagac aactaactac      2140
actgcaccct gcggtttgca gggggctcct gcctggctcc ctgctccaca cctcctctgt      2200
ggctcaaggc ttcctggata cctcaccccc atcccaccca taattcttac ccagagcatg      2260
gggttggggc ggaaacctgg agagagggac atagcccctc gccacggcta gagaatctgg      2320
tggtgtccaa aatgtctgtc caggtgtggg caggtgggca ggcaccaagg ccctctggac      2380 cttttcatagc agcagaaaag gcagagcctg gggcagggca gggccaggaa tgctttgggg      2440
acaccgaggg gactgccccc caccccccacc atggtgctat tctgggctg gggcagtctt      2500 ttcctggctt gcctctggcc agctcccggc tctggtagag gtgagacttc agacgttctg      2560
atgccttccg gatgtcatct ctccctgccc caggaatgga agatgtgagg acttctaatt      2620
taaatgtggg actcggaggg attttgtaaa ctgggggtat attttgggga aaataaatgt      2680
ctttgtaaaa a                                                          2691
```

<210> SEQ ID NO 2
<211> LENGTH: 340
<212> TYPE: PRT
<213> ORGANISM: Homo sapiens

<400> SEQUENCE: 2

```
Met Ala Asn Glu Gln Gly Leu Phe Asp Val His Ser Ile Leu Arg Val
  1               5                  10                  15

Val Leu Gly Ala Asn Gly Thr Tyr Ser Cys Leu Val Arg Asn Pro Val
             20                  25                  30

Leu Gln Gln Asp Ala His Ser Ser Val Thr Ile Thr Pro Gln Arg Ser
         35                  40                  45

Pro Thr Gly Ala Val Glu Val Gln Val Pro Glu Asp Pro Val Val Ala
     50                  55                  60

Leu Val Gly Thr Asp Ala Thr Leu His Cys Ser Phe Ser Pro Glu Pro
 65                  70                  75                  80

Gly Phe Ser Leu Thr Gln Leu Asn Leu Ile Trp Gln Leu Thr Asp Thr
                 85                  90                  95

Lys Gln Leu Val His Ser Phe Thr Glu Gly Arg Asp Gln Gly Ser Ala
            100                 105                 110

Tyr Ala Asn Arg Thr Ala Leu Phe Pro Asp Leu Leu Ala Gln Gly Asn
        115                 120                 125

Ala Ser Leu Arg Leu Gln Arg Val Arg Val Ala Asp Glu Gly Ser Phe
    130                 135                 140

Thr Cys Phe Val Ser Ile Arg Asp Phe Gly Ser Ala Ala Val Ser Leu
145                 150                 155                 160

Gln Val Ala Ala Pro Tyr Ser Lys Pro Ser Met Thr Leu Glu Pro Asn
                165                 170                 175

Lys Asp Leu Arg Pro Gly Asp Thr Val Thr Ile Thr Cys Ser Ser Tyr
            180                 185                 190

Arg Gly Tyr Pro Glu Ala Glu Val Phe Trp Gln Asp Gly Gln Gly Val
        195                 200                 205

Pro Leu Thr Gly Asn Val Thr Thr Ser Gln Met Ala Asn Glu Gln Gly
    210                 215                 220

Leu Phe Asp Val His Ser Val Leu Arg Val Val Leu Gly Ala Asn Gly
225                 230                 235                 240

Thr Tyr Ser Cys Leu Val Arg Asn Pro Val Leu Gln Gln Asp Ala His
```

```
                    245                 250                 255
Gly Ser Val Thr Ile Thr Gly Gln Pro Met Thr Phe Pro Pro Glu Ala
                260                 265                 270

Leu Trp Val Thr Val Gly Leu Ser Val Cys Leu Ile Ala Leu Leu Val
            275                 280                 285

Ala Leu Ala Phe Val Cys Trp Arg Lys Ile Lys Gln Ser Cys Glu Glu
        290                 295                 300

Glu Asn Ala Gly Ala Glu Asp Gln Asp Gly Glu Gly Glu Gly Ser Lys
305                 310                 315                 320

Thr Ala Leu Gln Pro Leu Lys His Ser Asp Ser Lys Glu Asp Asp Gly
                325                 330                 335

Gln Glu Ile Ala
            340

<210> SEQ ID NO 3
<211> LENGTH: 2885
<212> TYPE: DNA
<213> ORGANISM: Homo sapiens
<220> FEATURE:
<221> NAME/KEY: CDS
<222> LOCATION: (2)..(1324)

<400> SEQUENCE: 3 c cct ctt ccc gga cct gct ggc aca ggg caa cgc atc cct gag gct gca      49
  Pro Leu Pro Gly Pro Ala Gly Thr Gly Gln Arg Ile Pro Glu Ala Ala
    1               5                  10                  15 gcg cgt gcg tgt agc gga cga ggg cag ctt cac ctg ctt cgt gag cat      97
Ala Arg Ala Cys Ser Gly Arg Gly Gln Leu His Leu Leu Arg Glu His
                20                  25                  30 ccg gga ttt cgg cag cgc tgc cgt cag cct gca ggt ggc cgc tcc cta     145
Pro Gly Phe Arg Gln Arg Cys Arg Gln Pro Ala Gly Gly Arg Ser Leu
            35                  40                  45 ctc gaa gcc cag cat gac cct gga gcc caa caa gga cct gcg gcc agg     193
Leu Glu Ala Gln His Asp Pro Gly Ala Gln Gln Gly Pro Ala Ala Arg
        50                  55                  60 gga cac ggt gtg acc atc acg tgc tcc agc tac cag ggc tac cct gag     241
Gly His Gly Val Thr Ile Thr Cys Ser Ser Tyr Gln Gly Tyr Pro Glu
65                  70                  75                  80 gct gag gtg ttc tgg cag gat ggg cag ggt gtg ccc ctg act ggc aac     289
Ala Glu Val Phe Trp Gln Asp Gly Gln Gly Val Pro Leu Thr Gly Asn
                85                  90                  95 gtg acc acg tcg cag atg gcc aac gag cag ggc ttg ttt gat gtg cac     337
Val Thr Thr Ser Gln Met Ala Asn Glu Gln Gly Leu Phe Asp Val His
            100                 105                 110 agc atc ctg cgg gtg gtg ctg ggt gca aat ggc acc tac agc tgc ctg     385
Ser Ile Leu Arg Val Val Leu Gly Ala Asn Gly Thr Tyr Ser Cys Leu
        115                 120                 125 gtg cgc aac ccc gtg ctg cag cag gat gcg cac agc tct gtc acc atc     433
Val Arg Asn Pro Val Leu Gln Gln Asp Ala His Ser Ser Val Thr Ile
    130                 135                 140 aca ccc cag aga agc ccc aca gga gcc gtg gag gtc cag gtc cct gag     481
Thr Pro Gln Arg Ser Pro Thr Gly Ala Val Glu Val Gln Val Pro Glu
145                 150                 155                 160 gac ccg gtg gtg gcc cta gtg ggc acc gat gcc acc ctg cac tgc tcc     529
Asp Pro Val Val Ala Leu Val Gly Thr Asp Ala Thr Leu His Cys Ser
                165                 170                 175 ttc tcc ccc gag cct ggc ttc agc ctg aca cag ctc aac ctc atc tgg     577
Phe Ser Pro Glu Pro Gly Phe Ser Leu Thr Gln Leu Asn Leu Ile Trp
            180                 185                 190
```

| | | |
|---|---|---|
| cag ctg aca gac acc aaa cag ctg gtg cac agt ttc acc gaa ggc cgg<br>Gln Leu Thr Asp Thr Lys Gln Leu Val His Ser Phe Thr Glu Gly Arg<br>           195                  200              205 | 625 |
| gac cag ggc agc gcc tat gcc aac cgc acg gcc ctc ttc ccg gac ctg<br>Asp Gln Gly Ser Ala Tyr Ala Asn Arg Thr Ala Leu Phe Pro Asp Leu<br>210               215                  220 | 673 |
| ctg gca caa ggc aat gca tcc ctg agg ctg cag cgc gtg cgt gtg gcg<br>Leu Ala Gln Gly Asn Ala Ser Leu Arg Leu Gln Arg Val Arg Val Ala<br>225               230                  235              240 | 721 |
| gac gag ggc agc ttc acc tgc ttc gtg agc atc cgg gat ttc ggc agc<br>Asp Glu Gly Ser Phe Thr Cys Phe Val Ser Ile Arg Asp Phe Gly Ser<br>           245                  250              255 | 769 |
| gct gcc gtc agc ctg cag gtg gcc gct ccc tac tcg aag ccc agc atg<br>Ala Ala Val Ser Leu Gln Val Ala Ala Pro Tyr Ser Lys Pro Ser Met<br>                 260                  265              270 | 817 |
| acc ctg gag ccc aac aag gac ctg cgg cca ggg gac acg gtg acc atc<br>Thr Leu Glu Pro Asn Lys Asp Leu Arg Pro Gly Asp Thr Val Thr Ile<br>           275                  280              285 | 865 |
| acg tgc tcc agc tac cgg ggc tac cct gag gct gag gtg ttc tgg cag<br>Thr Cys Ser Ser Tyr Arg Gly Tyr Pro Glu Ala Glu Val Phe Trp Gln<br>290               295                  300 | 913 |
| gat ggg cag ggt gtg ccc ctg act ggc aac gtg acc acg tcg cag atg<br>Asp Gly Gln Gly Val Pro Leu Thr Gly Asn Val Thr Thr Ser Gln Met<br>305               310                  315              320 | 961 |
| gcc aac gag cag ggc ttg ttt gat gtg cac agc gtc ctg cgg gtg gtg<br>Ala Asn Glu Gln Gly Leu Phe Asp Val His Ser Val Leu Arg Val Val<br>                 325                  330              335 | 1009 |
| ctg ggt gcg aat ggc acc tac agc tgc ctg gtg cgc aac ccc gtg ctg<br>Leu Gly Ala Asn Gly Thr Tyr Ser Cys Leu Val Arg Asn Pro Val Leu<br>           340                  345              350 | 1057 |
| cag cag gat gcg cac ggc tct gtc acc atc aca ggg cag cct atg aca<br>Gln Gln Asp Ala His Gly Ser Val Thr Ile Thr Gly Gln Pro Met Thr<br>355               360                  365 | 1105 |
| ttc ccc cca gag gcc ctg tgg gtg acc gtg ggg ctc tct gtc tgt ctc<br>Phe Pro Pro Glu Ala Leu Trp Val Thr Val Gly Leu Ser Val Cys Leu<br>370               375                  380 | 1153 |
| att gca ctg ctg gtg gcc ctg gct ttc gtg tgc tgg aga aag atc aaa<br>Ile Ala Leu Leu Val Ala Leu Ala Phe Val Cys Trp Arg Lys Ile Lys<br>385               390                  395              400 | 1201 |
| cag agc tgt gag gag gag aat gca gga gcc gag gac cag gat ggg gag<br>Gln Ser Cys Glu Glu Glu Asn Ala Gly Ala Glu Asp Gln Asp Gly Glu<br>                 405                  410              415 | 1249 |
| gga gaa ggc tcc aag aca gcc ctg cag cct ctg aaa cac tct gac agc<br>Gly Glu Gly Ser Lys Thr Ala Leu Gln Pro Leu Lys His Ser Asp Ser<br>           420                  425              430 | 1297 |
| aaa gaa gat gat gga caa gaa ata gcc tgaccatgag gaccagggag<br>Lys Glu Asp Asp Gly Gln Glu Ile Ala<br>           435                  440 | 1344 |
| ctgctacccc tccctacagc tcctaccctc tggctgcaat ggggctgcac tgtgagccct | 1404 |
| gcccccaaca gatgcatcct gctctgacag gtgggctcct tctccaaagg atgcgataca | 1464 |
| cagaccactg tgcagcctta tttctccaat ggacatgatt cccaagtcat cctgctgcct | 1524 |
| ttttcttat agacacaatg aacagaccac ccacaacctt agttctctaa gtcatcctgc | 1584 |
| ctgctgcctt atttcacagt acatacattt cttagggaca cagtacactg accacatcac | 1644 |
| caccctcttc ttccagtgct gcgtggacca tctggctgcc ttttttctcc aaaagatgca | 1704 |
| atattcagac tgactgaccc cctgcctat ttcaccaaag acacgatgca tagtcacccc | 1764 |
| ggccttgttt ctccaatggc cgtgatacac tagtgatcat gttcagccct gcttccacct | 1824 |

-continued

```
gcatagaatc tttcttctc agacagggac agtgcggcct caacatctcc tggagtctag    1884
aagctgtttc ctttcccctc cttcctcctc ttgctctagc cttaatactg gccttttccc    1944
tccctgcccc aagtgaagac agggcactct gcgcccacca catgcacagc tgtgcatgga    2004
gacctgcagg tgcacgtgct ggaacacgtg tggttccccc ctggcccagc ctcctctgca    2064
gtgcccctct cccctgccca tcctcccac ggaagcatgt gctggtcaca ctggttctcc     2124
aggggtctgt gatggggccc ctgggggtca gcttctgtcc ctctgccttc tcacctcttt    2184
gttcctttct tttcatgtat ccattcagtt gatgtttatt gagcaactac agatgtcagc    2244
actgtgttag gtgctggggg ccctgcgtgg aagataaag ttcctccctc aaggactccc     2304
catccagctg ggagacagac aactaactac actgcaccct gcggtttgca gggggctcct    2364
gcctggctcc ctgctccaca cctcctctgt ggctcaaggc ttcctggata cctcaccccc    2424
atcccaccca taattcttac ccagagcatg gggttgggc ggaaacctgg agagagggac     2484
atagcccctc gccacggcta gagaatctgg tggtgtccaa aatgtctgtc caggtgtggg    2544
caggtgggca ggcaccaagg ccctctggac ctttcatagc agcagaaaag gcagagcctg    2604
gggcagggca gggccaggaa tgctttgggg acaccgaggg gactgccccc caccccacc     2664 atggtgctat tctggggctg gggcagtctt ttcctggctt gcctctggcc agctcccggc    2724
ctctggtaga gtgagacttc agacgttctg atgccttccg gatgtcatct ctccctgccc    2784
caggaatgga agatgtgagg acttctaatt taaatgtggg actcggaggg attttgtaaa    2844
ctgggggtat attttgggga aaataaatgt ctttgtaaaa a                       2885
```

<210> SEQ ID NO 4
<211> LENGTH: 441
<212> TYPE: PRT
<213> ORGANISM: Homo sapiens

<400> SEQUENCE: 4

```
Pro Leu Pro Gly Pro Ala Gly Thr Gly Gln Arg Ile Pro Glu Ala Ala
  1               5                  10                  15

Ala Arg Ala Cys Ser Gly Arg Gly Gln Leu His Leu Arg Glu His
             20                  25                  30

Pro Gly Phe Arg Gln Arg Cys Arg Gln Pro Ala Gly Gly Arg Ser Leu
         35                  40                  45

Leu Glu Ala Gln His Asp Pro Gly Ala Gln Gly Pro Ala Ala Arg
     50                  55                  60

Gly His Gly Val Thr Ile Thr Cys Ser Ser Tyr Gln Gly Tyr Pro Glu
 65                  70                  75                  80

Ala Glu Val Phe Trp Gln Asp Gly Gln Gly Val Pro Leu Thr Gly Asn
                 85                  90                  95

Val Thr Thr Ser Gln Met Ala Asn Glu Gln Gly Leu Phe Asp Val His
            100                 105                 110

Ser Ile Leu Arg Val Val Leu Gly Ala Asn Gly Thr Tyr Ser Cys Leu
        115                 120                 125

Val Arg Asn Pro Val Leu Gln Gln Asp Ala His Ser Ser Val Thr Ile
    130                 135                 140

Thr Pro Gln Arg Ser Pro Thr Gly Ala Val Glu Val Gln Val Pro Glu
145                 150                 155                 160

Asp Pro Val Val Ala Leu Val Gly Thr Asp Ala Thr Leu His Cys Ser
                165                 170                 175

Phe Ser Pro Glu Pro Gly Phe Ser Leu Thr Gln Leu Asn Leu Ile Trp
```

-continued

```
                    180                 185                 190
Gln Leu Thr Asp Thr Lys Gln Leu Val His Ser Phe Thr Glu Gly Arg
            195                 200                 205
Asp Gln Gly Ser Ala Tyr Ala Asn Arg Thr Ala Leu Phe Pro Asp Leu
        210                 215                 220
Leu Ala Gln Gly Asn Ala Ser Leu Arg Leu Gln Arg Val Arg Val Ala
225                 230                 235                 240
Asp Glu Gly Ser Phe Thr Cys Phe Val Ser Ile Arg Asp Phe Gly Ser
                245                 250                 255
Ala Ala Val Ser Leu Gln Val Ala Ala Pro Tyr Ser Lys Pro Ser Met
            260                 265                 270
Thr Leu Glu Pro Asn Lys Asp Leu Arg Pro Gly Asp Thr Val Thr Ile
        275                 280                 285
Thr Cys Ser Ser Tyr Arg Gly Tyr Pro Glu Ala Glu Val Phe Trp Gln
    290                 295                 300
Asp Gly Gln Gly Val Pro Leu Thr Gly Asn Val Thr Thr Ser Gln Met
305                 310                 315                 320
Ala Asn Glu Gln Gly Leu Phe Asp Val His Ser Val Leu Arg Val Val
                325                 330                 335
Leu Gly Ala Asn Gly Thr Tyr Ser Cys Leu Val Arg Asn Pro Val Leu
            340                 345                 350
Gln Gln Asp Ala His Gly Ser Val Thr Ile Thr Gly Gln Pro Met Thr
        355                 360                 365
Phe Pro Pro Glu Ala Leu Trp Val Thr Val Gly Leu Ser Val Cys Leu
    370                 375                 380
Ile Ala Leu Leu Val Ala Leu Ala Phe Val Cys Trp Arg Lys Ile Lys
385                 390                 395                 400
Gln Ser Cys Glu Glu Glu Asn Ala Gly Ala Glu Asp Gln Asp Gly Glu
                405                 410                 415
Gly Glu Gly Ser Lys Thr Ala Leu Gln Pro Leu Lys His Ser Asp Ser
            420                 425                 430
Lys Glu Asp Asp Gly Gln Glu Ile Ala
        435                 440
```

<210> SEQ ID NO 5
<211> LENGTH: 2229
<212> TYPE: DNA
<213> ORGANISM: Homo sapiens
<220> FEATURE:
<221> NAME/KEY: CDS
<222> LOCATION: (60)..(1661)

<400> SEQUENCE: 5

```
gcggccgcgg ggcagccttc caccacgggg agcccagctg tcagccgcct cacaggaag        59 atg ctg cgt cgg cgg ggc agc cct ggc atg ggt gtg cat gtg ggt gca       107
Met Leu Arg Arg Arg Gly Ser Pro Gly Met Gly Val His Val Gly Ala
  1               5                  10                  15 gcc ctg gga gca ctg tgg ttc tgc ctc aca gga gcc ctg gag gtc cag       155
Ala Leu Gly Ala Leu Trp Phe Cys Leu Thr Gly Ala Leu Glu Val Gln
             20                  25                  30 gtc cct gaa gac cca gtg gtg gca ctg gtg ggc acc gat gcc acc ctg       203
Val Pro Glu Asp Pro Val Val Ala Leu Val Gly Thr Asp Ala Thr Leu
         35                  40                  45 tgc tgc tcc ttc tcc cct gag cct ggc ttc agc ctg gca cag ctc aac       251
Cys Cys Ser Phe Ser Pro Glu Pro Gly Phe Ser Leu Ala Gln Leu Asn
     50                  55                  60
```

```
ctc atc tgg cag ctg aca gat acc aaa cag ctg gtg cac agc ttt gct      299
Leu Ile Trp Gln Leu Thr Asp Thr Lys Gln Leu Val His Ser Phe Ala
 65                  70                  75                  80 gag ggc cag gac cag ggc agc gcc tat gcc aac cgc acg gcc ctc ttc      347
Glu Gly Gln Asp Gln Gly Ser Ala Tyr Ala Asn Arg Thr Ala Leu Phe
                 85                  90                  95 ccg gac ctg ctg gca cag ggc aac gca tcc ctg agg ctg cag cgc gtg      395
Pro Asp Leu Leu Ala Gln Gly Asn Ala Ser Leu Arg Leu Gln Arg Val
            100                 105                 110 cgt gtg gcg gac gag ggc agc ttc acc tgc ttc gtg agc atc cgg gat      443
Arg Val Ala Asp Glu Gly Ser Phe Thr Cys Phe Val Ser Ile Arg Asp
        115                 120                 125 ttc ggc agc gct gcc gtc agc ctg cag gtg gcc gct ccc tac tcg aag      491
Phe Gly Ser Ala Ala Val Ser Leu Gln Val Ala Ala Pro Tyr Ser Lys
    130                 135                 140 ccc agc atg acc ctg gag ccc aac aag gac ctg cgg cca ggg gac acg      539
Pro Ser Met Thr Leu Glu Pro Asn Lys Asp Leu Arg Pro Gly Asp Thr
145                 150                 155                 160 gtg acc atc acg tgc tcc agc tac cag ggc tac cct gag gct gag gtg      587
Val Thr Ile Thr Cys Ser Ser Tyr Gln Gly Tyr Pro Glu Ala Glu Val
                165                 170                 175 ttc tgg cag gat ggg cag ggt gtg ccc ctg act ggc aac gtg acc acg      635
Phe Trp Gln Asp Gly Gln Gly Val Pro Leu Thr Gly Asn Val Thr Thr
            180                 185                 190 tcg cag atg gcc aac gag cag ggc ttg ttt gat gtg cac agc atc ctg      683
Ser Gln Met Ala Asn Glu Gln Gly Leu Phe Asp Val His Ser Ile Leu
        195                 200                 205 cgg gtg gtg ctg ggt gca aat ggc acc tac agc tgc ctg gtg cgc aac      731
Arg Val Val Leu Gly Ala Asn Gly Thr Tyr Ser Cys Leu Val Arg Asn
    210                 215                 220 ccc gtg ctg cag cag gat gcg cac agc tct gtc acc atc aca ccc cag      779
Pro Val Leu Gln Gln Asp Ala His Ser Ser Val Thr Ile Thr Pro Gln
225                 230                 235                 240 aga agc ccc aca gga gcc gtg gag gtc cag gtc cct gag gac ccg gtg      827
Arg Ser Pro Thr Gly Ala Val Glu Val Gln Val Pro Glu Asp Pro Val
                245                 250                 255 gtg gcc cta gtg ggc acc gat gcc acc ctg cgc tgc tcc ttc tcc ccc      875
Val Ala Leu Val Gly Thr Asp Ala Thr Leu Arg Cys Ser Phe Ser Pro
            260                 265                 270 gag cct ggc ttc agc ctg gca cag ctc aac ctc atc tgg cag ctg aca      923
Glu Pro Gly Phe Ser Leu Ala Gln Leu Asn Leu Ile Trp Gln Leu Thr
        275                 280                 285 gac acc aaa cag ctg gtg cac agt ttc acc gaa ggc cgg gac cag ggc      971
Asp Thr Lys Gln Leu Val His Ser Phe Thr Glu Gly Arg Asp Gln Gly
    290                 295                 300 agc gcc tat gcc aac cgc acg gcc ctc ttc ccg gac ctg ctg gca caa     1019
Ser Ala Tyr Ala Asn Arg Thr Ala Leu Phe Pro Asp Leu Leu Ala Gln
305                 310                 315                 320 ggc aat gca tcc ctg agg ctg cag cgc gtg cgt gtg gcg gac gag ggc     1067
Gly Asn Ala Ser Leu Arg Leu Gln Arg Val Arg Val Ala Asp Glu Gly
                325                 330                 335 agc ttc acc tgc ttc gtg agc atc cgg gat ttc ggc agc gct gcc gtc     1115
Ser Phe Thr Cys Phe Val Ser Ile Arg Asp Phe Gly Ser Ala Ala Val
            340                 345                 350 agc ctg cag gtg gcc gct ccc tac tcg aag ccc agc atg acc ctg gag     1163
Ser Leu Gln Val Ala Ala Pro Tyr Ser Lys Pro Ser Met Thr Leu Glu
        355                 360                 365 ccc aac aag gac ctg cgg cca ggg gac acg gtg acc atc acg tgc tcc     1211
Pro Asn Lys Asp Leu Arg Pro Gly Asp Thr Val Thr Ile Thr Cys Ser
    370                 375                 380
```

```
agc tac cgg ggc tac cct gag gct gag gtg ttc tgg cag gat ggg cag      1259
Ser Tyr Arg Gly Tyr Pro Glu Ala Glu Val Phe Trp Gln Asp Gly Gln
385                 390                 395                 400 ggt gtg ccc ctg act ggc aac gtg acc acg tcg cag atg gcc aac gag      1307
Gly Val Pro Leu Thr Gly Asn Val Thr Thr Ser Gln Met Ala Asn Glu
            405                 410                 415 cag ggc ttg ttt gat gtg cac agc gtc ctg cgg gtg gtg ctg ggt gcg      1355
Gln Gly Leu Phe Asp Val His Ser Val Leu Arg Val Val Leu Gly Ala
        420                 425                 430 aat ggc acc tac agc tgc ctg gtg cgc aac ccc gtg ctg cag cag gat      1403
Asn Gly Thr Tyr Ser Cys Leu Val Arg Asn Pro Val Leu Gln Gln Asp
    435                 440                 445 gcg cac ggc tct gtc acc atc aca ggg cag cct atg aca ttc ccc cca      1451
Ala His Gly Ser Val Thr Ile Thr Gly Gln Pro Met Thr Phe Pro Pro
450                 455                 460 gag gcc ctg tgg gtg acc gtg ggg ctg tct gtc tgt ctc att gca ctg      1499
Glu Ala Leu Trp Val Thr Val Gly Leu Ser Val Cys Leu Ile Ala Leu
465                 470                 475                 480 ctg gtg gcc ctg gct ttc gtg tgc tgg aga aag atc aaa cag agc tgt      1547
Leu Val Ala Leu Ala Phe Val Cys Trp Arg Lys Ile Lys Gln Ser Cys
                485                 490                 495 gag gag gag aat gca gga gct gag gac cag gat ggg gag gga gaa ggc      1595
Glu Glu Glu Asn Ala Gly Ala Glu Asp Gln Asp Gly Glu Gly Glu Gly
            500                 505                 510 tcc aag aca gcc ctg cag cct ctg aaa cac tct gac agc aaa gaa gat      1643
Ser Lys Thr Ala Leu Gln Pro Leu Lys His Ser Asp Ser Lys Glu Asp
        515                 520                 525 gat gga caa gaa ata gcc tgaccatgag gaccagggag ctgctacccc             1691
Asp Gly Gln Glu Ile Ala
    530 tccctacagc tcctaccctc tggctgcaat ggggctgcac tgtgagccct gcccccaaca   1751 gatgcatcct gctctgacag gtgggctcct tctccaaagg atgcgataca cagaccactg   1811 tgcagcctta tttctccaat ggacatgatt cccaagtcat cctgctgcct tttttcttat   1871 agacacaatg aacagaccac ccacaacctt agttctctaa gtcatcctgc ctgctgcctt   1931 atttcacagt acatacattt cttagggaca cagtacactg accacatcac caccctcttc   1991 ttccagtgct gcgtggacca tctggctgcc ttttttctcc aaaagatgca atattcagac   2051 tgactgaccc cctgccttat ttcaccaaag acacgatgca tagtcacccc gaccttgttt   2111 ctccaatggc cgtgatacac tagtgatcat gttcagccct gcttccacct gcatagaatc   2171 ttttcttctc agacagggac agtgcggcct caacatctcc tggagtctag gcggccgc    2229

<210> SEQ ID NO 6
<211> LENGTH: 534
<212> TYPE: PRT
<213> ORGANISM: Homo sapiens

<400> SEQUENCE: 6

Met Leu Arg Arg Arg Gly Ser Pro Gly Met Gly Val His Val Gly Ala
 1               5                  10                  15

Ala Leu Gly Ala Leu Trp Phe Cys Leu Thr Gly Ala Leu Glu Val Gln
            20                  25                  30

Val Pro Glu Asp Pro Val Val Ala Leu Val Gly Thr Asp Ala Thr Leu
        35                  40                  45

Cys Cys Ser Phe Ser Pro Glu Pro Gly Phe Ser Leu Ala Gln Leu Asn
    50                  55                  60
```

-continued

```
Leu Ile Trp Gln Leu Thr Asp Thr Lys Gln Leu Val His Ser Phe Ala
 65                  70                  75                  80

Glu Gly Gln Asp Gln Gly Ser Ala Tyr Ala Asn Arg Thr Ala Leu Phe
                 85                  90                  95

Pro Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
        115                 120                 125

Phe Gly Ser Ala Ala Val Ser Leu Gln Val Ala Pro Tyr Ser Lys
    130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Gln Gly Tyr Pro Glu Ala Glu Val
                165                 170                 175

Phe Trp Gln Asp Gly Gln Gly Val Pro Leu Thr Gly Asn Val Thr Thr
            180                 185                 190

Ser Gln Met Ala Asn Glu Gln Gly Leu Phe Asp Val His Ser Ile Leu
        195                 200                 205

Arg Val Val Leu Gly Ala Asn Gly Thr Tyr Ser Cys Leu Val Arg Asn
    210                 215                 220

Pro Val Leu Gln Gln Asp Ala His Ser Ser Val Thr Ile Thr Pro Gln
225                 230                 235                 240

Arg Ser Pro Thr Gly Ala Val Glu Val Gln Val Pro Glu Asp Pro Val
                245                 250                 255

Val Ala Leu Val Gly Thr Asp Ala Thr Leu Arg Cys Ser Phe Ser Pro
            260                 265                 270

Glu Pro Gly Phe Ser Leu Ala Gln Leu Asn Leu Ile Trp Gln Leu Thr
        275                 280                 285

Asp Thr Lys Gln Leu Val His Ser Phe Thr Glu Gly Arg Asp Gln Gly
    290                 295                 300

Ser Ala Tyr Ala Asn Arg Thr Ala Leu Phe Pro Asp Leu Leu Ala Gln
305                 310                 315                 320

Gly Asn Ala Ser Leu Arg Leu Gln Arg Val Arg Val Ala Asp Glu Gly
                325                 330                 335

Ser Phe Thr Cys Phe Val Ser Ile Arg Asp Phe Gly Ser Ala Ala Val
            340                 345                 350

Ser Leu Gln Val Ala Ala Pro Tyr Ser Lys Pro Ser Met Thr Leu Glu
        355                 360                 365

Pro Asn Lys Asp Leu Arg Pro Gly Asp Thr Val Thr Ile Thr Cys Ser
    370                 375                 380

Ser Tyr Arg Gly Tyr Pro Glu Ala Glu Val Phe Trp Gln Asp Gly Gln
385                 390                 395                 400

Gly Val Pro Leu Thr Gly Asn Val Thr Thr Ser Gln Met Ala Asn Glu
                405                 410                 415

Gln Gly Leu Phe Asp Val His Ser Val Leu Arg Val Val Leu Gly Ala
            420                 425                 430

Asn Gly Thr Tyr Ser Cys Leu Val Arg Asn Pro Val Leu Gln Gln Asp
        435                 440                 445

Ala His Gly Ser Val Thr Ile Thr Gly Gln Pro Met Thr Phe Pro Pro
    450                 455                 460

Glu Ala Leu Trp Val Thr Val Gly Leu Ser Val Cys Leu Ile Ala Leu
465                 470                 475                 480

Leu Val Ala Leu Ala Phe Val Cys Trp Arg Lys Ile Lys Gln Ser Cys
```

|     |     |     | 485 |     |     |     |     | 490 |     |     |     |     | 495 |     |
| --- | --- | --- | --- | --- | --- | --- | --- | --- | --- | --- | --- | --- | --- | --- |
| Glu | Glu | Glu | Asn | Ala | Gly | Ala | Glu | Asp | Gln | Asp | Gly | Glu | Gly | Gly |
|     |     |     |     |     | 500 |     |     |     |     | 505 |     |     |     | 510 |
| Ser | Lys | Thr | Ala | Leu | Gln | Pro | Leu | Lys | His | Ser | Asp | Ser | Lys | Glu | Asp |
|     |     |     |     | 515 |     |     |     |     | 520 |     |     |     |     | 525 |
| Asp | Gly | Gln | Glu | Ile | Ala |
|     |     |     | 530 |

<210> SEQ ID NO 7
<211> LENGTH: 1020
<212> TYPE: DNA
<213> ORGANISM: Homo sapiens

<400> SEQUENCE: 7

```
atggccaacg agcagggctt gtttgatgtg cacagcatcc tgcgggtggt gctgggtgca      60
aatggcacct acagctgcct ggtgcgcaac cccgtgctgc agcaggatgc gcacagctct     120
gtcaccatca cccccagag aagccccaca ggagccgtgg aggtccaggt ccctgaggac     180
ccggtggtgg ccctagtggg caccgatgcc accctgcact gctccttctc ccccgagcct     240
ggcttcagcc tgacacagct caacctcatc tggcagctga cagacaccaa acagctggtg     300
cacagtttca ccgaaggccg ggaccagggc agcgcctatg ccaaccgcac ggccctcttc     360
ccggacctgc tggcacaagg caatgcatcc ctgaggctgc agcgcgtgcg tgtggcggac     420
gagggcagct tcacctgctt cgtgagcatc cgggatttcg gcagcgctgc cgtcagcctg     480
caggtggccg ctccctactc gaagcccagc atgaccctgg agcccaacaa ggacctgcgg     540
ccaggggaca cggtgaccat cacgtgctcc agctaccggg gctaccctga ggctgaggtg     600
ttctggcagg atgggcaggg tgtgcccctg actggcaacg tgaccacgtc gcagatggcc     660
aacgagcagg gcttgtttga tgtgcacagc gtcctgcggg tggtgctggg tgcgaatggc     720
acctacagct gcctggtgcg caaccccgtg ctgcagcagg atgcgcacgg ctctgtcacc     780
atcacgggc agcctatgac attcccccca gaggccctgt gggtgaccgt ggggctctct     840
gtctgtctca ttgcactgct ggtggccctg gctttcgtgt gctggagaaa gatcaaacag     900
agctgtgagg aggagaatgc aggagccgag gaccaggatg gggagggaga aggctccaag     960
acagccctgc agcctctgaa acactctgac agcaaagaag atgatggaca gaaatagcc    1020
```

<210> SEQ ID NO 8
<211> LENGTH: 1561
<212> TYPE: DNA
<213> ORGANISM: Homo sapiens

<400> SEQUENCE: 8

```
tgaccatgag gaccagggag ctgctacccc tccctacagc tcctaccctc tggctgcaat      60
ggggctgcac tgtgagccct gcccccaaca gatgcatcct gctctgacag gtgggctcct     120
tctccaaagg atgcgataca cagaccactg tgcagcctta tttctccaat ggacatgatt     180
cccaagtcat cctgctgcct tttttcttat agacacaatg aacagaccac ccacaacctt     240
agttctctaa gtcatcctgc ctgctgcctt atttcacagt acatacattt cttagggaca     300
cagtacactg accacatcac cacccctcttc ttccagtgct gcgtggacca tctggctgcc     360
tttttttctcc aaaagatgca atattcagac tgactgaccc cctgccttat ttcaccaaag     420
acacgatgca tagtcacccc ggccttgttt ctccaatggc cgtgatacac tagtgatcat     480
gttcagccct gcttccacct gcatagaatc ttttcttctc agacagggac agtgcggcct     540
```

-continued

```
caacatctcc tggagtctag aagctgtttc cttttccctc cttcctcctc ttgctctagc      600
cttaatactg gccttttccc tccctgcccc aagtgaagac agggcactct gcgcccacca      660
catgcacagc tgtgcatgga gacctgcagg tgcacgtgct ggaacacgtg tggttccccc      720
ctggcccagc tcctctgca gtgcccctct ccctgccca tcctccccac ggaagcatgt       780
gctggtcaca ctggttctcc aggggtctgt gatgggccc ctgggggtca gcttctgtcc      840
ctctgccttc tcacctcttt gttcctttct tttcatgtat ccattcagtt gatgtttatt     900
gagcaactac agatgtcagc actgtgttag gtgctggggg ccctgcgtgg aagataaag      960 ttcctccctc aaggactccc catccagctg ggagacagac aactaactac actgcaccct    1020
gcggtttgca gggggctcct gcctggctcc ctgctccaca cctcctctgt ggctcaaggc    1080
ttcctggata cctcacccc atcccaccca taattcttac ccagagcatg gggttggggc     1140
ggaaacctgg agagagggac atagcccctc gccacggcta gagaatctgg tggtgtccaa    1200
aatgtctgtc caggtgtggg caggtgggca ggcaccaagg ccctctggac ctttcatagc    1260
agcagaaaag gcagagcctg ggcagggca gggccaggaa tgctttgggg acaccgaggg     1320
gactgccccc cacccccacc atggtgctat tctggggctg gggcagtctt ttcctggctt    1380
gcctctggcc agctcccggc ctctggtaga gtgagacttc agacgttctg atgccttccg    1440
gatgtcatct ctccctgccc caggaatgga agatgtgagg acttctaatt taaatgtggg    1500
actcggaggg attttgtaaa ctggggtat attttgggga aataaatgt ctttgtaaaa      1560 a                                                                   1561

<210> SEQ ID NO 9
<211> LENGTH: 1323
<212> TYPE: DNA
<213> ORGANISM: Homo sapiens

<400> SEQUENCE: 9
cctcttcccg gacctgctgg cacagggcaa cgcatccctg aggctgcagc gcgtgcgtgt      60
agcggacgag ggcagcttca cctgcttcgt gagcatccgg gatttcggca gcgctgccgt     120
cagcctgcag gtggccgctc cctactcgaa gcccagcatg accctggagc ccaacaagga     180
cctgcggcca ggggacacgg tgtgaccatc acgtgctcca gctaccaggg ctaccctgag     240
gctgaggtgt tctggcagga tgggcagggt gtgcccctga ctggcaacgt gaccacgtcg     300
cagatggcca acgagcaggg cttgtttgat gtgcacagca cctgcgggt ggtgctgggt     360 gcaaatggca cctacagctg cctggtgcgc aaccccgtgc tgcagcagga tgcgcacagc     420
tctgtcacca tcacacccca gagaagcccc acaggagccg tggaggtcca ggtccctgag     480
gacccggtgg tggccctagt gggcaccgat gccaccctgc actgctcctt ctccccgag     540 cctggcttca gcctgacaca gctcaacctc atctggcagc tgacagacac caaacagctg     600
gtgcacagtt tcaccgaagg ccgggaccag ggcagcgcct atgccaaccg cacggccctc     660
ttcccggacc tgctggcaca aggcaatgca tccctgaggc tgcagcgcgt gcgtgtggcg     720
gacgagggca gcttcacctg cttcgtgagc atccgggatt tcggcagcgc tgccgtcagc     780
ctgcaggtgg ccgctcccta ctcgaagccc agcatgaccc tggagcccaa caaggacctg     840
cggccagggg acacggtgac catcacgtgc tccagctacc ggggctaccc tgaggctgag     900
gtgttctggc aggatgggca gggtgtgccc ctgactggca acgtgaccac gtcgcagatg     960
gccaacgagc agggcttgtt tgatgtgcac agcgtcctgc gggtggtgct gggtgcgaat    1020
ggcacctaca gctgcctggt gcgcaaccc gtgctgcagc aggatgcgca cggctctgtc    1080
```

```
accatcacag ggcagcctat gacattcccc ccagaggccc tgtgggtgac cgtgggctc      1140 tctgtctgtc tcattgcact gctggtggcc ctggctttcg tgtgctggag aaagatcaaa      1200
cagagctgtg aggaggagaa tgcaggagcc gaggaccagg atggggaggg agaaggctcc      1260
aagacagccc tgcagcctct gaaacactct gacagcaaag aagatgatgg acaagaaata      1320
gcc                                                                    1323

<210> SEQ ID NO 10
<211> LENGTH: 1561
<212> TYPE: DNA
<213> ORGANISM: Homo sapiens

<400> SEQUENCE: 10
tgaccatgag gaccagggag ctgctacccc tccctacagc tcctaccctc tggctgcaat       60
ggggctgcac tgtgagccct gcccccaaca gatgcatcct gctctgacag gtgggctcct      120
tctccaaagg atgcgataca cagaccactg tgcagcctta tttctccaat ggacatgatt      180
cccaagtcat cctgctgcct ttttcttat agacacaatg aacagaccac ccacaacctt      240
agttctctaa gtcatcctgc ctgctgcctt atttcacagt acatacattt cttagggaca      300
cagtacactg accacatcac caccctcttc ttccagtgct gcgtggacca tctggctgcc      360
ttttttctcc aaaagatgca atattcagac tgactgaccc cctgccttat ttcaccaaag      420
acacgatgca tagtcacccc ggccttgttt ctccaatggc cgtgatacac tagtgatcat      480
gttcagccct gcttccacct gcatagaatc ttttcttctc agacagggac agtgcggcct      540
caacatctcc tggagtctag aagctgtttc ctttcccctc cttcctcctc ttgctctagc      600
cttaatactg gccttttccc tccctgcccc aagtgaagac agggcactct gcgcccacca      660
catgcacagc tgtgcatgga gacctgcagg tgcacgtgct ggaacacgtg tggttccccc      720
ctggcccagc ctcctctgca gtgcccctct cccctgccca tcctccccac ggaagcatgt      780
gctggtcaca ctggttctcc aggggtctgt gatggggccc ctgggggtca gcttctgtcc      840
ctctgccttc tcacctcttt gttcctttct tttcatgtat ccattcagtt gatgtttatt      900
gagcaactac agatgtcagc actgtgttag gtgctggggg ccctgcgtgg aagataaag      960 ttcctccctc aaggactccc catccagctg ggagacagac aactaactac actgcaccct     1020
gcggtttgca gggggctcct gcctggctcc ctgctccaca cctcctctgt ggctcaaggc     1080
ttcctggata cctcacccc atcccaccca taattcttac ccagagcatg gggttggggc     1140
ggaaacctgg agagggac atagccctc gccacggcta gagaatctgg tggtgtccaa      1200
aatgtctgtc caggtgtggg caggtgggca ggcaccaagg ccctctggac ctttcatagc     1260
agcagaaaag gcagagcctg ggcagggca gggccaggaa tgctttgggg acaccgaggg     1320
gactgccccc caccccacc atggtgctat tctggggctg gggcagtctt ttcctggctt     1380
gcctctggcc agctcccggc ctctggtaga gtgagacttc agacgttctg atgccttccg     1440
gatgtcatct ctccctgccc caggaatgga agatgtgagg acttctaatt taaatgtggg     1500
actcggaggg attttgtaaa ctgggggtat attttgggga aataaatgt ctttgtaaaa     1560 a                                                                    1561

<210> SEQ ID NO 11
<211> LENGTH: 1602
<212> TYPE: DNA
<213> ORGANISM: Homo sapiens
```

<400> SEQUENCE: 11

```
atgctgcgtc ggcggggcag ccctggcatg ggtgtgcatg tgggtgcagc cctgggagca      60
ctgtggttct gcctcacagg agccctggag gtccaggtcc ctgaagaccc agtggtggca     120
ctggtgggca ccgatgccac cctgtgctgc tccttctccc ctgagcctgg cttcagcctg     180
gcacagctca acctcatctg gcagctgaca gataccaaac agctggtgca cagctttgct     240
gagggccagg accagggcag cgcctatgcc aaccgcacgg ccctcttccc ggacctgctg     300
gcacagggca acgcatccct gaggctgcag gcgtgcgtg tggcggacga gggcagcttc      360
acctgcttcg tgagcatccg ggatttcggc agcgctgccg tcagcctgca ggtggccgct     420
ccctactcga agcccagcat gaccctggag cccaacaagg acctgcggcc aggggacacg     480
gtgaccatca cgtgctccag ctaccagggc taccctgagg ctgaggtgtt ctggcaggat     540
gggcagggtg tgcccctgac tgcaacgtg accacgtcgc agatggccaa cgagcagggc      600
ttgtttgatg tgcacagcat cctgcgggtg gtgctgggtg caaatggcac ctacagctgc     660
ctggtgcgca ccccgtgct gcagcaggat gcgcacagct ctgtcaccat cacacccccag    720
agaagcccca caggagccgt ggaggtccag gtccctgagg acccggtggt ggccctagtg     780
ggcaccgatg ccaccctgcg ctgctccttc tcccccgagc ctggcttcag cctggcacag     840
ctcaacctca tctggcagct gacagacacc aaacagctgg tgcacagttt caccgaaggc     900
cgggaccagg gcagcgccta tgccaaccgc acggccctct cccggacct gctggcacaa     960
ggcaatgcat ccctgaggct gcagcgcgtg cgtgtggcgg acgagggcag cttcacctgc    1020
ttcgtgagca tccgggattt cggcagcgct gccgtcagcc tgcaggtggc cgctcccctac    1080
tcgaagccca gcatgaccct ggagcccaac aaggacctgc ggccagggga cacggtgacc     1140
atcacgtgct ccagctaccg gggctaccct gaggctgagg tgttctggca ggatgggcag     1200
ggtgtgcccc tgactggcaa cgtgaccacg tcgcagatgg ccaacgagca gggcttgttt     1260
gatgtgcaca gcgtcctgcg ggtggtgctg ggtgcgaatg gcacctacag ctgcctggtg     1320
cgcaacccg tgctgcagca ggatgcgcac ggctctgtca ccatcacagg gcagcctatg     1380
acattccccc cagaggccct gtgggtgacc gtggggctgt ctgtctgtct cattgcactg     1440
ctggtggccc tggctttcgt gtgctggaga aagatcaaac agagctgtga ggaggagaat     1500
gcaggagctg aggaccagga tggggaggga aaggctcca agacagccct gcagcctctg      1560
aaacactctg acagcaaaga agatgatgga caagaaatag cc                        1602
```

<210> SEQ ID NO 12
<211> LENGTH: 568
<212> TYPE: DNA
<213> ORGANISM: Homo sapiens

<400> SEQUENCE: 12

```
tgaccatgag gaccagggag ctgctacccc tccctacagc tcctaccctc tggctgcaat      60
ggggctgcac tgtgagccct gcccccaaca gatgcatcct gctctgacag gtgggctcct    120
tctccaaagg atgcgataca cagaccactg tgcagcctta tttctccaat ggacatgatt     180
cccaagtcat cctgctgcct ttttcttat agacacaatg aacagaccac ccacaacctt     240
agttctctaa gtcatcctgc ctgctgcctt atttcacagt acatacattt cttagggaca     300
cagtacactg accacatcac caccctcttc ttccagtgct gcgtggacca tctggctgcc     360
tttttctcc aaaagatgca atattcagac tgactgaccc cctgccttat ttcaccaaag     420
acacgatgca tagtcacccc gaccttgttt ctccaatggc cgtgatacac tagtgatcat     480
```

-continued

```
gttcagccct gcttccacct gcatagaatc ttttcttctc agacagggac agtgcggcct      540
caacatctcc tggagtctag gcggccgc                                        568
```

<210> SEQ ID NO 13
<211> LENGTH: 288
<212> TYPE: PRT
<213> ORGANISM: Homo sapiens

<400> SEQUENCE: 13

```
Met Gly His Thr Arg Arg Gln Gly Thr Ser Pro Ser Lys Cys Pro Tyr
 1               5                  10                  15

Leu Asn Phe Phe Gln Leu Leu Val Leu Ala Gly Leu Ser His Phe Cys
            20                  25                  30

Ser Gly Val Ile His Val Thr Lys Glu Val Lys Glu Val Ala Thr Leu
        35                  40                  45

Ser Cys Gly His Asn Val Ser Val Glu Glu Leu Ala Gln Thr Arg Ile
    50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255

Ile Phe Val Ile Cys Cys Leu Thr Tyr Cys Phe Ala Pro Arg Cys Arg
            260                 265                 270

Glu Arg Arg Arg Asn Glu Arg Leu Arg Arg Glu Ser Val Arg Pro Val
        275                 280                 285
```

<210> SEQ ID NO 14
<211> LENGTH: 288
<212> TYPE: PRT
<213> ORGANISM: Macaca mulatta

<400> SEQUENCE: 14

```
Met Gly His Thr Arg Arg Gln Glu Ile Ser Pro Ser Lys Cys Pro Tyr
 1               5                  10                  15

Leu Lys Phe Phe Gln Leu Leu Val Leu Ala Cys Leu Ser His Phe Cys
```

```
                20                  25                  30

Ser Gly Val Ile His Val Thr Lys Glu Val Lys Val Ala Thr Leu
            35                  40                  45

Ser Cys Gly His Asn Val Ser Val Glu Glu Leu Ala Gln Thr Arg Ile
50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
                100                 105                 110

Thr Tyr Glu Cys Val Val Leu Lys Tyr Glu Lys Asp Ala Phe Lys Arg
            115                 120                 125

Glu His Leu Ala Glu Val Met Leu Ser Val Lys Ala Asp Phe Pro Thr
        130                 135                 140

Pro Ser Ile Thr Asp Ser Glu Ile Pro Pro Ser Asn Ile Arg Arg Ile
145                 150                 155                 160

Ile Cys Ser Asn Ser Gly Gly Phe Pro Glu Pro His Leu Ser Trp Leu
                165                 170                 175

Glu Asn Gly Glu Glu Leu Asn Ala Ile Ser Thr Thr Val Ser Gln Asp
            180                 185                 190

Pro Glu Thr Glu Leu Tyr Thr Val Ser Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr Pro Lys Gln Glu His Phe Pro
225                 230                 235                 240

Asp Asn Leu Leu Pro Ser Trp Ala Ile Ile Leu Ile Ser Val Asn Gly
                245                 250                 255

Ile Phe Val Ile Cys Cys Leu Thr Tyr Cys Phe Ala Pro Arg Cys Arg
            260                 265                 270

Glu Arg Arg Arg Asn Glu Thr Leu Arg Arg Glu Ser Val Arg Pro Val
        275                 280                 285

<210> SEQ ID NO 15
<211> LENGTH: 299
<212> TYPE: PRT
<213> ORGANISM: Oryctolagus sp.

<400> SEQUENCE: 15

Met Gly His Thr Leu Arg Pro Gly Thr Pro Leu Pro Arg Cys Leu His
1               5                   10                  15

Leu Lys Leu Cys Leu Leu Leu Ala Leu Ala Gly Leu His Phe Ser Ser
                20                  25                  30

Gly Ile Ser Gln Val Thr Lys Ser Val Lys Glu Met Ala Ala Leu Ser
            35                  40                  45

Cys Asp Tyr Asn Ile Ser Ile Asp Glu Leu Ala Arg Met Arg Ile Tyr
        50                  55                  60

Trp Gln Lys Asp Gln Gln Met Val Leu Ser Ile Ile Ser Gly Gln Val
65                  70                  75                  80

Glu Val Trp Pro Glu Tyr Lys Asn Arg Thr Phe Pro Asp Ile Ile Asn
                85                  90                  95

Asn Leu Ser Leu Met Ile Leu Ala Leu Arg Leu Ser Asp Lys Gly Thr
            100                 105                 110
```

-continued

```
Tyr Thr Cys Val Val Gln Lys Asn Glu Asn Gly Ser Phe Arg Arg Glu
        115                 120                 125
His Leu Thr Ser Val Thr Leu Ser Ile Arg Ala Asp Phe Pro Val Pro
    130                 135                 140
Ser Ile Thr Asp Ile Gly His Pro Asp Pro Asn Val Lys Arg Ile Arg
145                 150                 155                 160
Cys Ser Ala Ser Gly Gly Phe Pro Glu Pro Arg Leu Ala Trp Met Glu
                165                 170                 175
Asp Gly Glu Glu Leu Asn Ala Val Asn Thr Thr Val Asp Gln Asp Leu
            180                 185                 190
Asp Thr Glu Leu Tyr Ser Val Ser Ser Glu Leu Asp Phe Asn Val Thr
        195                 200                 205
Asn Asn His Ser Ile Val Cys Leu Ile Lys Tyr Gly Glu Leu Ser Val
    210                 215                 220
Ser Gln Ile Phe Pro Trp Ser Lys Pro Lys Gln Glu Pro Pro Ile Asp
225                 230                 235                 240
Gln Leu Pro Phe Trp Val Ile Ile Pro Val Ser Gly Ala Leu Val Leu
                245                 250                 255
Thr Ala Val Val Leu Tyr Cys Leu Ala Cys Arg His Val Ala Arg Trp
            260                 265                 270
Lys Arg Thr Arg Arg Asn Glu Glu Thr Val Gly Thr Glu Arg Leu Ser
        275                 280                 285
Pro Ile Tyr Leu Gly Ser Ala Gln Ser Ser Gly
    290                 295

<210> SEQ ID NO 16
<211> LENGTH: 292
<212> TYPE: PRT
<213> ORGANISM: Felis catus

<400> SEQUENCE: 16

Met Gly His Ala Ala Lys Trp Lys Thr Pro Leu Leu Lys His Pro Tyr
  1               5                  10                  15
Pro Lys Leu Phe Pro Leu Leu Met Leu Ala Ser Leu Phe Tyr Phe Cys
                20                  25                  30
Ser Gly Ile Ile Gln Val Asn Lys Thr Val Glu Glu Val Ala Val Leu
            35                  40                  45
Ser Cys Asp Tyr Asn Ile Ser Thr Lys Glu Leu Thr Glu Ile Arg Ile
    50                  55                  60
Tyr Trp Gln Lys Asp Asp Glu Met Val Leu Ala Val Met Ser Gly Lys
65                  70                  75                  80
Val Gln Val Trp Pro Lys Tyr Lys Asn Arg Thr Phe Thr Asp Val Thr
                85                  90                  95
Asp Asn His Ser Ile Val Ile Met Ala Leu Arg Leu Ser Asp Asn Gly
            100                 105                 110
Lys Tyr Thr Cys Ile Ile Gln Lys Ile Glu Lys Gly Ser Tyr Lys Val
    115                 120                 125
Lys His Leu Thr Ser Val Met Leu Leu Val Arg Ala Asp Phe Pro Val
130                 135                 140
Pro Ser Ile Thr Asp Leu Gly Asn Pro Ser His Asn Ile Lys Arg Ile
145                 150                 155                 160
Met Cys Leu Thr Ser Gly Gly Phe Pro Lys Pro His Leu Ser Trp Leu
                165                 170                 175
Glu Asn Glu Glu Glu Leu Asn Ala Ile Asn Thr Thr Val Ser Gln Asp
            180                 185                 190
```

```
Pro Glu Thr Glu Leu Tyr Thr Ile Ser Ser Glu Leu Asp Phe Asn Met
        195                 200                 205

Thr Asn Asn His Ser Phe Leu Cys Leu Val Lys Tyr Gly Asn Leu Leu
        210                 215                 220

Val Ser Gln Ile Phe Asn Trp Gln Lys Ser Glu Pro Gln Pro Ser Asn
225                 230                 235                 240

Asn Gln Leu Trp Ile Ile Leu Ser Ser Val Val Ser Gly Ile Val
                245                 250                 255

Val Ile Thr Ala Leu Thr Leu Arg Cys Leu Val His Arg Pro Ala Ala
                260                 265                 270

Arg Trp Arg Gln Arg Glu Met Gly Arg Ala Arg Lys Trp Lys Arg Ser
        275                 280                 285

His Leu Ser Thr
        290

<210> SEQ ID NO 17
<211> LENGTH: 306
<212> TYPE: PRT
<213> ORGANISM: mus sp.

<400> SEQUENCE: 17

Met Ala Cys Asn Cys Gln Leu Met Gln Asp Thr Pro Leu Leu Lys Phe
 1               5                  10                  15

Pro Cys Pro Arg Leu Ile Leu Leu Phe Val Leu Leu Ile Arg Leu Ser
             20                  25                  30

Gln Val Ser Ser Asp Val Asp Glu Gln Leu Ser Lys Ser Val Lys Asp
         35                  40                  45

Lys Val Leu Leu Pro Cys Arg Tyr Asn Ser Pro His Glu Asp Glu Ser
     50                  55                  60

Glu Asp Arg Ile Tyr Trp Gln Lys His Asp Lys Val Val Leu Ser Val
 65                  70                  75                  80

Ile Ala Gly Lys Leu Lys Val Trp Pro Glu Tyr Lys Asn Arg Thr Leu
                 85                  90                  95

Tyr Asp Asn Thr Thr Tyr Ser Leu Ile Ile Leu Gly Leu Val Leu Ser
            100                 105                 110

Asp Arg Gly Thr Tyr Ser Cys Val Val Gln Lys Lys Glu Arg Gly Thr
        115                 120                 125

Tyr Glu Val Lys His Leu Ala Leu Val Lys Leu Ser Ile Lys Ala Asp
    130                 135                 140

Phe Ser Thr Pro Asn Ile Thr Glu Ser Gly Asn Pro Ser Ala Asp Thr
145                 150                 155                 160

Lys Arg Ile Thr Cys Phe Ala Ser Gly Gly Phe Pro Lys Pro Arg Phe
                165                 170                 175

Ser Trp Leu Glu Asn Gly Arg Glu Leu Pro Gly Ile Asn Thr Thr Ile
            180                 185                 190

Ser Gln Asp Pro Glu Ser Glu Leu Tyr Thr Ile Ser Ser Gln Leu Asp
        195                 200                 205

Phe Asn Thr Thr Arg Asn His Thr Ile Lys Cys Leu Ile Lys Tyr Gly
    210                 215                 220

Asp Ala His Val Ser Glu Asp Phe Thr Trp Glu Lys Pro Pro Glu Asp
225                 230                 235                 240

Pro Pro Asp Ser Lys Asn Thr Leu Val Leu Phe Gly Ala Gly Phe Gly
                245                 250                 255

Ala Val Ile Thr Val Val Val Ile Val Val Ile Ile Lys Cys Phe Cys
```

```
                    260                 265                 270
Lys His Arg Ser Cys Phe Arg Arg Asn Glu Ala Ser Arg Glu Thr Asn
            275                 280                 285

Asn Ser Leu Thr Phe Gly Pro Glu Glu Ala Leu Ala Glu Gln Thr Val
        290                 295                 300

Phe Leu
305

<210> SEQ ID NO 18
<211> LENGTH: 329
<212> TYPE: PRT
<213> ORGANISM: Felis catus

<400> SEQUENCE: 18

Met Gly Ile Cys Asp Ser Thr Met Gly Leu Ser His Thr Leu Leu Val
  1               5                  10                  15

Met Ala Leu Leu Leu Ser Gly Val Ser Ser Met Lys Ser Gln Ala Tyr
             20                  25                  30

Phe Asn Lys Thr Gly Glu Leu Pro Cys His Phe Thr Asn Ser Gln Asn
         35                  40                  45

Ile Ser Leu Asp Glu Leu Val Val Phe Trp Gln Asp Gln Asp Lys Leu
     50                  55                  60

Val Leu Tyr Glu Ile Phe Arg Gly Lys Glu Asn Pro Gln Asn Val His
 65                  70                  75                  80

Leu Lys Tyr Lys Gly Arg Thr Ser Phe Asp Lys Asp Asn Trp Thr Leu
                 85                  90                  95

Arg Leu His Asn Val Gln Ile Lys Asp Lys Gly Thr Tyr His Cys Phe
            100                 105                 110

Ile His Tyr Lys Gly Pro Lys Gly Leu Val Pro Met His Gln Met Ser
        115                 120                 125

Ser Asp Leu Ser Val Leu Ala Asn Phe Ser Gln Pro Glu Ile Thr Val
    130                 135                 140

Thr Ser Asn Arg Thr Glu Asn Ser Gly Ile Ile Asn Leu Thr Cys Ser
145                 150                 155                 160

Ser Ile Gln Gly Tyr Pro Glu Pro Lys Glu Met Tyr Phe Gln Leu Asn
                165                 170                 175

Thr Glu Asn Ser Thr Thr Lys Tyr Asp Thr Val Met Lys Lys Ser Gln
            180                 185                 190

Asn Asn Val Thr Glu Leu Tyr Asn Val Ser Ile Ser Leu Pro Phe Ser
        195                 200                 205

Val Pro Glu Ala His Asn Val Ser Val Phe Cys Ala Leu Lys Leu Glu
    210                 215                 220

Thr Leu Glu Met Leu Leu Ser Leu Pro Phe Asn Ile Asp Ala Gln Pro
225                 230                 235                 240

Lys Asp Lys Asp Pro Glu Gln Gly His Phe Leu Trp Ile Ala Ala Val
                245                 250                 255

Leu Val Met Phe Val Val Phe Cys Gly Met Val Ser Phe Lys Thr Leu
            260                 265                 270

Arg Lys Arg Lys Lys Lys Gln Pro Gly Pro Ser His Glu Cys Glu Thr
        275                 280                 285

Ile Lys Arg Glu Arg Lys Glu Ser Lys Gln Thr Asn Glu Arg Val Pro
    290                 295                 300

Tyr His Val Pro Glu Arg Ser Asp Glu Ala Gln Cys Val Asn Ile Leu
305                 310                 315                 320
```

Lys Thr Ala Ser Gly Asp Lys Asn Gln
             325

<210> SEQ ID NO 19
<211> LENGTH: 329
<212> TYPE: PRT
<213> ORGANISM: Canis familiaris

<400> SEQUENCE: 19

Met Tyr Leu Arg Cys Thr Met Glu Leu Asn Asn Ile Leu Phe Val Met
 1               5                  10                  15

Thr Leu Leu Tyr Gly Ala Ala Ser Met Lys Ser Gln Ala Tyr Phe
             20                  25                  30

Asn Lys Thr Gly Glu Leu Pro Cys His Phe Thr Asn Ser Gln Asn Ile
             35                  40                  45

Ser Leu Asp Glu Leu Val Val Phe Trp Gln Asp Gln Asp Lys Leu Val
     50                  55                  60

Leu Tyr Glu Leu Tyr Arg Gly Lys Glu Asn Pro Gln Asn Val His Arg
 65                  70                  75                  80

Lys Tyr Lys Gly Arg Thr Ser Phe Asp Lys Asp Asn Trp Thr Leu Arg
                 85                  90                  95

Leu His Asn Ile Gln Ile Lys Asp Lys Gly Leu Tyr Gln Cys Phe Val
                100                 105                 110

His His Lys Gly Pro Lys Gly Leu Val Pro Met His Gln Met Asn Ser
            115                 120                 125

Asp Leu Ser Val Leu Ala Asn Phe Ser Gln Pro Glu Ile Met Val Thr
        130                 135                 140

Ser Asn Arg Thr Glu Asn Ser Gly Ile Ile Asn Leu Thr Cys Ser Ser
145                 150                 155                 160

Ile Gln Gly Tyr Pro Glu Pro Lys Glu Met Tyr Phe Leu Val Lys Thr
                165                 170                 175

Glu Asn Ser Ser Thr Lys Tyr Asp Thr Val Met Lys Ser Gln Asn
            180                 185                 190

Asn Val Thr Glu Leu Tyr Asn Val Ser Ile Ser Leu Ser Phe Ser Val
        195                 200                 205

Pro Glu Ala Ser Asn Val Ser Ile Phe Cys Val Leu Gln Leu Glu Ser
    210                 215                 220

Met Lys Leu Pro Ser Leu Pro Tyr Asn Ile Asp Ala His Thr Lys Pro
225                 230                 235                 240

Thr Pro Asp Gly Asp His Ile Leu Trp Ile Ala Ala Leu Leu Val Met
                245                 250                 255

Leu Val Ile Leu Cys Gly Met Val Phe Phe Leu Thr Leu Arg Lys Arg
                260                 265                 270

Lys Lys Lys Gln Pro Gly Pro Ser His Glu Cys Glu Thr Asn Lys Val
            275                 280                 285

Glu Arg Lys Glu Ser Glu Gln Thr Lys Glu Arg Val Arg Tyr His Glu
        290                 295                 300

Thr Glu Arg Ser Asp Glu Ala Gln Cys Val Asn Ile Ser Lys Thr Ala
305                 310                 315                 320

Ser Gly Asp Asn Ser Thr Thr Gln Phe
                325

<210> SEQ ID NO 20
<211> LENGTH: 325
<212> TYPE: PRT
<213> ORGANISM: sus sp.

```
<400> SEQUENCE: 20

Met Gly Leu Ser Asn Ile Leu Phe Val Met Leu Leu Ser Gly
  1               5                  10                  15

Ala Ala Ser Leu Lys Ser Gln Ala Tyr Phe Asn Glu Thr Gly Glu Leu
             20                  25                  30

Pro Cys His Phe Thr Asn Ser Gln Asn Leu Ser Leu Asp Glu Leu Val
         35                  40                  45

Ile Phe Trp Gln Asp Gln Asp Asn Leu Val Leu Tyr Glu Leu Tyr Arg
     50                  55                  60

Gly Gln Glu Lys Pro His Asn Val Asn Ser Lys Tyr Met Gly Arg Thr
 65                  70                  75                  80

Ser Phe Asp Gln Ala Thr Trp Thr Leu Arg Leu His Asn Val Gln Ile
                 85                  90                  95

Lys Asp Lys Gly Ser Tyr Gln Cys Phe Ile His His Lys Gly Pro His
            100                 105                 110

Gly Leu Val Pro Ile His Gln Met Ser Ser Asp Leu Ser Leu Leu Ala
            115                 120                 125

Asn Phe Ser Gln Pro Glu Ile Asn Leu Leu Thr Asn His Thr Glu Asn
130                 135                 140

Ser Val Ile Asn Leu Thr Cys Ser Ser Thr Gln Gly Tyr Pro Glu Pro
145                 150                 155                 160

Gln Arg Met Tyr Met Leu Leu Asn Thr Lys Asn Ser Thr Thr Glu His
                165                 170                 175

Asp Ala Asp Met Lys Lys Ser Gln Asn Asn Ile Thr Glu Leu Tyr Asn
            180                 185                 190

Val Ser Ile Arg Val Ser Leu Pro Ile Pro Glu Thr Asn Val Ser
            195                 200                 205

Ile Val Cys Val Leu Gln Leu Glu Pro Ser Lys Thr Leu Leu Phe Ser
            210                 215                 220

Leu Pro Cys Asn Ile Asp Ala Lys Pro Pro Val Gln Pro Pro Val Pro
225                 230                 235                 240

Asp His Ile Leu Trp Ile Ala Ala Leu Leu Val Thr Val Val Val Val
                245                 250                 255

Cys Gly Met Val Ser Phe Val Thr Leu Arg Lys Arg Lys Lys Lys Gln
            260                 265                 270

Pro Gly Pro Ser Asn Glu Cys Gly Glu Thr Ile Lys Met Asn Arg Lys
            275                 280                 285

Ala Ser Glu Gln Thr Lys Asn Arg Ala Glu Val His Glu Arg Ser Asp
290                 295                 300

Asp Ala Gln Cys Asp Val Asn Ile Leu Lys Thr Ala Ser Asp Asp Asn
305                 310                 315                 320

Ser Thr Thr Asp Phe
            325

<210> SEQ ID NO 21
<211> LENGTH: 323
<212> TYPE: PRT
<213> ORGANISM: Homo sapiens

<400> SEQUENCE: 21

Met Gly Leu Ser Asn Ile Leu Phe Val Met Ala Phe Leu Leu Ser Gly
  1               5                  10                  15

Ala Ala Pro Leu Lys Ile Gln Ala Tyr Phe Asn Glu Thr Ala Asp Leu
             20                  25                  30
```

```
Pro Cys Gln Phe Ala Asn Ser Gln Asn Gln Ser Leu Ser Glu Leu Val
        35                  40                  45

Val Phe Trp Gln Asp Gln Glu Asn Leu Val Leu Asn Glu Val Tyr Leu
 50                  55                  60

Gly Lys Glu Lys Phe Asp Ser Val His Ser Lys Tyr Met Gly Arg Thr
 65                  70                  75                  80

Ser Phe Asp Ser Asp Ser Trp Thr Leu Arg Leu His Asn Leu Gln Ile
                 85                  90                  95

Lys Asp Lys Gly Leu Tyr Gln Cys Ile Ile His His Lys Lys Pro Thr
                100                 105                 110

Gly Met Ile Arg Ile His Gln Met Asn Ser Glu Leu Ser Val Leu Ala
            115                 120                 125

Asn Phe Ser Gln Pro Glu Ile Val Pro Ile Ser Asn Ile Thr Glu Asn
130                 135                 140

Val Tyr Ile Asn Leu Thr Cys Ser Ser Ile His Gly Tyr Pro Glu Pro
145                 150                 155                 160

Lys Lys Met Ser Val Leu Leu Arg Thr Lys Asn Ser Thr Ile Glu Tyr
                165                 170                 175

Asp Gly Ile Met Gln Lys Ser Gln Asp Asn Val Thr Glu Leu Tyr Asp
            180                 185                 190

Val Ser Ile Ser Leu Ser Val Ser Phe Pro Asp Val Thr Ser Asn Met
            195                 200                 205

Thr Ile Phe Cys Ile Leu Glu Thr Asp Lys Thr Arg Leu Leu Ser Ser
210                 215                 220

Pro Phe Ser Ile Glu Leu Glu Asp Pro Gln Pro Pro Asp His Ile
225                 230                 235                 240

Pro Trp Ile Thr Ala Val Leu Pro Thr Val Ile Ile Cys Val Met Val
            245                 250                 255

Phe Cys Leu Ile Leu Trp Lys Trp Lys Lys Lys Arg Pro Arg Asn
                260                 265                 270

Ser Tyr Lys Cys Gly Thr Asn Thr Met Glu Arg Glu Glu Ser Glu Gln
            275                 280                 285

Thr Lys Lys Arg Glu Lys Ile His Ile Pro Glu Arg Ser Asp Glu Ala
290                 295                 300

Gln Arg Val Phe Lys Ser Ser Lys Thr Ser Ser Cys Asp Lys Ser Asp
305                 310                 315                 320

Thr Cys Phe

<210> SEQ ID NO 22
<211> LENGTH: 309
<212> TYPE: PRT
<213> ORGANISM: Mus musculus

<400> SEQUENCE: 22

Met Asp Pro Arg Cys Thr Met Gly Leu Ala Ile Leu Ile Phe Val Thr
  1               5                  10                  15

Val Leu Leu Ile Ser Asp Ala Val Ser Val Glu Thr Gln Ala Tyr Phe
             20                  25                  30

Asn Gly Thr Ala Tyr Leu Pro Cys Pro Phe Thr Lys Ala Gln Asn Ile
             35                  40                  45

Ser Leu Ser Glu Leu Val Val Phe Trp Gln Asp Gln Gln Lys Leu Val
 50                  55                  60

Leu Tyr Glu His Tyr Leu Gly Thr Glu Lys Leu Asp Ser Val Asn Ala
 65                  70                  75                  80
```

-continued

```
Lys Tyr Leu Gly Arg Thr Ser Phe Asp Arg Asn Asn Trp Thr Leu Arg
                85                  90                  95

Leu His Asn Val Gln Ile Lys Asp Met Gly Ser Tyr Asp Cys Phe Ile
            100                 105                 110

Gln Lys Lys Pro Pro Thr Gly Ser Ile Ile Leu Gln Gln Thr Leu Thr
        115                 120                 125

Glu Leu Ser Val Ile Ala Asn Phe Ser Glu Pro Glu Ile Lys Leu Ala
    130                 135                 140

Gln Asn Val Thr Gly Asn Ser Gly Ile Asn Leu Thr Cys Thr Ser Lys
145                 150                 155                 160

Gln Gly His Pro Lys Pro Lys Lys Met Tyr Phe Leu Ile Thr Asn Ser
                165                 170                 175

Thr Asn Glu Tyr Gly Asp Asn Met Gln Ile Ser Gln Asp Asn Val Thr
            180                 185                 190

Glu Leu Phe Ser Ile Ser Asn Ser Leu Ser Leu Ser Phe Pro Asp Gly
        195                 200                 205

Val Trp His Met Thr Val Val Cys Val Leu Glu Thr Glu Ser Met Lys
    210                 215                 220

Ile Ser Ser Lys Pro Leu Asn Phe Thr Gln Glu Phe Pro Ser Pro Gln
225                 230                 235                 240

Thr Tyr Trp Lys Glu Ile Thr Ala Ser Val Thr Val Ala Leu Leu Leu
                245                 250                 255

Val Met Leu Leu Ile Ile Val Cys His Lys Lys Pro Asn Gln Pro Ser
            260                 265                 270

Arg Pro Ser Asn Thr Ala Ser Lys Leu Glu Arg Asp Ser Asn Ala Asp
        275                 280                 285

Arg Glu Thr Ile Asn Leu Lys Glu Leu Glu Pro Gln Ile Ala Ser Ala
    290                 295                 300

Lys Pro Asn Ala Glu
305

<210> SEQ ID NO 23
<211> LENGTH: 303
<212> TYPE: PRT
<213> ORGANISM: Mus musculus

<400> SEQUENCE: 23

Met Gly Leu Ala Ile Leu Ile Phe Val Thr Val Leu Leu Ile Ser Asp
  1               5                  10                  15

Ala Val Ser Val Glu Thr Gln Ala Tyr Phe Asn Gly Thr Ala Tyr Leu
                20                  25                  30

Pro Cys Pro Phe Thr Lys Ala Gln Asn Ile Ser Leu Ser Glu Leu Val
            35                  40                  45

Val Phe Trp Gln Asp Gln Gln Lys Leu Val Leu Tyr Glu His Tyr Leu
        50                  55                  60

Gly Thr Glu Lys Leu Asp Ser Val Asn Ala Lys Tyr Leu Gly Arg Thr
 65                  70                  75                  80

Ser Phe Asp Arg Asn Asn Trp Thr Leu Arg Leu His Asn Val Gln Ile
                85                  90                  95

Lys Asp Met Gly Ser Tyr Asp Cys Phe Ile Gln Lys Lys Pro Pro Thr
            100                 105                 110

Gly Ser Ile Ile Leu Gln Gln Thr Leu Thr Glu Leu Ser Val Ile Ala
        115                 120                 125

Asn Phe Ser Glu Pro Glu Ile Lys Leu Ala Gln Asn Val Thr Gly Asn
```

```
            130                 135                 140
Ser Gly Ile Asn Leu Thr Cys Thr Ser Lys Gln Gly His Pro Lys Pro
145                 150                 155                 160

Lys Lys Met Tyr Phe Leu Ile Thr Asn Ser Thr Asn Glu Tyr Gly Asp
                165                 170                 175

Asn Met Gln Ile Ser Gln Asp Asn Val Thr Glu Leu Phe Ser Ile Ser
            180                 185                 190

Asn Ser Leu Ser Leu Ser Phe Pro Asp Gly Val Trp His Met Thr Val
        195                 200                 205

Val Cys Val Leu Glu Thr Glu Ser Met Lys Ile Ser Ser Lys Pro Leu
    210                 215                 220

Asn Phe Thr Gln Glu Phe Pro Ser Pro Gln Thr Tyr Trp Lys Glu Ile
225                 230                 235                 240

Thr Ala Ser Val Thr Val Ala Leu Leu Val Met Leu Leu Ile Ile
                245                 250                 255

Val Cys His Lys Lys Pro Asn Gln Pro Ser Arg Pro Ser Asn Thr Ala
            260                 265                 270

Ser Lys Leu Glu Arg Asp Ser Asn Ala Asp Arg Glu Thr Ile Asn Leu
        275                 280                 285

Lys Glu Leu Glu Pro Gln Ile Ala Ser Ala Lys Pro Asn Ala Glu
    290                 295                 300

<210> SEQ ID NO 24
<211> LENGTH: 534
<212> TYPE: PRT
<213> ORGANISM: Unknown
<220> FEATURE:
<223> OTHER INFORMATION: Description of Unknown Organism: Sequence
      mz5020.protein from Figure 4.

<400> SEQUENCE: 24

Met Leu Arg Arg Arg Gly Ser Pro Gly Met Gly Val His Val Gly Ala
  1               5                  10                  15

Ala Leu Gly Ala Leu Trp Phe Cys Leu Thr Gly Ala Leu Glu Val Gln
                20                  25                  30

Val Pro Glu Asp Pro Val Val Ala Leu Val Gly Thr Asp Ala Thr Leu
            35                  40                  45

Cys Cys Ser Phe Ser Pro Glu Pro Gly Phe Ser Leu Ala Gln Leu Asn
        50                  55                  60

Leu Ile Trp Gln Leu Thr Asp Thr Lys Gln Leu Val His Ser Phe Ala
65                  70                  75                  80

Glu Gly Gln Asp Gln Gly Ser Ala Tyr Ala Asn Arg Thr Ala Leu Phe
                85                  90                  95

Pro Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
        115                 120                 125

Phe Gly Ser Ala Ala Val Ser Leu Gln Val Ala Ala Pro Tyr Ser Lys
    130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Gln Gly Tyr Pro Glu Ala Glu Val
                165                 170                 175

Phe Trp Gln Asp Gly Gln Gly Val Pro Leu Thr Gly Asn Val Thr Thr
            180                 185                 190
```

```
Ser Gln Met Ala Asn Glu Gln Gly Leu Phe Asp Val His Ser Ile Leu
        195                 200                 205

Arg Val Leu Gly Ala Asn Gly Thr Tyr Ser Cys Leu Val Arg Asn
210                 215                 220

Pro Val Leu Gln Gln Asp Ala His Ser Ser Val Thr Ile Thr Pro Gln
225                 230                 235                 240

Arg Ser Pro Thr Gly Ala Val Glu Val Gln Val Pro Glu Asp Pro Val
                245                 250                 255

Val Ala Leu Val Gly Thr Asp Ala Thr Leu Arg Cys Ser Phe Ser Pro
            260                 265                 270

Glu Pro Gly Phe Ser Leu Ala Gln Leu Asn Leu Ile Trp Gln Leu Thr
        275                 280                 285

Asp Thr Lys Gln Leu Val His Ser Phe Thr Glu Gly Arg Asp Gln Gly
    290                 295                 300

Ser Ala Tyr Ala Asn Arg Thr Ala Leu Phe Pro Asp Leu Leu Ala Gln
305                 310                 315                 320

Gly Asn Ala Ser Leu Arg Leu Gln Arg Val Arg Val Ala Asp Glu Gly
                325                 330                 335

Ser Phe Thr Cys Phe Val Ser Ile Arg Asp Phe Gly Ser Ala Ala Val
            340                 345                 350

Ser Leu Gln Val Ala Ala Pro Tyr Ser Lys Pro Ser Met Thr Leu Glu
        355                 360                 365

Pro Asn Lys Asp Leu Arg Pro Gly Asp Thr Val Thr Ile Thr Cys Ser
    370                 375                 380

Ser Tyr Arg Gly Tyr Pro Glu Ala Glu Val Phe Trp Gln Asp Gly Gln
385                 390                 395                 400

Gly Val Pro Leu Thr Gly Asn Val Thr Thr Ser Gln Met Ala Asn Glu
                405                 410                 415

Gln Gly Leu Phe Asp Val His Ser Val Leu Arg Val Val Leu Gly Ala
            420                 425                 430

Asn Gly Thr Tyr Ser Cys Leu Val Arg Asn Pro Val Leu Gln Gln Asp
        435                 440                 445

Ala His Gly Ser Val Thr Ile Thr Gly Gln Pro Met Thr Phe Pro Pro
    450                 455                 460

Glu Ala Leu Trp Val Thr Val Gly Leu Ser Val Cys Leu Ile Ala Leu
465                 470                 475                 480

Leu Val Ala Leu Ala Phe Val Cys Trp Arg Lys Ile Lys Gln Ser Cys
                485                 490                 495

Glu Glu Glu Asn Ala Gly Ala Glu Asp Gln Asp Gly Glu Gly Glu Gly
            500                 505                 510

Ser Lys Thr Ala Leu Gln Pro Leu Lys His Ser Asp Ser Lys Glu Asp
        515                 520                 525

Asp Gly Gln Glu Ile Ala
    530

<210> SEQ ID NO 25
<211> LENGTH: 350
<212> TYPE: PRT
<213> ORGANISM: Homo sapiens

<400> SEQUENCE: 25

Met Ala Ser Phe Leu Ala Phe Leu Leu Leu Asn Phe Arg Val Cys Leu
  1               5                  10                  15

Leu Leu Leu Gln Leu Leu Met Pro His Ser Ala Gln Phe Ser Val Leu
                20                  25                  30
```

-continued

```
Gly Pro Ser Gly Pro Ile Leu Ala Met Val Gly Glu Asp Ala Asp Leu
        35                  40                  45

Pro Cys His Leu Phe Pro Thr Met Ser Ala Glu Thr Met Glu Leu Lys
        50                  55                  60

Trp Val Ser Ser Ser Leu Arg Gln Val Val Asn Val Tyr Ala Asp Gly
 65                  70                  75                  80

Lys Glu Val Glu Asp Arg Gln Ser Ala Pro Tyr Arg Gly Arg Thr Ser
                85                  90                  95

Ile Leu Arg Asp Gly Ile Thr Ala Gly Lys Ala Ala Phe Arg Ile His
            100                 105                 110

Asn Val Thr Gly Ser Asp Arg Trp Lys Tyr Leu Cys Tyr Phe Gln Asp
            115                 120                 125

Gly Asp Phe Tyr Glu Lys Ala Leu Val Glu Leu Lys Val Ala Ala Leu
    130                 135                 140

Gly Ser Asp Leu His Val Asp Val Lys Gly Tyr Lys Asp Gly Gly Ile
145                 150                 155                 160

His Leu Glu Cys Arg Ser Thr Gly Trp Tyr Pro Gln Pro Gln Ile Gln
                165                 170                 175

Trp Ser Asn Asn Lys Gly Glu Asn Ile Pro Thr Val Glu Ala Pro Val
            180                 185                 190

Val Ala Asp Gly Val Gly Leu Tyr Ala Val Ala Ala Ser Val Ile Met
            195                 200                 205

Arg Gly Ser Ser Gly Glu Gly Val Ser Cys Thr Ile Arg Asn Ser Leu
    210                 215                 220

Leu Gly Leu Glu Lys Thr Ala Ser Ile Ser Ile Ala Arg Pro Phe Phe
225                 230                 235                 240

Arg Ser Ala Gln Arg Trp Ile Ala Ala Leu Ala Gly Thr Leu Pro Val
                245                 250                 255

Leu Leu Leu Leu Leu Gly Gly Ala Gly Tyr Phe Leu Trp Gln Gln Gln
            260                 265                 270

Glu Glu Lys Lys Thr Gln Phe Arg Lys Lys Arg Glu Gln Glu Leu
            275                 280                 285

Arg Glu Met Ala Trp Ser Thr Met Lys Gln Glu Gln Ser Thr Arg Val
    290                 295                 300

Lys Leu Leu Glu Glu Leu Arg Trp Arg Ser Ile Gln Tyr Ala Ser Arg
305                 310                 315                 320

Gly Glu Arg His Ser Ala Tyr Asn Glu Trp Lys Lys Ala Leu Phe Lys
                325                 330                 335

Pro Gly Glu Glu Met Leu Gln Met Arg Leu His Phe Val Lys
                340                 345                 350
```

NUCLEIC ACIDS ENCODING MEMBERS OF THE HUMAN B LYMPHOCYTE ACTIVATION ANTIGEN B7 FAMILY AND METHODS OF USING THE SAME

RELATED APPLICATIONS

This application claims priority to provisional patent applications U.S. Ser. No. 60/152,383, filed Sep. 3, 1999, U.S. Ser. No. 60/172,909, filed Dec. 21, 1999, and U.S. Ser. No. 60/183,578, filed Feb. 18, 2000, each of which are each incorporated herein by reference in their entireties.

FIELD OF THE INVENTION

The invention relates generally to polynucleotides and polypeptides encoded thereby, as well as vectors, antibodies and recombinant methods for producing the polypeptides and polynucleotides.

BACKGROUND OF THE INVENTION

The immune system of vertebrates is characterized by its ability to discriminate "self" from "non-self" and to mount an appropriate, selective response to pathogens and other potentially harmful agents. Cell types involved in immune responses include lymphocytes known as B cells and T cells. Interactions between B cells and T cells are important for the propagation of full immune responses.

T cells must be activated in order to effect an immune response. T cell activation is thought to require two signals: an antigen-specific signal and a signal that is not antigen-specific. T cells can become activated by binding to B cells, particularly B cells which are themselves activated.

B cell-mediated activation of T cells is thought to be mediated, at least in part, by B7 proteins, which are expressed on the surface of B cells. B7 proteins are members of the immunoglobulin superfamily. They bind to activated T lymphocytes and provide regulatory signals for T lymphocyte cell growth and activation. (See, e.g., "Immunobiology—The Immune System in Health and Disease", 1997, Third edition, chapter 7, Janeway, C. A. et al., eds., Garland Publishing Inc., New York.) Cell surface molecules on T cells which bind to B7 molecules include CTLA4 and CD28.

SUMMARY OF THE INVENTION

The present invention is based, in part, upon the discovery of BLAA polynucleotide sequences encoding novel members of the human B Lymphocyte Activation Antigen B7 family (henceforth "BLAA").

In one aspect, the present invention involves an isolated nucleic acid molecule encoding a BLAA. This nucleic acid molecule may be a nucleotide that encodes a polypeptide having a sequence that is at least 95% identical to SEQ ID NO:2 or SEQ ID NO:6. Alternatively, it may be the complement of such a nucleic acid molecule.

In another aspect, this invention involves an oligonucleotide that is less than 100 nucleotides in length and contains at least 6 contiguous nucleotides of SEQ ID NO:1, 3, 5, 7, 8, 9, 10, 11, or 12. This oligonucleotide contains at least 6 contiguous nucleotides of a complement of SEQ ID NO:1, 3, 5, 7, 8, 9, 10, 11, or 12.

Another aspect of this invention relates to a vector containing an isolated nucleic acid molecule encoding a BLAA, as described above. In one embodiment, this vector is an expression vector. In another embodiment, this vector contains a regulatory element that is operably linked to the isolated nucleic acid molecule.

A further aspect of this invention involves an isolated polypeptide that is at least 80% identical to a polypeptide having an amino acid sequence of SEQ ID NO:2, SEQ ID NO:4, or SEQ ID NO:6. In another embodiment of this aspect of the invention, the isolated polypeptide is at least 80% homologous to a fragment of a polypeptide having an amino acid sequence of SEQ ID NO:2, SEQ ID NO:4, or SEQ ID NO:6. In this embodiment, the fragment contains at least 6 contiguous amino acids of SEQ ID NO:2, SEQ ID NO:4, or SEQ ID NO:6. Other embodiments of this aspect of the invention require that the isolated polypeptides of the invention be at least 80% homologous to a derivative, analog, or homolog of a polypeptide having an amino acid sequence of SEQ ID NO:2, SEQ ID NO:4, or SEQ ID NO:6. Yet another embodiment involves an isolated polypeptide that is at least 80% identical to a naturally occurring allelic variant of a polypeptide having an amino acid sequence of SEQ ID NO:2, SEQ ID NO:4, or SEQ ID NO:6. This embodiment requires that the polypeptide be encoded by a nucleic acid molecule capable of hybridizing to a nucleic acid molecule of SEQ ID NO:1, SEQ ID NO:3, or SEQ ID NO:5, under stringent conditions.

Another embodiment of this invention involves an antibody that selectively binds to the polypeptide(s) described above. Further embodiments of this invention provide methods for (a) producing such polypeptide(s) by culturing a host cell under conditions in which the nucleic acid molecule is expressed; (b) detecting the presence of the polypeptide(s) in a sample by contacting the sample with a compound that selectively binds to the polypeptide(s) of the invention; and (c) modulating the activity of such polypeptide(s) by contacting a cell sample containing the polypeptide(s) of the instant invention with a compound that binds to the polypeptide(s) to modulate its activity.

Additionally, a method of detecting the presence of one of the nucleic acid molecules of this invention is also provided. This method involves contacting a sample with a compound that selectively binds to the polypeptide(s) of this invention and determining whether the compound bound to the polypeptide(s) is present in the sample.

Other embodiments of this invention include methods of treating or preventing immune response-associated disorders and therapeutic or prophylactic pharmaceutical compositions. Additionally, another aspect of this invention involves a kit containing therapeutically or prophylactically effective amounts of the pharmaceutical compositions provided for in the instant invention.

Another aspect of this invention involves the use of a therapeutic in the manufacture of a medicament for treating diseases associated with immune-response disorders. Another embodiment of this invention involves a method for screening for a modulator of activity, latency or predisposition to an immune response-associated disorder. In this embodiment, a test compound is administered to an animal at an increased risk for an immune response-associated disorder, measuring the expression of the polypeptide of the invention in the test animal, measuring polypeptide expression in a control animal, and comparing the expression in both animals.

Other embodiments of this invention include methods for determining the presence of or predisposition to a disease associate with altered levels of a BLAA polypeptide or a BLAA nucleic acid by measuring the amount of BLAA polypeptide or nucleic acid in a sample and comparing it to the amount present in a control sample. Yet other embodiments of this invention involve methods of treating a pathological state in a mammal by administering a BLAA polypeptide or a BLAA nucleic acid in amounts sufficient to alleviate the pathological state.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and are not intended to be limiting.

Other features and advantages of the invention will be apparent from the following detailed description and claims.

BRIEF DESCRIPTION OF THE DRAWINGS

FIG. 1 is a representation of a 2691 nucleotide human cDNA sequence (SEQ ID NO: 1), and an amino acid sequence of the encoded polypeptide (SEQ ID NO:2).

FIG. 2 is a representation of a 2885 nucleotide human cDNA sequence (SEQ ID NO: 3), and an amino acid sequence of the encoded polypeptide (SEQ ID NO:4).

FIG. 3 is a representation of a 2229 nucleotide human cDNA sequence (SEQ ID NO: 5), and an amino acid sequence of the encoded polypeptide (SEQ ID NO:6).

FIG. 4 shows the ClustalW Alignment of the BLAA polypeptide of SEQ ID NO: 6 as compared to several homologous B7 proteins and indicates the conserved regions by dark highlighting and conservative amino acid substitutions by lighter highlighting. In the alignment, "B7-1_Human" corresponds to SEQ ID NO:13, "Q28499_rhesus_B7-1" corresponds to SEQ ID NO:14, "B7-1_RABIT" corresponds to SEQ ID NO:15; "U57755_cat_B7-1" corresponds to SEQ ID NO:16, "B7-1_MOUSE" corresponds to SEQ ID NO:17, "AF157827_cat_B7-2" corresponds to SEQ ID NO:18, "aaf17927_dog_B7-2" corresponds to SEQ ID NO:19, "176088_pig_B7-2" corresponds to SEQ ID NO:20, "u04343_hu_B7-2" corresponds to SEQ ID NO:21, "P42082_mus_B7-2" corresponds to SEQ ID NO:22, "aac52336_mus_B7-2_alt.spl" corresponds to SEQ ID NO:23, "mz5020.protein" corresponds to SEQ ID NO:6, and "Q99420q99420_put_hum_B7-3" corresponds to SEQ ID NO:25.

DETAILED DESCRIPTION OF THE INVENTION

Figure 5:
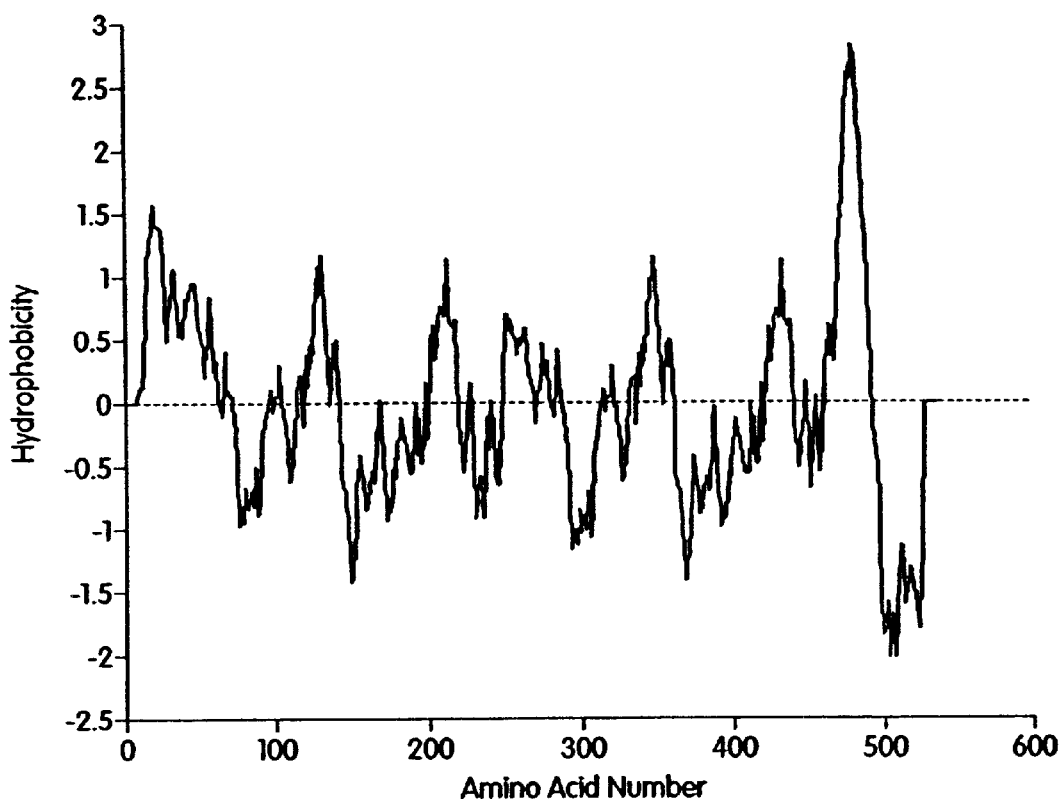
FIG. 5 depicts the hydrophobicity plot for the polypeptide of SEQ ID NO: 6.

The invention provides novel polynucleotides encoding polypeptides bearing sequence similarity to the B7 family of B lymphocyte antigens (BLAA). These cDNA sequences according to the invention, along with their encoded BLAA polypeptides are shown in FIGS. 1, 2 and 3.

The BLAA polypeptides are 20–25% identical and 40–45% similar to previously described members of the B7 family (i.e., B7-1 and B7-2). As discussed in detail below, several motifs of the BLAA polypeptides are highly conserved with B7 polypeptides. Additionally, comparable similarity to human, mouse, and bovine butyrophilin as well as human myelin oligodendrocyte glycoprotein (MOG) has been observed.

The polypeptides of this invention have two (SEQ ID NO: 2), three (SEQ ID NO: 4), or four (SEQ ID NO: 6) Ig-like domains, followed by a transmembrane domain and a 44 amino acid cytoplasmic domain. This is consistent with previously described members of the B7 protein family, which are known to be localized on the cell surface (see, e.g., Selvakumar et al., Immunogenetics 36:175–181 (1992) and Linsley et al., Protein Sci 3:1341–1343 (1994)).

As used herein, the term "human B lymphocyte activation antigen B7-like activity" encompasses binding to activated T lymphocytes and providing regulatory signals for T lymphocyte cell growth and activation.

Accordingly, the polypeptides of the instant invention are novel members of the B7 protein family. The nucleic acid molecules and polypeptides of the present invention can be used to modulate immune responses. As such, they are useful in potential therapeutic applications implicated in the treatment of infectious diseases, cancers, autoimmune disorders and complications associated with graft vs. host disease in organ transplantation, and/or in similar immune system pathologies and disorders. For example, a cDNA encoding a polypeptide of the instant invention may be useful in gene therapy. Alternatively, a BLAA polypeptide can be administered directly to treat immune disorders. The nucleic acids, polypeptides and antibodies of the instant invention may be further useful in diagnostic and therapeutic applications.

Figure 4:
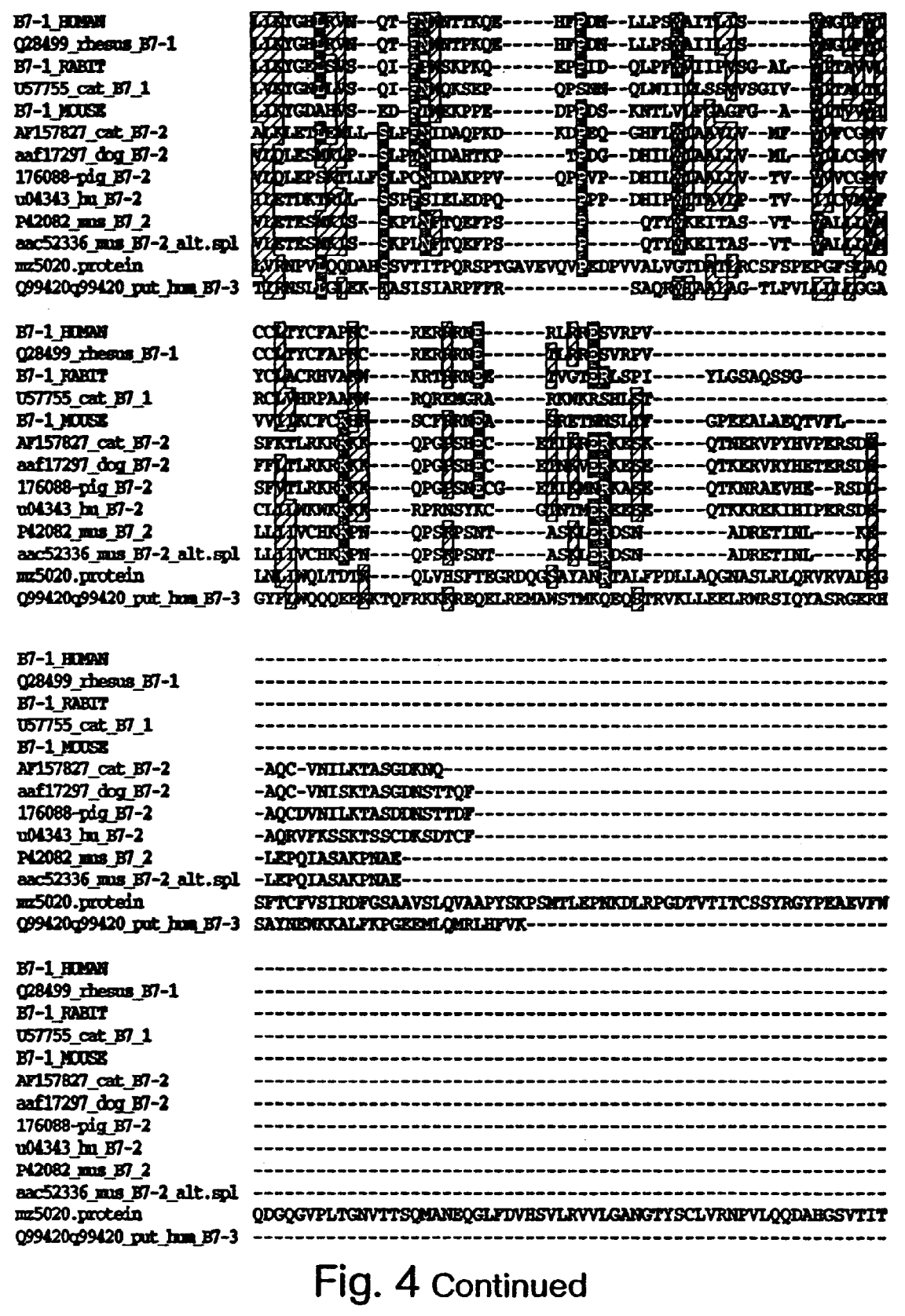

The BLAA polypeptides contain numerous regions and/or single amino acids that are conserved at corresponding position in other homologous B7 proteins. For example, FIG. 4 depicts the ClustalW alignment of the polypeptide of SEQ ID NO: 6. Conserved regions include, e.g., amino acids 16, 42, 46, 48, 50, 52, 59, 60, 63, 67–68, 75, 82, 89, 92–93, 107–109, 116, 118, 122, 134, 136, 138, 140, 143, 145, 152, 164–167, 170, 172–173, 187, 191, 194, 198, 210, 217, 223, 242 and 310. In addition, there are also regions with conservative amino acid substitutions as defined in the section "Conservative Mutations". By "conservative amino acid substitutions" is meant amino acids having similar side chains. Such substitutions are found, e.g., at amino acids 14, 25, 38, 65, 71, 79, 84, 106, 112, 114, 119, 123–124, 127–128, 142, 148–149, 161, 163, 171, 202, 212, 217, 221–223, 264, 266, 278, 283–284, 291, 305 and 335.

The BLAA polypeptides include hydrophilic and hydrophobic regions. As shown in FIG. 5, the polypeptide of SEQ ID NO: 6 contains both hydrophilic and hydrophobic portions. Hydrophobic regions include from about amino acid 1 to about amino acid 75; from about amino acid 110 to about amino acid 150; from about amino acid 200 to about amino acid 225; from about amino acid 250 to about amino acid 290; from about amino acid 310 to about amino acid 380; from about amino acid 420 to about amino acid 440; and from about amino acid 460 to about amino acid 500. Conversely, the hydrophilic regions include from about amino acid 75 to about amino acid 110; from about amino acid 150 to about amino acid 200; from about amino acid 225 to about amino acid 250; from about amino acid 290 to about amino acid 310; from about amino acid 380 to about amino acid 420; from about amino acid 440 to about amino acid 534. Accordingly, these regions are useful for designing epitopes or selecting antigens.

For ease of reference, the novel polynucleotide and polypeptide sequences of the present invention shall be referred to collectively as BLAA (for B Lymphocyte Activation Antigen). A summary of the BLAA nucleic acid and polypeptide sequences of the present invention is provided in Table 1.

TABLE 1

Sequences and Corresponding SEQ ID Numbers

| Sequence Identifier Number | Description |
| --- | --- |
| SEQ ID NO: 1 | 2691 nucleotide human cDNA sequence |
| SEQ ID NO: 2 | 340 amino acid polypeptide encoded by nucleotides 111–1130 (SEQ ID NO: 7) of SEQ ID NO: 1 |
| SEQ ID NO: 3 | 2885 nucleotide human cDNA sequence |
| SEQ ID NO: 4 | 441 amino acid polypeptide encoded by nucleotides 2–1324 (SEQ ID NO: 9) of SEQ ID NO: 3 |
| SEQ ID NO: 5 | 2229 nucleotide human cDNA sequence |
| SEQ ID NO: 6 | 534 amino acid polypeptide encoded by nucleotides 60–1661 (SEQ ID NO: 11) of SEQ ID NO: 5 |
| SEQ ID NO: 7 | Open reading frame extending from nucleotide 110 to 1130 of SEQ ID NO: 1 |
| SEQ ID NO: 8 | 3' non-translated region ("NTR") extending from nucleotide 1130 to 2691 of SEQ ID NO: 1 |
| SEQ ID NO: 9 | Open reading frame extending from nucleotide 2 to 1324 of SEQ ID NO: 3 |
| SEQ ID NO: 10 | 3' NTR extending from nucleotide 1325 to 2885 of SEQ ID NO: 3 |
| SEQ ID NO: 11 | Open reading frame extending from nucleotide 60 to 1661 of SEQ ID NO: 5 |
| SEQ ID NO: 12 | 3' NTR extending from nucleotide 1662 to 2229 of SEQ ID NO: 7 |

As used herein, "identical" residues correspond to those residues in a comparison between two sequences where the equivalent nucleotide base or amino acid residue in an alignment of two sequences is the same residue. Residues are "similar" when the comparisons between two sequences in an alignment show that residues in an equivalent position in a comparison are either the same amino acid or a conservatively substituted amino acid as defined below in the section "Conservative Mutations".

Nucleic Acids

One aspect of the invention pertains to isolated BLAA nucleic acid molecules that encode BLAA polypeptides or biologically active portions thereof. BLAA nucleic acid molecules also include nucleic acid fragments sufficient for use as hybridization probes to identify BLAA-encoding nucleic acids (e.g., BLAA mRNA) and fragments for use as PCR primers for the amplification or mutation of BLAA nucleic acid molecules. As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but preferably is double-stranded DNA.

"Probes" refer to nucleic acid sequences of variable length, preferably between at least about 10 nucleotides (nt), 100 nt, or as many as about, e.g., 6,000 nt, depending on use. Probes are used in the detection of identical, similar, or complementary nucleic acid sequences. Longer length probes are usually obtained from a natural or recombinant source and are highly specific and much slower to hybridize than oligomers. Probes may be single- or double-stranded and designed to have specificity in PCR, membrane-based hybridization technologies, or ELISA-like technologies.

An "isolated" nucleic acid molecule is one that is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated BLAA nucleic acid molecule can contain less than about 5 kb, 4 kb, 3 kb, 2 kb, 1 kb, 0.5 kb or 0.1 kb of nucleotide acid sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or of chemical precursors or other chemicals when chemically synthesized.

A nucleic acid molecule of the present invention, e.g., a nucleic acid molecule having a nucleotide sequence selected from the group consisting of SEQ ID NO: 1, SEQ ID NO: 3, SEQ ID NO: 5, SEQ ID NO: 7, SEQ ID NO: 8, SEQ ID NO: 9, SEQ ID NO: 10, SEQ ID NO: 11, and SEQ ID NO: 12, or a complement of any of these nucleotide sequences, can be isolated using standard molecular biology techniques and the sequence information provided herein. Using all or a portion of the nucleic acid sequences of SEQ ID NO: 1, 3, 5, 7, 8, 9, 10, 11, or 12 as a hybridization probe, BLAA molecules can be isolated using standard hybridization and cloning techniques (e.g., as described in Sambrook et al., (eds.), *MOLECULAR CLONING: A LABORATORY MANUAL* $2^{nd}$ Ed., Cold Spring Harbor Laboratory Press, Cold Spring Harbor, N.Y., 1989; and Ausubel, et al., (eds.), *CURRENT PROTOCOLS IN MOLECULAR BIOLOGY*, John Wiley & Sons, New York, N.Y., 1993.)

A nucleic acid of the invention can be amplified using cDNA, mRNA or, alternatively, genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to BLAA nucleotide sequences can be prepared by standard synthetic techniques, e.g., using an automated DNA synthesizer.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides comprise portions of a nucleic acid sequence having about 10 nt, 50 nt, or 100 nt in length, preferably about 15 nt to 30 nt in length. In one embodiment, an oligonucleotide comprising a nucleic acid molecule less than 100 nt in length would further comprise at lease 6 contiguous nucleotides of SEQ ID NO: 1, 3, 5, 7, 8, 9, 10, 11, or 12 or a complement thereof. Oligonucleotides may be chemically synthesized and may be used as probes.

In another embodiment, an isolated nucleic acid molecule of the invention comprises a nucleic acid molecule that is a complement of the nucleotide sequence shown in SEQ ID NO: 1, 3, 5, 7, 8, 9, 10, 11, or 12. A nucleic acid molecule that is complementary to the nucleotide sequence shown in SEQ ID NO: 1, 3, 5, 7, 8, 9, 10, 11, or 12 is one that is sufficiently complementary to the nucleotide sequence shown in SEQ ID NO: 1, 3, 5, 7, 8, 9, 10, 11, or 12, that it can hydrogen bond with little or no mismatches to the nucleotide sequence shown in SEQ ID NO: 1, 3, 5, 7, 8, 9, 10, 11, or 12, thereby forming a stable duplex.

As used herein, the term "complementary" refers to Watson-Crick or Hoogsteen base pairing between nucleotides units of a nucleic acid molecule, and the term "binding" means the physical or chemical interaction between two polypeptides or compounds or associated polypeptides or compounds or combinations thereof. Binding includes ionic, non-ionic, Van der Waals, hydrophobic interactions, etc. A physical interaction can be either direct or indirect. Indirect interactions may be through or due to the effects of another polypeptide or compound. Direct binding refers to interactions that do not take place through, or due to, the effect of another polypeptide or compound, but instead are without other substantial chemical intermediates.

Moreover, the nucleic acid molecule of the invention can comprise only a portion of the nucleic acid sequence of SEQ ID NO: 1, 3, 5, 7, 8, 9, 10, 11, or 12, e.g., a fragment that can be used as a probe or primer or a fragment encoding a biologically active portion of BLAA.

Fragments provided herein are defined as sequences of at least 6 (contiguous) nucleic acids or at least 4 (contiguous) amino acids, a length sufficient to allow for specific hybridization in the case of nucleic acids or for specific recognition of an epitope in the case of amino acids, respectively, and are at most some portion less than a full length sequence. Fragments may be derived from any contiguous portion of a nucleic acid or amino acid sequence of choice. Derivatives are nucleic acid sequences or amino acid sequences formed from the native compounds either directly or by modification or partial substitution. Analogs are nucleic acid sequences or amino acid sequences that have a structure similar to, but not identical to, the native compound but differs from it in respect to certain components or side chains. Analogs may be synthetic or from a different evolutionary origin and may have a similar or opposite metabolic activity compared to wild type. Homologs are nucleic acid sequences or amino acid sequences of a particular gene that are derived from different species.

Derivatives and analogs may be full length or other than full length, if the derivative or analog contains a modified nucleic acid or amino acid, as described below. Derivatives or analogs of the nucleic acids or proteins of the invention include, but are not limited to, molecules comprising regions that are substantially homologous to the nucleic acids or proteins of the invention, in various embodiments, by at least about 30%, 50%, 70%, 80%, or 95% identity (with a preferred identity of 80–95%) over a nucleic acid or amino acid sequence of identical size or when compared to an aligned sequence in which the alignment is done by a computer homology program known in the art, or whose encoding nucleic acid is capable of hybridizing to the complement of a sequence encoding the aforementioned proteins under stringent, moderately stringent, or low stringent conditions. See e.g. Ausubel, et al., CURRENT PROTOCOLS IN MOLECULAR BIOLOGY, John Wiley & Sons, New York, N.Y., 1993, and below.

A "homologous nucleic acid sequence" or "homologous amino acid sequence," or variations thereof, refer to sequences characterized by a homology at the nucleotide level or amino acid level as discussed above. Homologous nucleotide sequences encode those sequences coding for isoforms of a BLAA polypeptide. Isoforms can be expressed in different tissues of the same organism as a result of, for example, alternative splicing of RNA. Alternatively, isoforms can be encoded by different genes. In the present invention, homologous nucleotide sequences include nucleotide sequences encoding for a BLAA polypeptide of species other than humans, including, but not limited to, mammals, and thus can include, e.g., mouse, rat, rabbit, dog, cat cow, horse, and other organisms. Homologous nucleotide sequences also include, but are not limited to, naturally occurring allelic variations and mutations of the nucleotide sequences set forth herein. A homologous nucleotide sequence does not, however, include a nucleotide sequence encoding a human BLAA polypeptide. Homologous nucleic acid sequences include those nucleic acid sequences that encode conservative amino acid substitutions (see below) in SEQ ID NO: 2, SEQ ID NO: 4, or SEQ ID NO: 6, as well as a polypeptide having BLAA activity. Biological activities of the BLAA proteins are described below. A homologous amino acid sequence does not encode the amino acid sequence of a human BLAA polypeptide.

A BLAA polypeptide can be encoded by an open reading frame ("ORF") of a BLAA nucleic acid, as described herein. For example, the invention includes a nucleic acid sequence comprising the stretch of nucleic acid sequences of SEQ ID NO: 7, SEQ ID NO: 9, and SEQ ID NO: 11 that comprise the ORFs of the instant invention and encode a polypeptide of SEQ ID NO: 2, SEQ ID NO: 4, and SEQ ID NO: 6, respectively.

An "open reading frame" ("ORF") corresponds to a nucleotide sequence that can potentially be translated into a polypeptide. A stretch of nucleic acids comprising an ORF is uninterrupted by a stop codon. An ORF that represents the coding sequence for a full protein begins with an ATG "start" codon and terminates with one of the three "stop" codons, namely, TAA, TAG, or TGA. For the purposes of this invention, an ORF may be any part of a coding sequence, with or without a start codon, a stop codon, or both. For an ORF to be considered as a good candidate for coding for a bona fide cellular protein, a minimum size requirement is often set, for example, a stretch of DNA that would encode a protein of 50 amino acids or more.

In one embodiment, a 1020 base pair (bp) ORF (SEQ ID NO: 7) includes nucleotide 111 to nucleotide 1130 of SEQ ID NO: 1. This ORF can be translated into a 340 amino acid polypeptide according to SEQ ID NO: 2. In another embodiment, a 1323 bp ORF (SEQ ID NO: 9) includes nucleotide 2 to nucleotide 1324 of SEQ ID NO: 3. This ORF can be translated into a 441 amino acid polypeptide according to SEQ ID NO: 4. In another embodiment, a 1601 bp ORF (SEQ ID NO: 11) includes nucleotide 60 to nucleotide 1661 of SEQ ID NO: 5. This ORF could be translated into a 534 amino acid polypeptide according to SEQ ID NO: 6.

The nucleotide sequence determined from the cloning of the human BLAA gene allows for the generation of probes and primers designed for use in identifying and/or cloning BLAA homologues in other cell types, e.g. from other tissues, as well as BLAA homologues from other mammals. The probe/primer typically comprises substantially purified oligonucleotide. The oligonucleotide typically comprises a region of nucleotide sequence that hybridizes under stringent conditions to at least about 12, 25, 50, 100, 150, 200, 250, 300, 350 or 400 consecutive sense strand nucleotide sequence of SEQ ID NO: 1, 3, 5, 7, 8, 9, 10, 11, or 12; or an anti-sense strand nucleotide sequence of SEQ ID NO: 1, 3, 5, 7, 8, 9, 10, 11, or 12; or of a naturally occurring mutant of SEQ ID NO: 1, 3, 5, 7, 8, 9, 10, 11, or 12.

Probes based on a human BLAA nucleotide sequence can be used to detect transcripts or genomic sequences encoding the same or homologous proteins. In various embodiments, the probe further comprises a label group attached thereto, e.g. the label group can be a radioisotope, a fluorescent compound, an enzyme, or an enzyme co-factor. Such probes can be used as a part of a diagnostic test kit for identifying cells or tissue which misexpress a BLAA protein, such as by measuring a level of a BLAA-encoding nucleic acid in a sample of cells from a subject e.g., detecting BLAA mRNA levels or determining whether a genomic BLAA gene has been mutated or deleted.

"A polypeptide having a biologically active portion of BLAA" refers to polypeptides exhibiting activity similar, but not necessarily identical to, an activity of a polypeptide of the present invention, including mature forms, as measured in a particular biological assay, with or without dose dependency. A nucleic acid fragment encoding a "biologically active portion of BLAA" can be prepared by isolating a portion of SEQ ID NO: 1, 3, 5, 7, 9, or 11, that encodes a polypeptide having a BLAA biological activity (the biological activities of the BLAA proteins are described below), expressing the encoded portion of BLAA polypeptide (e.g., by recombinant expression in vitro) and assessing the activity of the encoded portion of BLAA.

BLAA Variants

The invention further encompasses nucleic acid molecules that differ from the nucleotide sequence shown in SEQ ID NO: 1, 3, 5, 7, 9, or 11, due to degeneracy of the genetic code and thus encode the same BLAA protein as that encoded by the nucleotide sequence shown in SEQ ID NO: 1, 3, 5, 7, 9, or 11. In another embodiment, an isolated nucleic acid molecule of the invention has a nucleotide sequence encoding a protein having an amino acid sequence shown in SEQ ID NO: 2, SEQ ID NO: 4 or SEQ ID NO: 6.

In addition to the human BLAA nucleotide sequence shown in SEQ ID NO: 1, 3, 5, 7, 9, or 11, it will be appreciated by those skilled in the art that DNA sequence polymorphisms that lead to changes in the amino acid sequences of BLAA may exist within a population (e.g., the human population). Such genetic polymorphism in the BLAA gene may exist among individuals within a population due to natural allelic variation. As used herein, the terms "gene" and "recombinant gene" refer to nucleic acid molecules comprising an open reading frame encoding a BLAA polypeptide, preferably a mammalian BLAA polypeptide. Such natural allelic variations can typically result in 1–5% variance in the nucleotide sequence of the BLAA gene. Any and all such nucleotide variations and resulting amino acid polymorphisms in BLAA that are the result of natural allelic variation and that do not alter the functional activity of BLAA are intended to be within the scope of the invention.

Moreover, nucleic acid molecules encoding BLAA polypeptides from other species, and thus that have a nucleotide sequence that differs from the human sequence of SEQ ID NO: 1, 3, 5, 7, 9, or 11, are intended to be within the scope of the invention. Nucleic acid molecules corresponding to natural allelic variants and homologues of the BLAA cDNAs of the invention can be isolated based on their homology to the human BLAA nucleic acids disclosed herein using the human cDNAs, or a portion thereof, as a hybridization probe according to standard hybridization techniques under stringent hybridization conditions. For example, a soluble human BLAA cDNA can be isolated based on its homology to human membrane-bound BLAA. Likewise, a membrane-bound human BLAA cDNA can be isolated based on its homology to soluble human BLAA.

Accordingly, in another embodiment, an isolated nucleic acid molecule of the invention is at least 6 nucleotides in length and hybridizes under stringent conditions to the nucleic acid molecule comprising the nucleotide sequence of SEQ ID NO: 1, 3, 5, 7, 8, 9, 10, 11, or 12. In another embodiment, the nucleic acid is at least 10, 25, 50, 100, 250, 500, 1000, 1500, 2000, or more nucleotides in length. In another embodiment, an isolated nucleic acid molecule of the invention hybridizes to the coding region, for example SEQ ID NO: 1, 3, 5, 7, 9, or 11. As used herein, the term "hybridizes under stringent conditions" is intended to describe conditions for hybridization and washing under which nucleotide sequences at least 60% homologous to each other typically remain hybridized to each other.

Homologs (i.e., nucleic acids encoding BLAA polypeptides derived from species other than human) or other related sequences (e.g., paralogs) can be obtained by low, moderate or high stringency hybridization with all or a portion of the particular human sequence as a probe using methods well known in the art for nucleic acid hybridization and cloning.

As used herein, the phrase "stringent hybridization conditions" refers to conditions under which a probe, primer or oligonucleotide will hybridize to its target sequence, but to no other sequences. Stringent conditions are sequence-dependent and will be different in different circumstances. Longer sequences hybridize specifically at higher temperatures than shorter sequences. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 nt to 50 nt) and at least about 60° C. for longer probes, primers and oligonucleotides. Stringent conditions may also be achieved with the addition of destabilizing agents, such as formamide.

Stringent conditions are known to those skilled in the art and can be found in Ausubel et al., (eds.), *CURRENT PROTOCOLS IN MOLECULAR BIOLOGY*, John Wiley & Sons, N.Y. (1989), 6.3.1–6.3.6. Preferably, the conditions are such that sequences at least about 65%, 70%, 75%, 85%, 90%, 95%, 98%, or 99% homologous to each other typically remain hybridized to each other. A non-limiting example of stringent hybridization conditions are hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C., followed by one or more washes in 0.2×SSC, 0.01% BSA at 50° C. An isolated nucleic acid molecule of the invention that hybridizes under stringent conditions to the sequence of SEQ ID NO: 1, 3, 5, 7, 8, 9, 10, 11, or 12, corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In a second embodiment, a nucleic acid sequence that is hybridizable to the nucleic acid molecule comprising the nucleotide sequence of SEQ ID NO: 1, 3, 5, 7, 8, 9, 10, 11, or 12, or fragments, analogs or derivatives thereof, under conditions of moderate stringency is provided. A non-limiting example of moderate stringency hybridization conditions are hybridization in 6×SSC, 5×Denhardt's solution, 0.5% SDS and 100 mg/ml denatured salmon sperm DNA at 55° C., followed by one or more washes in 1×SSC, 0.1% SDS at 37° C. Other conditions of moderate stringency that may be used are well-known in the art. See, e.g., Ausubel et al. (eds.), 1993, *CURRENT PROTOCOLS IN MOLECULAR BIOLOGY*, John Wiley & Sons, NY, and Kriegler, 1990, *GENE TRANSFER AND EXPRESSION, A LABORATORY MANUAL*, Stockton Press, NY.

In a third embodiment, a nucleic acid that is hybridizable to the nucleic acid molecule comprising the nucleotide sequence of SEQ ID NO: 1, 3, 5, 7, 8, 9, 10, 11, or 12, or fragments, analogs or derivatives thereof, under conditions of low stringency, is provided. A non-limiting example of low stringency hybridization conditions are hybridization in 35% formamide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2×SSC, 25 mM Tris-HCl (pH 7.4), 5 mM EDTA, and 0.1% SDS at 50° C. Other conditions of low stringency that may be used are well known in the art (e.g., as employed for cross-species hybridizations). See, e.g., Ausubel et al. (eds.), 1993, *CURRENT PROTOCOLS IN MOLECULAR BIOLOGY*, John Wiley & Sons, NY, and Kriegler, 1990, *GENE TRANSFER AND EXPRESSION, A LABORATORY MANUAL*, Stockton Press, NY; Shilo and Weinberg, 1981, *Proc Natl Acad Sci USA* 78: 6789–6792.

Conservative Mutations

In addition to naturally-occurring allelic variants of the BLAA sequence that may exist in the population, the skilled artisan will further appreciate that changes can be introduced by mutation into the nucleotide sequence of SEQ ID NO: 1, 3, 5, 7, 9, or 11, thereby leading to changes in the amino acid sequence of the encoded BLAA polypeptide, without altering the functional ability of the BLAA polypeptide. For example, nucleotide substitutions leading to amino acid substitutions at "non-essential" amino acid residues can be made in the sequence of SEQ ID NO: 1, 3, 5, 7, 9, or 11. A "non-essential" amino acid residue is a residue that can be altered from the wild-type sequence of BLAA without altering the biological activity, whereas an "essential" amino acid residue is required for biological activity. For example, amino acid residues that are conserved among the BLAA polypeptides of the present invention, are predicted to be particularly unamenable to alteration. (See FIG. 4 and discussion above).

In addition, amino acid residues that are conserved among family members of the BLAA polypeptides of the present invention, as indicated by the alignment presented in FIG. 4, and as described above, are also predicted to be particularly unamenable to alteration. Other amino acid residues, however, (e.g., those that are not conserved or only semi-conserved among members of the BLAA polypeptides) may not be essential for activity and thus are likely to be amenable to alteration.

Another aspect of the invention pertains to nucleic acid molecules encoding BLAA polypeptides that contain changes in amino acid residues that are not essential for activity. Such BLAA polypeptides differ in amino acid sequence from SEQ ID NO: 2, SEQ ID NO: 4, or SEQ ID NO: 6, yet retain biological activity. In one embodiment, the isolated nucleic acid molecule comprises a nucleotide sequence encoding a polypeptide, wherein the polypeptide comprises an amino acid sequence at least about 45% homologous to the amino acid sequence of SEQ ID NO: 2, SEQ ID NO: 4, or SEQ ID NO: 6. Preferably, the polypeptide encoded by the nucleic acid molecule is at least about 60% homologous to SEQ ID NO: 2, SEQ ID NO: 4, or SEQ ID NO: 6, more preferably at least about 70% homologous to SEQ ID NO: 2, SEQ ID NO: 4, or SEQ ID NO: 6, still more preferably at least about 80% homologous to SEQ ID NO: 2, SEQ ID NO: 4, or SEQ ID NO: 6, or SEQ ID NO: 6, even more preferably at least about 90% homologous to SEQ ID NO: 2, SEQ ID NO: 4, or SEQ ID NO: 6, and most preferably at least about 95% homologous to SEQ ID NO: 2, SEQ ID NO: 4, or SEQ ID NO: 6.

An isolated nucleic acid molecule encoding a BLAA polypeptide homologous to the polypeptide of SEQ ID NO: 2, SEQ ID NO: 4, or SEQ ID NO: 6 can be created by introducing one or more nucleotide substitutions, additions or deletions into the nucleotide sequence of SEQ ID NO: 1, 3, 5, 7, 9, or 11 such that one or more amino acid substitutions, additions or deletions are introduced into the encoded polypeptide.

Mutations can be introduced into SEQ ID NO: 1, 3, 5, 7, 9, or 11 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in BLAA is replaced with another amino acid residue from the same side chain family. Alternatively, in another embodiment, mutations can be introduced randomly along all or part of a BLAA coding sequence, such as by saturation mutagenesis, and the resultant mutants can be screened for BLAA biological activity to identify mutants that retain activity. Following mutagenesis of SEQ ID NO: 1, 3, 5, 7, 9, or 11, the encoded polypeptide can be expressed by any recombinant technology known in the art and the activity of the polypeptide can be determined.

In one embodiment, a mutant BLAA polypeptide can be assayed for (1) the ability to form protein:protein interactions with other BLAA polypeptides, other cell-surface proteins, or biologically active portions thereof, (2) complex formation between a mutant BLAA polypeptide and a BLAA ligand, e.g., CTLA4; (3) the ability of a mutant BLAA polypeptide to bind to an intracellular target protein or biologically active portion thereof (e.g. avidin proteins).

In yet another embodiment, a mutant BLAA can be assayed for the ability to perform immunoglobulin superfamily member activities, such as, (i) complex formation between a BLAA polypeptide and activated T lymphocytes; (ii) interaction of a BLAA polypeptide with a protein having substantial homology to the human B lymphocyte activation antigen B7 family of proteins; (iii) interaction of a BLAA polypeptide with a human B lymphocyte activation antigen B7 family member protein; and (iv) interaction of a BLAA polypeptide with other proteins. In yet another embodiment, a BLAA activity is at least one or more of the following activities: (i) modulation of immunoglobulin superfamily-related protein activity; (ii) regulation of T lymphocyte growth; and (iii) regulation of T lymphocyte activation.

Antisense

Another aspect of the invention pertains to isolated antisense nucleic acid molecules that are hybridizable to or complementary to the nucleic acid molecule comprising the nucleotide sequence of SEQ ID NO: 1, 3, 5, 7, 8, 9, 10, 11, or 12, or fragments, analogs or derivatives thereof. An "antisense" nucleic acid comprises a nucleotide sequence that is complementary to a "sense" nucleic acid encoding a protein, e.g., complementary to the coding strand of a double-stranded cDNA molecule or complementary to an mRNA sequence. In specific aspects, antisense nucleic acid molecules are provided that comprise a sequence complementary to at least about 10, 25, 50, 100, 250 or 500 nucleotides or an entire BLAA coding strand, or to only a portion thereof. Nucleic acid molecules encoding fragments, homologs, derivatives and analogs of a BLAA polypeptide of SEQ ID NO: 2, SEQ ID NO: 4, or SEQ ID NO: 6 or antisense nucleic acids complementary to a BLAA nucleic acid sequence of SEQ ID NO: 1, 3, 5, 7, 8, 9, 10, 11, or 12, are additionally provided.

In one embodiment, an antisense nucleic acid molecule is antisense to a "coding region" of the coding strand of a nucleotide sequence encoding BLAA. The term "coding region" refers to the region of the nucleotide sequence comprising codons which are translated into amino acid residues (e.g., the coding region of human BLAA corresponds to nucleotides 111–1130 of SEQ ID NO: 1 (SEQ ID NO: 7), nucleotides 2–1324 of SEQ ID NO: 3 (SEQ ID NO: 9), or nucleotides 60–1601 of SEQ ID NO: 5 (SEQ ID NO: 11)). In another embodiment, the antisense nucleic acid molecule is antisense to a "noncoding region" of the coding strand of a nucleotide sequence encoding BLAA. The term "noncoding region" refers to 5' and 3' sequences which flank the coding region that are not translated into amino acids (i.e., also referred to as 5' and 3' untranslated regions). Examples or "noncoding regions" include the non-translated regions ("NTRs") of SEQ ID NO: 8, SEQ ID NO: 10, and SEQ ID NO: 12.

Given the coding strand sequences encoding BLAA disclosed herein (e.g., SEQ ID NO: 5, SEQ ID NO: 7, and SEQ ID NO: 9), antisense nucleic acids of the invention can be designed according to the rules of Watson and Crick or Hoogsteen base pairing. The antisense nucleic acid molecule can be complementary to the entire coding region of BLAA mRNA, but more preferably is an oligonucleotide that is antisense to only a portion of the coding or noncoding region of BLAA mRNA. For example, the antisense oligonucleotide can be complementary to the region surrounding the translation start site of BLAA mRNA. An antisense oligonucleotide can be, for example, about 5, 10, 15, 20, 25, 30, 35, 40, 45 or 50 nucleotides in length. An antisense nucleic acid of the invention can be constructed using chemical synthesis or enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used.

Examples of modified nucleotides that can be used to generate the antisense nucleic acid include: 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a BLAA polypeptide to thereby inhibit expression of the protein, e.g., by inhibiting transcription and/or translation. The hybridization can be by conventional nucleotide complementarity to form a stable duplex, or, for example, in the case of an antisense nucleic acid molecule that binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids Res* 15: 6625–6641). The antisense nucleic acid molecule can also comprise a 2'-o-methylribonucleotide (Inoue et al. (1987) *Nucleic Acids Res* 15: 6131–6148) or a chimeric RNA-DNA analogue (Inoue et al. (1987) *FEBS Lett* 215: 327–330).

Ribozymes and PNA Moieties

Nucleic acid modifications include, by way of nonlimiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject.

In one embodiment, an antisense nucleic acid of the invention is a ribozyme. Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave BLAA mRNA transcripts to thereby inhibit translation of BLAA mRNA. A ribozyme having specificity for a BLAA-encoding nucleic acid can be designed based upon the nucleotide sequence of a BLAA cDNA disclosed herein (i.e., SEQ ID NO: 1, 3, 5, 7, 9, or 11). For example, a derivative of a Tetrahymena L-19 IVS RNA can be constructed in which the nucleotide sequence of the active site is complementary to the nucleotide sequence to be cleaved in a BLAA-encoding mRNA. See, e.g., Cech et al. U.S. Pat. No. 4,987,071; and Cech et al. U.S. Pat. No. 5,116,742. Alternatively, BLAA mRNA can be used to select a catalytic RNA having a specific ribonuclease activity from a pool of RNA molecules. See, e.g., Bartel et al., (1993) *Science* 261:1411–1418.

Alternatively, BLAA gene expression can be inhibited by targeting nucleotide sequences complementary to the regulatory region of the BLAA (e.g., the BLAA promoter and/or enhancers) to form triple helical structures that prevent transcription of the BLAA gene in target cells. See generally, Helene. (1991) *Anticancer Drug Des*. 6: 569–84; Helene. et al. (1992) *Ann. N.Y. Acad. Sci*. 660:27–36; and Maher (1992) *Bioassays* 14: 807–15.

In various embodiments, the nucleic acids of BLAA can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorg Med Chem* 4: 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) above; Perry-O'Keefe et al. (1996) *PNAS* 93: 14670–675.

PNAs of BLAA can be used in therapeutic and diagnostic applications. For example, PNAs can be used as antisense or antigene agents for sequence-specific modulation of gene expression by, e.g., inducing transcription or translation arrest or inhibiting replication. PNAs of BLAA can also be used, e.g., in the analysis of single base pair mutations in a gene by, e.g., PNA directed PCR clamping; as artificial restriction enzymes when used in combination with other enzymes, e.g., S1 nucleases (Hyrup B. (1996) above); or as probes or primers for DNA sequence and hybridization (Hyrup et al. (1996), above; Perry-O'Keefe (1996), above).

In another embodiment, PNAs of BLAA can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of BLAA can be generated that may combine the advantageous properties of PNA and DNA. Such chimeras allow DNA recognition enzymes, e.g., RNase H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996) above). The synthesis of PNA-DNA chimeras can be performed as described in Hyrup (1996) above and Finn et al. (1996) *Nucl Acids Res* 24: 3357–63. For example, a DNA chain can be synthesized on a solid support using standard phosphoramidite coupling chemistry, and modified nucleoside analogs, e.g., 5'-(4-methoxytrityl)amino-5'-deoxy-thymidine phosphoramidite, can be used between the PNA and the 5' end of DNA (Mag et al. (1989) *Nucl Acid Res* 17: 5973–88). PNA monomers are then coupled in a stepwise manner to produce a chimeric molecule with a 5' PNA segment and a 3' DNA segment (Finn et al. (1996) above). Alternatively, chimeric molecules can be synthesized with a 5' DNA segment and a 3' PNA segment. See, Petersen et al. (1975) *Bioorg Med Chem Lett* 5: 1119–11124.

In other embodiments, the oligonucleotide may include other appended groups such as peptides (e.g., for targeting host cell receptors in vivo), or agents facilitating transport across the cell membrane (see, e.g., Letsinger et al., 1989, *Proc. Natl. Acad. Sci. USA*. 86:6553–6556; Lemaitre et al., 1987, *Proc. Natl. Acad. Sci*. 84:648–652; PCT Publication No. WO88/09810) or the blood-brain barrier (see, e.g., PCT Publication No. WO89/10134). In addition, oligonucleotides can be modified with hybridization triggered cleavage agents (See, e.g., Krol et al., 1988, *BioTechniques* 6:958–976) or intercalating agents. (See, e.g., Zon, 1988, *Pharm. Res*. 5: 539–549). To this end, the oligonucleotide may be conjugated to another molecule, e.g., a peptide, a hybridization triggered cross-linking agent, a transport agent, a hybridization-triggered cleavage agent, etc.

BLAA Polypeptides

As used herein, the terms "protein" and "polypeptide" are intended to be interchangeable. The novel polypeptides of the invention include the BLAA polypeptides whose sequence is provided in SEQ ID NO: 2, SEQ ID NO: 4, or SEQ ID NO: 6. The invention also includes mutant or variant polypeptides any of whose residues may be changed from the corresponding residue shown in SEQ ID NO: 2, SEQ ID NO: 4, or SEQ ID NO: 6 while still encoding a polypeptide that maintains its BLAA activities and physiological functions, or a functional fragment thereof. In the mutant or variant protein, up to 20% or more of the residues may be so changed.

In general, an BLAA variant that preserves BLAA-like function includes any variant in which residues at a particular position in the sequence have been substituted by other amino acids, and further include the possibility of inserting an additional residue or residues between two residues of the parent protein as well as the possibility of deleting one or more residues from the parent sequence. Any amino acid substitution, insertion, or deletion is encompassed by the invention. In favorable circumstances, the substitution is a conservative substitution as defined above.

One aspect of the invention pertains to isolated BLAA polypeptides, and biologically active portions thereof, or derivatives, fragments, analogs or homologs thereof. Also provided are polypeptide fragments suitable for use as immunogens to raise anti-BLAA antibodies. In one embodiment, native BLAA polypeptides can be isolated from cells or tissue sources by an appropriate purification scheme using standard protein purification techniques. In another embodiment, BLAA polypeptides are produced by recombinant DNA techniques. Alternative to recombinant expression, a BLAA protein or polypeptide can be synthesized chemically using standard peptide synthesis techniques.

An "isolated" or "purified" polypeptide or biologically active portion thereof is substantially free of cellular material or other contaminating proteins or polypeptides from the cell or tissue source from which the BLAA polypeptide is derived, or substantially free from chemical precursors or other chemicals when chemically synthesized. The language "substantially free of cellular material" includes preparations of BLAA polypeptide in which the polypeptide is separated from cellular components of the cells from which it is isolated or recombinantly produced. In one embodiment, the language "substantially free of cellular material" includes preparations of BLAA polypeptide having less than about 30% (by dry weight) of non-BLAA protein (also referred to herein as a "contaminating protein"), more preferably less than about 20% of non-BLAA protein, still more preferably less than about 10% of non-BLAA protein, and most preferably less than about 5% non-BLAA protein. When the BLAA polypeptide or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of BLAA polypeptide in which the polypeptide is separated from chemical precursors or other chemicals that are involved in the synthesis of the polypeptide. In one embodiment, the language "substantially free of chemical precursors or other chemicals" includes preparations of BLAA polypeptide having less than about 30% (by dry weight) of chemical precursors or non-BLAA chemical, more preferably less than about 20% chemical precursors or non-BLAA chemicals, still more preferably less than about 10% chemical precursors or non-BLAA chemicals, and most preferably less than about 5% chemical precursors or non-BLAA chemicals.

Biologically active portions of a BLAA polypeptide include peptides comprising amino acid sequences sufficiently homologous to or derived from the amino acid sequence of the BLAA polypeptides, e.g., the amino acid sequence shown in SEQ ID NO: 2, SEQ ID NO: 4, or SEQ ID NO: 6, that include fewer amino acids than the full length BLAA polypeptides, and exhibit at least one activity of a BLAA polypeptide. Typically, biologically active portions comprise a domain or motif with at least one activity of the BLAA polypeptide. A biologically active portion of a BLAA polypeptide can be a polypeptide which is, for example, 10, 25, 50, 100 or more amino acids in length.

The polypeptide disclosed in SEQ ID NO: 2 has two Ig-like domains, followed by a transmembrane domain and a 44 amino acid cytoplasmic domain. The polypeptide disclosed in SEQ ID NO: 4 has three Ig-like domains, followed by a transmembrane domain and a 44 amino acid cytoplasmic domain. The polypeptide disclosed in SEQ ID NO: 6 has four Ig-like domains, followed by a transmembrane domain and a 44 amino acid cytoplasmic domain. Its hydrophobicity plot analysis is shown in FIG. 5.

In an embodiment, the BLAA polypeptide has an amino acid sequence shown in SEQ ID NO: 2, SEQ ID NO: 4, or SEQ ID NO: 6. In other embodiments, the BLAA polypeptide is substantially homologous to SEQ ID NO: 2, SEQ ID NO: 4, or SEQ ID NO: 6 and retains the functional activity of the polypeptide of SEQ ID NO: 2, SEQ ID NO: 4, or SEQ ID NO: 6, yet differs in amino acid sequence due to natural allelic variation or mutagenesis, as described in detail below. Accordingly, in another embodiment, the BLAA polypeptide is a polypeptide that comprises an amino acid sequence at least about 45% homologous to the amino acid sequence of SEQ ID NO: 2, SEQ ID NO: 4, or SEQ ID NO: 6 and retains the functional activity of the BLAA polypeptides of SEQ ID NO: 2, SEQ ID NO: 4, or SEQ ID NO: 6.

Determining Homology Between Two or More Sequences

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i e., as used herein amino acid or nucleic acid "homology" is equivalent to amino acid or nucleic acid "identity").

The nucleic acid sequence homology may be determined as the degree of identity between two sequences. The homology may be determined using computer programs known in the art, such as GAP software provided in the GCG program package. See, Needleman and Wunsch 1970 *J Mol Biol* 48: 443–453. Using GCG GAP software with the following settings for nucleic acid sequence comparison: GAP creation penalty of 5.0 and GAP extension penalty of 0.3, the coding region of the analogous nucleic acid sequences referred to above exhibits a degree of identity preferably of at least 70%, 75%, 80%, 85%, 90%, 95%, 98%, or 99%, with the CDS (encoding) part of the DNA sequence shown in SEQ ID NO: 1, 3, 5, 7, 9, or 11.

The term "sequence identity" refers to the degree to which two polynucleotide or polypeptide sequences are identical on a residue-by-residue basis over a particular region of comparison. The term "percentage of sequence identity" is calculated by comparing two optimally aligned sequences over that region of comparison, determining the number of positions at which the identical nucleic acid base (e.g., A, T, C, G, U, or I, in the case of nucleic acids) occurs in both sequences to yield the number of matched positions, dividing the number of matched positions by the total number of positions in the region of comparison (i e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison region.

Chimeric and Fusion Proteins

The invention also provides for BLAA chimeric or fusion proteins. As used herein, a BLAA "chimeric protein" or "fusion protein" comprises a BLAA polypeptide operatively linked to a non-BLAA polypeptide. A "BLAA polypeptide" refers to a polypeptide having an amino acid sequence corresponding to BLAA, whereas a "non-BLAA polypeptide" refers to a polypeptide having an amino acid sequence corresponding to a protein that is not substantially homologous to the BLAA polypeptide, e.g., a protein that is different from the BLAA polypeptide and that is derived from the same or a different organism. Within a BLAA fusion protein the BLAA polypeptide can correspond to all or a portion of a BLAA polypeptide. In one embodiment, a BLAA fusion protein comprises at least one biologically active portion of a BLAA protein. In another embodiment, a BLAA fusion protein comprises at least two biologically active portions of a BLAA polypeptide. In yet another embodiment, a BLAA fusion protein comprises at least three biologically active portions of a BLAA polypeptide. Within the fusion protein, the term "operatively linked" is intended to indicate that the BLAA polypeptide and the non-BLAA polypeptide are fused in-frame to each other. The non-BLAA polypeptide can be fused to the N-terminus or C-terminus of the BLAA polypeptide.

Such fusion proteins can be further utilized in screening assays for compounds which modulate BLAA activity (such assays are described in detail below).

In one embodiment, the fusion protein is a GST-BLAA fusion protein in which the BLAA sequences are fused to the C-terminus of the GST (i.e., glutathione S-transferase) sequences. Such fusion proteins can facilitate the purification of recombinant BLAA.

In another embodiment, the fusion protein is a BLAA polypeptide containing a heterologous signal sequence at it's N-terminus. For example, the nature BLAA signal sequence (e.g., about amino acids 1 to 26 of SEQ ID NO: 2, SEQ ID NO: 4, or SEQ ID NO: 6) can be removed and replaced with a signal sequence from another protein. In certain host cells (e.g., mammalian host cells), expression and/or secretion of BLAA can be increased through use of a heterologous signal sequence.

In yet another embodiment, the fusion protein is a BLAA-immunoglobulin fusion protein in which the BLAA sequences are fused to sequences derived from a member of the immunoglobulin protein family. The BLAA-immunoglobulin fusion proteins of the invention can be incorporated into pharmaceutical compositions and administered to a subject to inhibit an interaction between a BLAA ligand and a BLAA protein on the surface of a cell, to thereby suppress BLAA-mediated signal transduction in vivo. The BLAA-immunoglobulin fusion proteins can be used to affect the bioavailability of a BLAA cognate ligand. Inhibition of the BLAA ligand/BLAA interaction may be useful therapeutically for both the treatment of immune response-associated disorders. Moreover, the BLAA-immunoglobulin fusion proteins of the invention can be used as immunogens to produce anti-BLAA antibodies in a subject, to purify BLAA ligands, and in screening assays to identify molecules that inhibit the interaction of BLAA with a BLAA ligand.

A BLAA chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended terimini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (eds.) *CURRENT PROTOCOLS IN MOLECULAR BIOLOGY*, John Wiley & Sons, 1992). Moreover, many expression vectors are commercially available that already encode a fusion moiety (e.g., a GST polypeptide). A BLAA-encoding nucleic acid can be cloned into such an expression vector such that the fusion moiety is linked in-frame to the BLAA polypeptide.

BLAA Agonists and Antagonists

The present invention also pertains to variants of the BLAA polypeptides that function as either BLAA agonists (mimetics) or as BLAA antagonists. Variants of the BLAA polypeptide can be generated by mutagenesis, e.g., discrete point mutation or truncation of the BLAA polypeptide. An agonist of the BLAA polypeptide can retain substantially the same, or a subset of, the biological activities of the naturally occurring form of the BLAA polypeptide. An antagonist of the BLAA polypeptide can inhibit one or more of the activities of the naturally occurring form of the BLAA polypeptide by, for example, competitively binding to a downstream or upstream member of a cellular signaling cascade which includes the BLAA polypeptide. Thus, specific biological effects can be elicited by treatment with a variant of limited function. In one embodiment, treatment of a subject with a variant having a subset of the biological activities of the naturally occurring form of the polypeptide has fewer side effects in a subject relative to treatment with the naturally occurring form of the BLAA polypeptides.

Variants of the BLAA polypeptide that function as either BLAA agonists (mimetics) or as BLAA antagonists can be identified by screening combinatorial libraries of mutants, e.g., truncation mutants, of the BLAA polypeptide for BLAA polypeptide agonist or antagonist activity. In one embodiment, a variegated library of BLAA variants is generated by combinatorial mutagenesis at the nucleic acid level and is encoded by a variegated gene library. A variegated library of BLAA variants can be produced by, for example, enzymatically ligating a mixture of synthetic oligonucleotides into gene sequences such that a degenerate set of potential BLAA sequences is expressible as individual polypeptides, or alternatively, as a set of larger fusion proteins (e.g., for phage display) containing the set of BLAA sequences therein. There are a variety of methods which can be used to produce libraries of potential BLAA variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential BLAA sequences. Methods for synthesizing degenerate oligonucleotides are known in the art (see, e.g., Narang (1983) *Tetrahedron* 39:3; Itakura et al. (1984) *Annu Rev Biochem* 53:323; Itakura et al. (1984) *Science* 198:1056; Ike et al. (1983) *Nucl Acid Res* 11:477.

Polypeptide Libraries

In addition, libraries of fragments of the BLAA protein coding sequence can be used to generate a variegated population of BLAA fragments for screening and subsequent selection of variants of a BLAA polypeptide. In one embodiment, a library of coding sequence fragments can be generated by treating a double stranded PCR fragment of a BLAA coding sequence with a nuclease under conditions wherein nicking occurs only about once per molecule, denaturing the double stranded DNA, renaturing the DNA to form double stranded DNA that can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of a BLAA polypeptide.

Several techniques are known in the art for screening gene products of combinatorial libraries made by point mutations or truncation, and for screening eDNA libraries for gene products having a selected property. Such techniques are adaptable for rapid screening of the gene libraries generated by the combinatorial mutagenesis of a BLAA polypeptide. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recrusive ensemble mutagenesis (REM), a new technique that enhances the frequency of functional mutants in the libraries, can be used in combination with the screening assays to identify BLAA variants (Arkin and Yourvan (1992) *PNAS* 89:7811–7815; Delgrave et al. (1993) *Protein Engineering* 6:327–331).

Anti-BLAA Antibodies

The invention encompasses antibodies and antibody fragments, such as $F_{ab}$ or $(F_{ab})_2$, that bind immunospecifically to any of the polypeptides of the invention.

An isolated BLAA polypeptide, or a portion or fragment thereof, can be used as an immunogen to generate antibodies that bind BLAA using standard techniques for polyclonal and monoclonal antibody preparation. The full-length BLAA polypeptide can be used or, alternatively, the invention provides antigenic peptide fragments of BLAA for use as immunogens. The antigenic peptide of BLAA comprises at least 4 amino acid residues of the amino acid sequence shown in SEQ ID NO: 2, SEQ ID NO: 4, or SEQ ID NO: 6 and encompasses an epitope of BLAA such that an antibody raised against the peptide forms a specific immune complex with BLAA. Preferably, the antigenic peptide comprises at least 6, 8, 10, 15, 20, or 30 amino acid residues. Longer antigenic peptides are sometimes preferable over shorter antigenic peptides, depending on use and according to methods well known to someone skilled in the art.

In certain embodiments of the invention, at least one epitope encompassed by the antigenic peptide is a region of BLAA that is located on the surface of the polypeptide, e.g., a hydrophilic region. A hydrophobicity analysis of the human BLAA polypeptide sequence of SEQ ID NO:6, shown in FIG. 5, indicates that the hydrophilic regions include from about amino acid 75 to about amino acid 110; from about amino acid 150 to about amino acid 200; from about amino acid 225 to about amino acid 250; from about amino acid 290 to about amino acid 310; from about amino acid 380 to about amino acid 420; and from about amino acid 440 to about amino acid 534. These regions are likely to encode surface residues useful for targeting antibody production. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods, 1981, *Proc. Nat. Acad. Sci. USA* 78: 3824–3828; Kyte and Doolittle 1982, *J. Mol. Biol.* 157: 105–142, each reference is incorporated herein by reference in their entirety.

As disclosed herein, BLAA polypeptide sequence of SEQ ID NO: 2, SEQ ID NO: 4, or SEQ ID NO: 6, or derivatives, fragments, analogs or homologs thereof, may be utilized as immunogens in the generation of antibodies that immunospecifically-bind these protein components. The term "antibody" as used herein refers to immunoglobulin molecules and immunologically active portions of immunoglobulin molecules, i.e., molecules that contain an antigen binding site that specifically binds (immunoreacts with) an antigen, such as BLAA. Such antibodies include, but are not limited to, polyclonal, monoclonal, chimeric, single chain, $F_{ab}$ and $F_{(ab')2}$ fragments, and an $F_{ab}$ expression library. In a specific embodiment, antibodies to human BLAA polypeptides are disclosed. Various procedures known within the art may be used for the production of polyclonal or monoclonal antibodies to a BLAA polypeptide sequence of SEQ ID NO: 2, SEQ ID NO: 4, or SEQ ID NO: 6, or derivative, fragment, analog or homolog thereof. Some of these proteins are discussed below.

For the production of polyclonal antibodies, various suitable host animals (e.g., rabbit, goat, mouse or other mammal) may be immunized by injection with the native polypeptide, or a synthetic variant thereof, or a derivative of the foregoing. An appropriate immunogenic preparation can contain, for example, recombinantly expressed BLAA polypeptide or a chemically synthesized BLAA polypeptide. The preparation can further include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), human adjuvants such as *Bacille calmette-guerin* and *Corynebacterium parvum*, or similar immunostimulatory agents. If desired, the antibody molecules directed against BLAA can be isolated from the mammal (e.g., from the blood) and further purified by well known techniques, such as protein A chromatography to obtain the IgG fraction.

The term "monoclonal antibody" or "monoclonal antibody composition", as used herein, refers to a population of antibody molecules that contain only one species of an antigen binding site capable of immunoreacting with a particular epitope of BLAA. A monoclonal antibody composition thus typically displays a single binding affinity for a particular BLAA polypeptide with which it immunoreacts. For preparation of monoclonal antibodies directed towards a particular BLAA polypeptide, or derivatives, fragments, analogs or homologs thereof, any technique that provides for the production of antibody molecules by continuous cell line culture may be utilized. Such techniques include, but are not limited to, the hybridoma technique (see Kohler & Milstein, 1975 *Nature* 256: 495–497); the trioma technique; the human B-cell hybridoma technique (see Kozbor, et al., 1983 *Immunol Today* 4: 72) and the EBV hybridoma technique to produce human monoclonal antibodies (see Cole, et al., 1985 In: *MONOCLONAL ANTIBODIES AND CANCER THERAPY*, Alan R. Liss, Inc., pp. 77–96). Human monoclonal antibodies may be utilized in the practice of the present invention and may be produced by using human hybridomas (see Cote, et al., 1983. *Proc Natl Acad Sci USA* 80: 2026–2030) or by transforming human B-cells with Epstein Barr Virus in vitro (see Cole, et al., 1985 In: *MONOCLONAL ANTIBODIES AND CANCER THERAPY*, Alan R. Liss, Inc., pp. 77–96). Each of the above citations are incorporated herein by reference in their entirety.

According to the invention, techniques can be adapted for the production of single-chain antibodies specific to a BLAA polypeptide (see e.g., U.S. Pat. No. 4,946,778). In addition, methodologies can be adapted for the construction of Fab expression libraries (see e.g., Huse, et al., 1989 *Science* 246: 1275–1281) to allow rapid and effective identification of monoclonal $F_{ab}$ fragments with the desired specificity for a BLAA polypeptide or derivatives, fragments, analogs or homologs thereof. Non-human antibodies can be "humanized" by techniques well known in the art. See e.g., U.S. Pat. No. 5,225,539. Antibody fragments that contain the idiotypes to a BLAA polypeptide may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Additionally, recombinant anti-BLAA antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in International Application No. PTC/US86/02269; European Patent Application No. 184,187; European Patent Application No. 171,496; European Patent Application No. 173,494; PCT International Publication No. WO 86/01533; U.S. Pat. No. 4,816,567; U.S. Pat. No. 5,225,539; European Patent Application No. 125,023; Better et al. (1988) *Science* 240:1041–1043; Liu et al. (1987) *PNAS* 84:3439–3443; Liu et al. (1987) *J Immunol.* 139:3521–3526; Sun et al. (1987) *PNAS* 84:214–218; Nishimura et al. (1987) *Cancer Res* 47:999–1005; Wood et al. (1985) *Nature* 314:446–449; Shaw et al. (1988) *J Natl Cancer Inst* 80:1553–1559); Morrison (1985) *Science* 229:1202–1207; Oi et al. (1986) *BioTechniques* 4:214; Jones et al. (1986) *Nature* 321:552–525; Verhoeyan et al. (1988) *Science* 239:1534; and Beidler et al. (1988) *J Immunol* 141:4053–4060. Each of the above citations are incorporated herein by reference in their entirety.

In one embodiment, methodologies for the screening of antibodies that possess the desired specificity include, but are not limited to, enzyme-linked immunosorbent assay (ELISA) and other immunologically-mediated techniques known within the art. In a specific embodiment, selection of antibodies that are specific to a particular domain of a BLAA polypeptide is facilitated by generation of hybridomas that bind to the fragment of a BLAA polypeptide possessing such a domain. Antibodies that are specific for an Ig-like domain within a BLAA polypeptide, or derivatives, fragments, analogs or homologs thereof, are also provided herein.

Anti-BLAA antibodies may be used in methods known within the art relating to the localization and/or quantitation of a BLAA polypeptide (e.g., for use in measuring levels of the BLAA polypeptide within appropriate physiological samples, for use in diagnostic methods, for use in imaging the polypeptide, and the like). In a given embodiment, antibodies for BLAA polypeptides, or derivatives, fragments, analogs or homologs thereof, that contain the antibody derived binding domain, are utilized as pharmacologically-active compounds [hereinafter "therapeutics"].

An anti-BLAA antibody (e.g., monoclonal antibody) can be used to isolate BLAA by standard techniques, such as affinity chromatography or immunoprecipitation. An anti-BLAA antibody can facilitate the purification of natural BLAA from cells and of recombinantly produced BLAA expressed in host cells. Moreover, an anti-BLAA antibody can be used to detect BLAA polypeptide (e.g., in a cellular lysate or cell supernatant) in order to evaluate the abundance and pattern of expression of the BLAA polypeptide. Anti-BLAA antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

BLAA Recombinant Expression Vectors and Host Cells

Another aspect of the invention pertains to vectors, preferably expression vectors, containing a nucleic acid encoding BLAA polypeptide, or derivatives, fragments, analogs or homologs thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., nonepisomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively linked to the nucleic acid sequence to be expressed. Within a recombinant expression vector, "operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *GENE EXPRESSION TECHNOLOGY: METHODS IN ENZYMOLOGY* 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., BLAA polypeptides, mutant forms of BLAA, fusion proteins, etc.).

The recombinant expression vectors of the invention can be designed for expression of BLAA in prokaryotic or eukaryotic cells. For example, BLAA can be expressed in bacterial cells such as *E. coli*, insect cells (using baculovirus expression vectors) yeast cells or mammalian cells. Suitable host cells are discussed further in Goeddel, *GENE EXPRESSION TECHNOLOGY: METHODS IN ENZYMOLOGY* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (1) to increase expression of recombinant protein; (2) to increase the solubility of the recombinant protein; and (3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) *Gene* 67:31–40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) *Gene* 69:301–315) and pET 11d (Studier et al., *GENE EXPRESSION TECHNOLOGY: METHODS IN ENZYMOLOGY* 185, Academic Press, San Diego, Calif. (1990) 60–89).

One strategy to maximize recombinant protein expression in *E. coli* is to express the protein in a host bacteria with an impaired capacity to proteolytically cleave the recombinant protein. See, Gottesman, *GENE EXPRESSION TECHNOLOGY: METHODS IN ENZYMOLOGY* 185, Academic Press, San Diego, Calif. (1990) 119–128. Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

In another embodiment, the BLAA expression vector is a yeast expression vector. Examples of vectors for expression in yeast *S. cerivisae* include pYepSec1 (Baldari, et al., (1987) *EMBO J* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (InVitrogen Corp, San Diego, Calif.).

Alternatively, BLAA can be expressed in insect cells using baculovirus expression vectors. Baculovirus vectors available for expression of proteins in cultured insect cells (e.g., SF9 cells) include the pAc series (Smith et al. (1983) *Mol Cell Biol* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed (1987) *Nature* 329:840) and pMT2PC (Kaufman et al. (1987) *EMBO J* 6: 187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells. See, e.g., Chapters 16 and 17 of Sambrook et al., *MOLECULAR CLONING: A LABORATORY MANUAL*. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev* 1:268–277), lymphoid-specific promoters (Calame and Eaton (1988) *Adv Immunol* 43:235–275), in particular promoters of T cell receptors (Winoto and Baltimore (1989) *EMBO J* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *PNAS* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss (1990) *Science* 249:374–379) and the α-fetoprotein promoter (Campes and Tilghman (1989) *Genes Dev* 3:537–546).

The invention further provides a recombinant expression vector comprising a DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to BLAA mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al., "Antisense RNA as a molecular tool for genetic analysis," Reviews—Trends in Genetics, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, BLAA polypeptide can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*MOLECULAR CLONING: A LABORATORY MANUAL*. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding BLAA or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) BLAA polypeptide. Accordingly, the invention further provides methods for producing BLAA polypeptide using the host cells of the invention. In one embodiment, the method comprises culturing the host cell of invention (into which a recombinant expression vector encoding BLAA has been introduced) in a suitable medium such that BLAA polypeptide is produced. In another embodiment, the method further comprises isolating BLAA from the medium or the host cell.

Transgenic Animals

The host cells of the invention can also be used to produce nonhuman transgenic animals. For example, in one embodiment, a host cell of the invention is a fertilized oocyte or an embryonic stem cell into which BLAA-coding sequences have been introduced. Such host cells can then be used to create non-human transgenic animals in which exogenous BLAA sequences have been introduced into their genome or homologous recombinant animals in which endogenous BLAA sequences have been altered. Such animals are useful for studying the function and/or activity of BLAA and for identifying and/or evaluating modulators of BLAA activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA that is integrated into the genome of a cell from which a transgenic animal develops and that remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous BLAA gene has been altered by homologous recombination between the endogenous gene and an exogenous DNA molecule introduced into a cell of the animal, e.g., an embryonic cell of the animal, prior to development of the animal.

A transgenic animal of the invention can be created by introducing BLAA-encoding nucleic acid into the male pronuclei of a fertilized oocyte, e.g., by microinjection, retroviral infection, and allowing the oocyte to develop in a pseudopregnant female foster animal. The human BLAA cDNA sequence of SEQ ID NO: 1, 3, 5, 7, 9, or 11, can be introduced as a transgene into the genome of a non-human animal. Alternatively, a nonhuman homologue of the human BLAA gene, such as a mouse BLAA gene, can be isolated based on hybridization to the human BLAA cDNA (described further above) and used as a transgene. Intronic sequences and polyadenylation signals can also be included in the transgene to increase the efficiency of expression of the transgene. A tissue-specific regulatory sequence(s) can be operably linked to the BLAA transgene to direct expression of BLAA polypeptide to particular cells. Methods for generating transgenic animals via embryo manipulation and microinjection, particularly animals such as mice, have become conventional in the art and are described, for example, in U.S. Pat. Nos. 4,736,866; 4,870,009; and 4,873,191; and Hogan 1986, In: *MANIPULATING THE MOUSE EMBRYO*, Cold Spring Harbor Laboratory Press, Cold Spring Harbor, N.Y. Similar methods are used for production of other transgenic animals. A transgenic founder animal can be identified based upon the presence of the BLAA transgene in its genome and/or expression of BLAA mRNA in tissues or cells of the animals. A transgenic founder animal can then be used to breed additional animals carrying the transgene. Moreover, transgenic animals carrying a transgene encoding BLAA can further be bred to other transgenic animals carrying other transgenes.

To create a homologous recombinant animal, a vector is prepared which contains at least a portion of a BLAA gene into which a deletion, addition or substitution has been introduced to thereby alter, e.g., functionally disrupt, the BLAA gene. The BLAA gene can be a human gene (e.g., the cDNA of SEQ ID NO: 1, 3, 5, 7, 9, or 11), but more preferably, is a non-human homologue of a human BLAA gene. For example, a mouse homologue of human BLAA gene of SEQ ID NO: 1, 3, 5, 7, 9, or 11 can be used to construct a homologous recombination vector suitable for altering an endogenous BLAA gene in the mouse genome. In one embodiment, the vector is designed such that, upon homologous recombination, the endogenous BLAA gene is functionally disrupted (i.e., no longer encodes a functional protein; also referred to as a "knock out" vector).

Alternatively, the vector can be designed such that, upon homologous recombination, the endogenous BLAA gene is mutated or otherwise altered but still encodes functional protein (e.g., the upstream regulatory region can be altered to thereby alter the expression of the endogenous BLAA polypeptide). In the homologous recombination vector, the altered portion of the BLAA gene is flanked at its 5' and 3' ends by additional nucleic acid of the BLAA gene to allow for homologous recombination to occur between the exogenous BLAA gene carried by the vector and an endogenous BLAA gene in an embryonic stem cell. The additional flanking BLAA nucleic acid is of sufficient length for successful homologous recombination with the endogenous gene. Typically, several kilobases of flanking DNA (both at the 5' and 3' ends) are included in the vector. See e.g., Thomas et al. (1987) *Cell* 51:503 for a description of homologous recombination vectors. The vector is introduced into an embryonic stem cell line (e.g., by electroporation) and cells in which the introduced BLAA gene has homologously recombined with the endogenous BLAA gene are selected (see e.g., Li et al. (1992) *Cell* 69:915).

The selected cells are then injected into a blastocyst of an animal (e.g., a mouse) to form aggregation chimeras. See e.g., Bradley 1987, In: *TERATOCARCINOMAS AND EMBRYONIC STEM CELLS: A PRACTICAL APPROACH*, Robertson, ed. IRL, Oxford, pp. 113–152. A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Curr Opin Biotechnol* 2:823–829; PCT International Publication Nos.: WO 90/11354; WO 91/01140; WO 92/0968; and WO 93/04169.

In another embodiment, transgenic non-humans animals can be produced that contain selected systems that allow for regulated expression of the transgene. One example of such a system is the cre/loxP recombinase system of bacteriophage P1. For a description of the cre/loxP recombinase system, see, e.g., Lakso et al. (1992) *PNAS* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810–813. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

Pharmaceutical Compositions

The BLAA nucleic acid molecules, BLAA polypeptides, and anti-BLAA antibodies (also referred to herein as "active compounds") of the invention, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifingal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a BLAA polypeptide or anti-BLAA antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *PNAS* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

The pharmaceutical compositions can be included in a container, pack, or dispenser together with instructions for administration.

Uses and Methods of the Invention

The immunoglobulin superfamily members include multifunctional secreted and membrane-bound proteins that modulate a number of functions. B7 molecules known in the prior art are located on the cell surface. (See Selvakumar et al. 1992, Immunogenetics 36:175–181 and Linsley et al. 1994, Protein Sc. 3:1341–1343). Sequence analysis studies using programs known in the prior art (e.g., PSORT) show that the polypeptides of the instant invention are most likely localized in the membrane of the endoplasmic reticulum. The nucleic acid molecules, proteins, protein homologues, and antibodies described herein can be used in one or more of the following methods: (a) screening assays; (b) detection assays (e.g., chromosomal mapping, tissue typing, forensic biology), (c) predictive medicine (e.g., diagnostic assays, prognostic assays, monitoring clinical trials, and pharmacogenomics); and (d) methods of treatment (e.g., therapeutic and prophylactic). As described herein, in one embodiment, a BLAA polypeptide of the invention has the ability to bind to activated T lymphocytes and provide regulatory signals for T lymphocyte cell growth and activation. A BLAA polypeptide interacts with other cellular proteins and can thus be used to modulate immune response-associated protein activity. Such modulation may have an effect on the regulation of cellular proliferation, the regulation of cellular differentiation, and/or the regulation of cell survival.

The isolated nucleic acid molecules of the invention can be used to express BLAA polypeptide (e.g., via a recombinant expression vector in a host cell in gene therapy applications), to detect BLAA mRNA (e.g., in a biological sample) or a genetic lesion in a BLAA gene, and to modulate BLAA activity, as described further below. In addition, the BLAA polypeptides can be used to screen drugs or compounds that modulate the BLAA activity or expression as well as to treat disorders characterized by insufficient or excessive production of BLAA polypeptide or production of BLAA polypeptide forms that have decreased or aberrant activity compared to BLAA wild type polypeptide (e.g. infectious diseases, cancers, autoimmune disorders, and complications associated with transplantation). In addition, the anti-BLAA antibodies of the invention can be used to detect and isolate BLAA polypeptides and modulate BLAA activity.

This invention further pertains to novel agents identified by the above described screening assays and uses thereof for treatments as described herein.

Screening Assays

The invention provides a method (also referred to herein as a "screening assay") for identifying modulators, i.e., candidate or test compounds or agents (e.g., peptides, peptidomimetics, small molecules or other drugs) that bind to BLAA polypeptides or have a stimulatory or inhibitory effect on, for example, BLAA expression or BLAA activity.

In one embodiment, the invention provides assays for screening candidate or test compounds which bind to or modulate the activity of a BLAA protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) *Anticancer Drug Des* 12:145).

Examples of methods for the synthesis of molecular libraries can be found in the art, for example in: DeWitt et al. (1993) *Proc Natl Acad Sci U.S.A.* 90:6909; Erb et al. (1994) *Proc Natl Acad Sci U.S.A.* 91:11422; Zuckermann et al. (1994) *J Med Chem* 37:2678; Cho et al. (1993) *Science* 261:1303; Carrell et al. (1994) *Angew Chem Int Ed Engl* 33:2059; Carell et al. (1994) *Angew Chem Int Ed Engl* 33:2061; and Gallop et al. (1994) *J Med Chem* 37:1233.

Libraries of compounds may be presented in solution (e.g., Houghten (1992) *Biotechniques* 13:412–421), or on beads (Lam (1991) *Nature* 354:82–84), on chips (Fodor (1993) *Nature* 364:555–556), bacteria (Ladner U.S. Pat. No. 5,223,409), spores (Ladner U.S. Pat. No. '409), plasmids (Cull et al. (1992) *Proc Natl Acad Sci USA* 89:1865–1869) or on phage (Scott and Smith (1990) *Science* 249:386–390; Devlin (1990) *Science* 249:404–406; Cwirla et al. (1990) *Proc Natl Acad Sci U.S.A.* 87:6378–6382; Felici (1991) *J Mol Biol* 222:301–310; Ladner above.).

In one embodiment, an assay is a cell-based assay in which a cell which expresses a form of BLAA polypeptide, or a biologically active portion thereof, on the cell surface is contacted with a test compound and the ability of the test compound to bind to a BLAA protein determined. The cell, for example, can be of mammalian origin or be a yeast cell. Determining the ability of the test compound to bind to the BLAA polypeptide can be accomplished, for example, by coupling the test compound with a radioisotope or enzymatic label such that binding of the test compound to the BLAA polypeptide or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In one embodiment, the assay comprises contacting a cell which expresses a membrane-bound form of BLAA polypeptide, or a biologically active portion thereof, on the cell surface with a known compound which binds BLAA to form an assay mixture, contacting the assay mixture with a test compound, and determining the ability of the test compound to interact with a BLAA polypeptide, wherein determining the ability of the test compound to interact with a BLAA polypeptide comprises determining the ability of the test compound to preferentially bind to BLAA or a biologically active portion thereof as compared to the known compound.

In another embodiment, an assay is a cell-based assay comprising contacting a cell expressing a membrane-bound form of BLAA polypeptide, or a biologically active portion thereof, on the cell surface with a test compound and determining the ability of the test compound to modulate (e.g., stimulate or inhibit) the activity of the BLAA polypeptide or biologically active portion thereof. Determining the ability of the test compound to modulate the activity of BLAA or a biologically active portion thereof can be accomplished, for example, by determining the ability of the BLAA polypeptide to bind to or interact with a BLAA target molecule. As used herein, a "target molecule" is a molecule with which a BLAA polypeptide binds or interacts in nature, for example, a molecule on the surface of a cell which expresses a BLAA-interacting protein, a molecule on the surface of a second cell, a molecule in the extracellular milieu, a molecule associated with the internal surface of a cell membrane or a cytoplasmic molecule. A BLAA target molecule can be a non-BLAA molecule or a BLAA protein or polypeptide of the present invention. In one embodiment, a BLAA target molecule is a component of a signal transduction pathway that facilitates transduction of an extracellular signal (e.g. a signal generated by binding of a compound to a membrane-bound BLAA molecule) through the cell membrane and into the cell. The target, for example, can be a second intercellular protein that has catalytic activity or a protein that facilitates the association of downstream signaling molecules with BLAA.

Determining the ability of the BLAA polypeptide to bind to or interact with a BLAA target molecule can be accomplished by one of the methods described above for determining direct binding. In one embodiment, determining the ability of the BLAA polypeptide to bind to or interact with a BLAA target molecule can be accomplished by determining the activity of the target molecule. For example, the activity of the target molecule can be determined by detecting induction of a cellular second messenger of the target (i.e. intracellular $Ca^{2+}$, diacylglycerol, $IP_3$, etc.), detecting catalytic/enzymatic activity of the target an appropriate substrate, detecting the induction of a reporter gene (comprising a BLAA-responsive regulatory element operatively linked to a nucleic acid encoding a detectable marker, e.g., luciferase), or detecting a cellular response, for example, cell survival, cellular differentiation, or cell proliferation.

In yet another embodiment, an assay of the present invention is a cell-free assay comprising contacting a BLAA polypeptide or biologically active portion thereof with a test compound and determining the ability of the test compound to bind to the BLAA polypeptide or biologically active portion thereof. Binding of the test compound to the BLAA polypeptide can be determined either directly or indirectly as described above. In one embodiment, the assay comprises contacting the BLAA polypeptide or biologically active portion thereof with a known compound which binds BLAA to form an assay mixture, contacting the assay mixture with a test compound, and determining the ability of the test compound to interact with a BLAA polypeptide, wherein determining the ability of the test compound to interact with a BLAA polypeptide comprises determining the ability of the test compound to preferentially bind to BLAA or biologically active portion thereof as compared to the known compound.

In another embodiment, an assay is a cell-free assay comprising contacting BLAA polypeptide or biologically active portion thereof with a test compound and determining the ability of the test compound to modulate (e.g. stimulate or inhibit) the activity of the BLAA polypeptide or biologically active portion thereof. Determining the ability of the test compound to modulate the activity of BLAA can be accomplished, for example, by determining the ability of the BLAA polypeptide to bind to a BLAA target molecule by one of the methods described above for determining direct binding. In an alternative embodiment, determining the ability of the test compound to modulate the activity of BLAA can be accomplished by determining the ability of the BLAA polypeptide further modulate a BLAA target molecule. For example, the catalytic/enzymatic activity of the target molecule on an appropriate substrate can be determined as previously described.

In yet another embodiment, the cell-free assay comprises contacting the BLAA polypeptide or biologically active portion thereof with a known compound which binds BLAA to form an assay mixture, contacting the assay mixture with a test compound, and determining the ability of the test compound to interact with a BLAA polypeptide, wherein determining the ability of the test compound to interact with a BLAA polypeptide comprises determining the ability of the BLAA polypeptide to preferentially bind to or modulate the activity of a BLAA target molecule.

The cell-free assays of the present invention are amenable to use of both the soluble form or the membrane-bound form of BLAA. In the case of cell-free assays comprising the membrane-bound form of BLAA, it may be desirable to utilize a solubilizing agent such that the membrane-bound form of BLAA is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, N-dodecyl-N,N-dimethyl-3-ammonio-1-propane sulfonate, 3-(3-cholamidopropyl)dimethylamminiol-1-propane sulfonate (CHAPS), or 3-(3-cholamidopropyl)dimethylamminiol-2-hydroxy-1-propane sulfonate (CHAPSO).

In more than one embodiment of the above assay methods of the present invention, it may be desirable to immobilize either BLAA or its target molecule to facilitate separation of complexed from uncomplexed forms of one or both of the proteins, as well as to accommodate automation of the assay. Binding of a test compound to BLAA, or interaction of BLAA with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided that adds a domain that allows one or both of the proteins to be bound to a matrix. For example, GST-BLAA fusion proteins or GST-target fusion proteins can be adsorbed onto glutathione sepharose beads (Sigma Chemical, St. Louis, Mo.) or glutathione derivatized microtiter plates, that are then combined with the test compound or the test compound and either the non-adsorbed target protein or BLAA polypeptide, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of BLAA binding or activity determined using standard techniques.

Other techniques for immobilizing proteins on matrices can also be used in the screening assays of the invention. For example, either BLAA or its target molecule can be immobilized utilizing conjugation of biotin and streptavidin. Biotinylated BLAA or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with BLAA or target molecules, but which do not interfere with binding of the BLAA protein to its target molecule, can be derivatized to the wells of the plate, and unbound target or BLAA trapped in the wells by antibody conjugation. Methods for detecting such complexes, in addition to those described above for the GST-immobilized complexes, include immunodetection of complexes using antibodies reactive with the BLAA or target molecule, as well as enzyme-linked assays that rely on detecting an enzymatic activity associated with the BLAA or target molecule.

In another embodiment, modulators of BLAA expression are identified in a method wherein a cell is contacted with a candidate compound and the expression of BLAA mRNA or polypeptide in the cell is determined. The level of expression of BLAA mRNA or polypeptide in the presence of the candidate compound is compared to the level of expression of BLAA mRNA or polypeptide in the absence of the candidate compound. The candidate compound can then be identified as a modulator of BLAA expression based on this comparison. For example, when expression of BLAA mRNA or polypeptide is greater (statistically significantly greater) in the presence of the candidate compound than in its absence, the candidate compound is identified as a stimulator of BLAA mRNA or polypeptide expression. Alternatively, when expression of BLAA mRNA or polypeptide is less (statistically significantly less) in the presence of the candidate compound than in its absence, the candidate compound is identified as an inhibitor of BLAA mRNA or polypeptide expression. The level of BLAA mRNA or protein expression in the cells can be determined by methods described herein for detecting BLAA mRNA or protein.

In yet another aspect of the invention, a BLAA polypeptide can be used as "bait proteins" in a two-hybrid assay or three hybrid assay (see, e.g., U.S. Pat. No. 5,283,317; Zervos et al. (1993) Cell 72:223–232; Madura et al. (1993) J Biol Chem 268:12046–12054; Bartel et al. (1993) Biotechniques 14:920–924; Iwabuchi et al. (1993) Oncogene 8:1693–1696; and Brent WO94/10300), to identify other proteins that bind to or interact with BLAA ("BLAA-binding proteins" or "BLAA-bp") and modulate BLAA activity. Such BLAA-binding proteins are also likely to be involved in the propagation of signals by the BLAA polypeptides as, for example, upstream or downstream elements of the BLAA pathway.

The two-hybrid system is based on the modular nature of most transcription factors, which consist of separable DNA-binding and activation domains. Briefly, the assay utilizes two different DNA constructs. In one construct, the gene that codes for BLAA is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a BLAA-dependent complex, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to obtain the cloned gene that encodes the protein which interacts with BLAA.

In another embodiment, modulators of activity or latency of (i.e., the lack of activity) or predisposition to an immune response-associated disorder are identified wherein a test animal at increased risk for an immune response-associated disorder is administered with a test compound. The test animal of this embodiment recombinantly expresses a BLAA polypeptide. The activity of said polypeptide is then measured in the test animal. Next, the activity of the polypeptide is measured in a control animal that recombinantly expresses the polypeptide but that is not at an increased risk for an immune response-associated disorder. Finally, expression in the test animal is compared to the expression in the control animal. A difference in the test animal relative to the control animal indicates that the test compound is a modulation of activity or latency of or predisposition to an immune response-associated disorder. For example, an increase in expression in the test animal indicates that the test compound is a stimulator of an immune response-associated disorder. Likewise, a decrease in the test animal indicates that the test compound is an inhibitor of an immune response-associated disorder.

The test animal may be a recombinant test animal that expresses a test protein transgene, as described above, or expresses said transgene under the control of a promoter at increased levels compared to a wild type test animal. In this embodiment, the promoter is not the native promoter of the transgene.

This invention further pertains to novel agents identified by the above-described screening assays and uses thereof for treatments as described herein.

Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; and (ii) identify an individual from a minute biological sample (tissue typing). These applications are described in the subsections below.

Chromosome Mapping

Once the sequence (or a portion of the sequence) of a gene has been isolated, this sequence can be used to map the location of the gene on a chromosome. This process is called chromosome mapping. Accordingly, portions or fragments of the BLAA sequences described herein, can be used to map the location of the BLAA genes, respectively, on a chromosome. The mapping of the BLAA sequences to chromosomes is an important first step in correlating these sequences with genes associated with disease.

Briefly, BLAA genes can be mapped to chromosomes by preparing PCR primers (preferably 15–25 bp in length) from the BLAA sequences. Computer analysis of the BLAA, sequences can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the BLAA sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but in which human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio et al. (1983) *Science* 220:919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the BLAA sequences to design oligonucleotide primers, sublocalization can be achieved with panels of fragments from specific chromosomes.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical like colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases, will suffice to get good results at a reasonable amount of time. For a review of this technique, see Verma et al., *HUMAN CHROMOSOMES: A MANUAL OF BASIC TECHNIQUES* (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. Such data are found, for example, in McKusick, MENDELIAN INHERITANCE IN MAN, available on-line through Johns Hopkins University Welch Medical Library). The relationship between genes and disease, mapped to the same chromosomal region, can then be identified through linkage analysis (co-inheritance of physically adjacent genes), described in, for example, Egeland et al. (1987) Nature, 325:783–787.

Moreover, differences in the DNA sequences between individuals affected and unaffected with a disease associated with the BLAA gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing

The BLAA sequences of the present invention can also be used to identify individuals from minute biological samples. In this technique, an individual's genomic DNA is digested with one or more restriction enzymes, and probed on a Southern blot to yield unique bands for identification. The sequences of the present invention are useful as additional DNA markers for RFLP ("restriction fragment length polymorphisms," described in U.S. Pat. No. 5,272,057).

Furthermore, the sequences of the present invention can be used to provide an alternative technique that determines the actual base-by-base DNA sequence of selected portions of an individual's genome. Thus, the BLAA sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The BLAA sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Much of the allelic variation is due to single nucleotide polymorphisms (SNPs), which include restriction fragment length polymorphisms (RFLPs).

Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO: 1, SEQ ID NO: 3, and SEQ ID NO: 5 (SEQ ID NOs: 8, 10, and 12, respectively) can comfortably provide positive individual identification with a panel of perhaps 10 to 1,000 primers that each yield a noncoding amplified sequence of 100 bases. If predicted coding sequences, such as those in SEQ ID NO: 1, 3, 5, 7, 9, and 11 are used, a more appropriate number of primers for individual positive identification would be 500–2000.

Predictive Medicine

The present invention also pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the present invention relates to diagnostic assays for determining BLAA polypeptide and/or nucleic acid expression as well as BLAA activity, in the context of a biological sample (e.g., blood, serum, cells, tissue) to thereby determine whether an individual is afflicted with a disease or disorder, or is at risk of developing a disorder, associated with aberrant BLAA expression or activity. The invention also provides for prognostic (or predictive) assays for determining whether an individual is at risk of developing a disorder associated with BLAA polypeptide or nucleic acid expression or activity. For example, mutations in a BLAA gene can be assayed in a biological sample. Such assays can be used for prognostic or predictive purpose to thereby prophylactically treat an individual prior to the onset of a disorder characterized by or associated with BLAA polypeptide or nucleic acid expression or activity.

Another aspect of the invention provides methods for determining BLAA polypeptide or nucleic acid expression or BLAA activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.)

Yet another aspect of the invention pertains to monitoring the influence of agents (e.g., drugs, compounds) on the expression or activity of BLAA in clinical trials.

These and other agents are described in further detail in the following sections.

Diagnostic Assays

An exemplary method for detecting the presence or absence of BLAA in a biological sample involves obtaining a biological sample from a test subject and contacting the biological sample with a compound or an agent capable of detecting BLAA polypeptide or nucleic acid (e.g., mRNA, genomic DNA) that encodes BLAA polypeptide such that the presence of BLAA is detected in the biological sample. An agent for detecting BLAA mRNA or genomic DNA is a labeled nucleic acid probe capable of hybridizing to BLAA mRNA or genomic DNA. The nucleic acid probe can be, for example, a full-length BLAA nucleic acid, such as the nucleic acid of SEQ ID NO: 1, 3, 5, 7, 8, 9, 10, 11, or 12, or a portion thereof, such as an oligonucleotide of at least 15, 30, 50, 100, 250 or 500 nucleotides in length and sufficient to specifically hybridize under stringent conditions to BLAA mRNA or genomic DNA. Other suitable probes for use in the diagnostic assays of the invention are described herein.

An agent for detecting BLAA polypeptide is an antibody capable of binding to BLAA protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect BLAA mRNA, polypeptide, or genomic DNA in a biological sample in vitro as well as in vivo. For example, in vitro techniques for detection of BLAA mRNA include Northern hybridizations and in situ hybridizations. In vitro techniques for detection of BLAA polypeptide include enzyme linked immunosorbent assays (ELISAs), Western blots, immunoprecipitations and immunofluorescence. In vitro techniques for detection of BLAA genomic DNA include Southern hybridizations. Furthermore, in vivo techniques for detection of BLAA protein include introducing into a subject a labeled anti-BLAA antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting BLAA polypeptide, mRNA, or genomic DNA, such that the presence of BLAA polypeptide, mRNA or genomic DNA is detected in the biological sample, and comparing the presence of BLAA polypeptide, mRNA or genomic DNA in the control sample with the presence of BLAA polypeptide, mRNA or genomic DNA in the test sample.

The invention also encompasses kits for detecting the presence of BLAA in a biological sample. For example, the kit can comprise: a labeled compound or agent capable of detecting BLAA polypeptide or mRNA in a biological sample; means for determining the amount of BLAA in the sample; and means for comparing the amount of BLAA in the sample with a standard. The compound or agent can be packaged in a suitable container. The kit can further comprise instructions for using the kit to detect BLAA polypeptide or nucleic acid.

Prognostic Assays

The diagnostic methods described herein can furthermore be utilized to identify subjects having or at risk of developing a disease or disorder associated with aberrant BLAA expression or activity. For example, the assays described herein, such as the preceding diagnostic assays or the following assays, can be utilized to identify a subject having or at risk of developing an immune response-associated disorder associated with BLAA polypeptide or nucleic acid expression or activity such as cancers, infectious diseases, autoimmune disorders, and complications associated with transplantation. Alternatively, the prognostic assays can be utilized to identify a subject having or at risk for developing a disease or disorder. Thus, the present invention provides a method for identifying a disease or disorder associated with aberrant BLAA expression or activity in which a test sample is obtained from a subject and BLAA polypeptide or nucleic acid (e.g., mRNA, genomic DNA) is detected, wherein the presence of BLAA polypeptide or nucleic acid is diagnostic for a subject having or at risk of developing a disease or disorder associated with aberrant BLAA expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant BLAA expression or activity. For example, such methods can be used to determine whether a subject can be effectively treated with an agent for a disorder, such as cancer, infectious disease, autoimmune disorders, and complications associated with transplantation. Thus, the present invention provides methods for determining whether a subject can be effectively treated with an agent for a disorder associated with aberrant BLAA expression or activity in which a test sample is obtained and a BLAA polypeptide or nucleic acid is detected (e.g., wherein the presence of a BLAA polypeptide or nucleic acid is diagnostic for a subject that can be administered the agent to treat a disorder associated with aberrant BLAA expression or activity.)

The methods of the invention can also be used to detect genetic lesions in a BLAA gene, thereby determining if a subject with the lesioned gene is at risk for a disorder characterized by aberrant cell proliferation and/or differentiation. In various embodiments, the methods include detecting, in a sample of cells from the subject, the presence or absence of a genetic lesion characterized by at least one of an alteration affecting the integrity of a gene encoding a BLAA polypeptide, or the mis-expression of the BLAA gene. For example, such genetic lesions can be detected by ascertaining the existence of at least one of (1) a deletion of one or more nucleotides from a BLAA gene; (2) an addition of one or more nucleotides to a BLAA gene; (3) a substitution of one or more nucleotides of a BLAA gene, (4) a chromosomal rearrangement of a BLAA gene; (5) an alteration in the level of a messenger RNA transcript of a BLAA gene, (6) aberrant modification of a BLAA gene, such as of the methylation pattern of the genomic DNA, (7) the presence of a non-wild type splicing pattern of a messenger RNA transcript of a BLAA gene, (8) a non-wild type level of a BLAA polypeptide, (9) allelic loss of a BLAA gene, and (10) inappropriate post-translational modification of a BLAA polypeptide. As described herein, there are a large number of assay techniques known in the art which can be used for detecting lesions in a BLAA gene. A preferred biological sample is a peripheral blood leukocyte sample isolated by conventional means from a subject. However, any biological sample containing nucleated cells may be used, including, for example, buccal mucosal cells.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *PNAS* 91:360–364), the latter of which can be particularly useful for detecting point mutations in the BLAA-gene (see Abravaya et al. (1995) *Nucl Acids Res* 23:675–682). This method can include the steps of collecting a sample of cells from a patient, isolating nucleic acid (e.g., genomic, mRNA or both) from the cells of the sample, contacting the nucleic acid sample with one or more primers that specifically hybridize to a BLAA gene under conditions such that hybridization and amplification of the BLAA gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al., 1990, *Proc Natl Acad Sci USA* 87:1874–1878), transcriptional amplification system (Kwoh, et al., 1989, *Proc Natl Acad Sci USA* 86:1173–1177), Q-Beta Replicase (Lizardi et al, 1988, *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a BLAA gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,493,531) can be used to score for the presence of specific mutations by development or loss of a ribozyme cleavage site.

In other embodiments, genetic mutations in BLAA can be identified by hybridizing a sample and control nucleic acids, e.g., DNA or RNA, to high density arrays containing hundreds or thousands of oligonucleotides probes (Cronin et al. (1996) *Human Mutation* 7: 244–255; Kozal et al. (1996) *Nature Medicine* 2: 753–759). For example, genetic mutations in BLAA can be identified in two dimensional arrays containing light-generated DNA probes as described in Cronin et al. above. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the BLAA gene and detect mutations by comparing the sequence of the sample BLAA with the corresponding wild-type (control) sequence. Examples of sequencing reactions include those based on techniques developed by Maxim and Gilbert (1977) *PNAS* 74:560 or Sanger (1977) *PNAS* 74:5463. It is also contemplated that any of a variety of automated sequencing procedures can be utilized when performing the diagnostic assays (Naeve et al., (1995) *Biotechniques* 19:448), including sequencing by mass spectrometry (see, e.g., PCT International Publ. No. WO 94/16101; Cohen et al. (1996) *Adv Chromatogr* 36:127–162; and Griffin et al. (1993) *Appl Biochem Biotechnol* 38:147–159).

Other methods for detecting mutations in the BLAA gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type BLAA sequence with potentially mutant RNA or DNA obtained from a tissue sample. The double-stranded duplexes are treated with an agent that cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al (1988) *Proc Natl Acad Sci USA* 85:4397; Saleeba et al (1992) *Methods Enzymol* 217:286–295. In an embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in BLAA cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a BLAA sequence, e.g., a wild-type BLAA sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in BLAA genes. For example, single strand conformation polymorphism (SSCP) may be used to detect differences in electrophoretic mobility between mutant and wild type nucleic acids (Orita et al. (1989) *Proc Natl Acad Sci USA*: 86:2766, see also Cotton (1993) *Mutat Res* 285:125–144; Hayashi (1992) *Genet Anal Tech Appl* 9:73–79). Single-stranded DNA fragments of sample and control BLAA nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found (Saiki et al. (1986) *Nature* 324:163); Saiki et al. (1989) *Proc Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al (1992) *Mol Cell Probes* 6:1). It is anticipated that in certain embodiments amplification may also be performed using Taq ligase for amplification (Barany (1991) *Proc Natl Acad Sci USA* 88:189). In such cases, ligation will occur only if there is a perfect match at the 3' end of the 5' sequence, making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a BLAA gene.

Furthermore, any cell type or tissue, preferably peripheral blood leukocytes, in which BLAA is expressed may be utilized in the prognostic assays described herein. However, any biological sample containing nucleated cells may be used, including, for example, buccal mucosal cells.

Pharmacogenomics

Agents, or modulators that have a stimulatory or inhibitory effect on BLAA activity (e.g., BLAA gene expression), as identified by a screening assay described herein can be administered to individuals to treat (prophylactically or therapeutically) disorders (e.g., cancer, infectious disease, autoimmune disorders, and complications associated with transplantation) associated with aberrant BLAA activity. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of BLAA polypeptide, expression of BLAA nucleic acid, or mutation content of BLAA genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See e.g., Eichelbaum, *Clin Exp Pharmacol Physiol*, 1996, 23:983–985 and Linder, *Clin Chem*, 1997, 43:254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase (G6PD) deficiency is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of BLAA polypeptide, expression of BLAA nucleic acid, or mutation content of BLAA genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a BLAA modulator, such as a modulator identified by one of the exemplary screening assays described herein.

Monitoring of Effects During Clinical Trials

Monitoring the influence of agents (e.g., drugs, compounds) on the expression or activity of BLAA (e.g., the ability to modulate aberrant cell proliferation and/or differentiation) can be applied not only in basic drug screening, but also in clinical trials. For example, the effectiveness of an agent determined by a screening assay as described herein to increase BLAA gene expression, protein levels, or upregulate BLAA activity, can be monitored in clinical trails of subjects exhibiting decreased BLAA gene expression, protein levels, or downregulated BLAA activity. Alternatively, the effectiveness of an agent determined by a screening assay to decrease BLAA gene expression, protein levels, or downregulate BLAA activity, can be monitored in clinical trails of subjects exhibiting increased BLAA gene expression, protein levels, or upregulated BLAA activity. In such clinical trials, the expression or activity of BLAA and, preferably, other genes that have been implicated in, for example, an immune response-associated disorder can be used as a "read out" or markers of the immune responsiveness of a particular cell.

For example, and not by way of limitation, genes, including BLAA, that are modulated in cells by treatment with an agent (e.g., compound, drug or small molecule) that modulates BLAA activity (e.g., identified in a screening assay as described herein) can be identified. Thus, to study the effect of agents on cellular proliferation disorders, for example, in a clinical trial, cells can be isolated and RNA prepared and analyzed for the levels of expression of BLAA and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of BLAA or other genes. In this way, the gene expression pattern can serve as a marker, indicative of the physiological response of the cells to the agent. Accordingly, this response state may be determined before, and at various points during, treatment of the individual with the agent.

In one embodiment, the present invention provides a method for monitoring the effectiveness of treatment of a subject with an agent (e.g., an agonist, antagonist, protein, polypeptide, peptidomimetic, nucleic acid, small molecule, or other drug candidate identified by the screening assays described herein) comprising the steps of (i) obtaining a pre-administration sample from a subject prior to administration of the agent; (ii) detecting the level of expression of a BLAA polypeptide, mRNA, or genomic DNA in the preadministration sample; (iii) obtaining one or more post-administration samples from the subject; (iv) detecting the level of expression or activity of the BLAA polypeptide, mRNA, or genomic DNA in the post-administration samples; (v) comparing the level of expression or activity of the BLAA polypeptide, mRNA, or genomic DNA in the pre-administration sample with the BLAA polypeptide, mRNA, or genomic DNA in the post administration sample or samples; and (vi) altering the administration of the agent to the subject accordingly. For example, increased administration of the agent may be desirable to increase the expression or activity of BLAA to higher levels than detected, i.e., to increase the effectiveness of the agent. Alternatively, decreased administration of the agent may be desirable to decrease expression or activity of BLAA to lower levels than detected, i.e., to decrease the effectiveness of the agent.

Methods of Treatment

The present invention provides for both prophylactic and therapeutic methods of treating a subject at risk of (or susceptible to) a disorder or having a disorder associated with aberrant BLAA expression or activity.

Disorders

Diseases and disorders that are characterized by increased (relative to a subject not suffering from the disease or disorder) levels or biological activity may be treated with therapeutics that antagonize (i.e., reduce or inhibit) activity. Therapeutics that antagonize activity may be administered in a therapeutic or prophylactic manner. Therapeutics that may be utilized include, but are not limited to, (i) an aforementioned polypeptide, or analogs, derivatives, fragments or homologs thereof, (ii) antibodies to an aforementioned polypeptide; (iii) nucleic acids encoding an aforementioned polypeptide; (iv) administration of antisense nucleic acid and nucleic acids that are "dysfinctional" (i.e., due to a heterologous insertion within the coding sequences of coding sequences to an aforementioned polypeptide) that are utilized to "knockout" endogenous function of an aforementioned peptide by homologous recombination (see, e.g., Capecchi, 1989, *Science* 244: 1288–1292); or (v) modulators (i.e., inhibitors, agonists and antagonists, including additional polypeptide mimetic of the invention or antibodies specific to a peptide of the invention) that alter the interaction between an aforementioned polypeptide and its binding partner.

Diseases and disorders that are characterized by decreased (relative to a subject not suffering from the disease or disorder) levels or biological activity may be treated with therapeutics that increase (i.e., are agonists to) activity. Therapeutics that upregulate activity may be administered in a therapeutic or prophylactic manner. Therapeutics that may be utilized include, but are not limited to, an aforementioned polypeptide, or analogs, derivatives, fragments or homologs thereof, or an agonist that increases bioavailability.

Increased or decreased levels can be readily detected by quantifying polypeptide and/or RNA, by obtaining a patient tissue sample (e.g., from biopsy tissue) and assaying it in vitro for RNA or peptide levels, structure and/or activity of the expressed polypeptides (or mRNAs of an aforementioned polypeptide). Methods that are well-known within the art include, but are not limited to, immunoassays (e.g., by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, etc.).

Prophylactic Methods

In one aspect, the invention provides a method for preventing, in a subject, a disease or condition associated with an aberrant BLAA expression or activity, by administering to the subject an agent that modulates BLAA expression or at least one BLAA activity. Subjects at risk for a disease that is caused or contributed to by aberrant BLAA expression or activity can be identified by, for example, any or a combination of diagnostic or prognostic assays as described herein. Administration of a prophylactic agent can occur prior to the manifestation of symptoms characteristic of the BLAA aberrancy, such that a disease or disorder is prevented or, alternatively, delayed in its progression. Depending on the type of BLAA aberrancy, for example, a BLAA agonist or BLAA antagonist agent can be used for treating the subject. The appropriate agent can be determined based on screening assays described herein. The prophylactic methods of the present invention are further discussed in the following subsections.

Therapeutic Methods

Another aspect of the invention pertains to methods of modulating BLAA expression or activity for therapeutic purposes. The modulatory method of the invention involves contacting a cell with an agent that modulates one or more of the activities of BLAA polypeptide activity associated with the cell. An agent that modulates BLAA polypeptide activity can be an agent as described herein, such as a nucleic acid or a protein, a naturally-occurring cognate ligand of a BLAA polypeptide, a peptide, a BLAA peptidomimetic, or other small molecule. In one embodiment, the agent stimulates one or more BLAA polypeptide activity. Examples of such stimulatory agents include active BLAA polypeptide and a nucleic acid molecule encoding BLAA that has been introduced into the cell. In another embodiment, the agent inhibits one or more BLAA polypeptide activity. Examples of such inhibitory agents include antisense BLAA nucleic acid molecules and anti-BLAA antibodies. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a BLAA polypeptide or nucleic acid molecule. In one embodiment, the method involves administering an agent (e.g., an agent identified by a screening assay described herein), or combination of agents that modulates (e.g., upregulates or downregulates) BLAA expression or activity. In another embodiment, the method involves administering a BLAA polypeptide or nucleic acid molecule as therapy to compensate for reduced or aberrant BLAA expression or activity.

Stimulation of BLAA activity is desirable in situations in which BLAA is abnormally downregulated and/or in which increased BLAA activity is likely to have a beneficial effect. One example of such a situation is where a subject has a disorder characterized by aberrant cell proliferation and/or differentiation (e.g., cancer). Another example of such a situation is where the subject has an immune response-associated disorder (e.g., autoimmune disorders, infectious diseases, and complications associated with transplantation).

In one embodiment, this invention involves a method of treating a pathological state in a mammal comprising administering a therapeutic amount of a polypeptide that is at least 95% identical to a polypeptide with an amino acid sequence of SEQ ID NO: 2 or SEQ ID NO: 4, or a biologically active fragment thereof. An alternative embodiment involves administering to a subject an antibody that selectively binds to a BLAA polypeptide, and fragments, homologs, analogs, and derivatives thereof.

Determination of the Biological Effect of the Therapeutic

In various embodiments of the present invention, suitable in vitro or in vivo assays are utilized to determine the effect of a specific therapeutic and whether its administration is indicated for treatment of the affected tissue.

In various specific embodiments, in vitro assays may be performed with representative cells of the type(s) involved in the patient's disorder, to determine if a given therapeutic exerts the desired effect upon the cell type(s). Compounds for use in therapy may be tested in suitable animal model systems including, but not limited to rats, mice, chicken, cows, monkeys, rabbits, and the like, prior to testing in human subjects. Similarly, for in vivo testing, any of the animal model system known in the art may be used prior to administration to human subjects.

Malignancies

An aforementioned BLAA polypeptide may be involved in the regulation of cell proliferation. Accordingly, therapeutics of the present invention may be useful in the therapeutic or prophylactic treatment of diseases or disorders that are associated with cell hyperproliferation and/or loss of control of cell proliferation (e.g., cancers, malignancies and tumors). For a review of such hyperproliferation disorders, see e.g., Fishman, et al., 1985. *MEDICINE*, 2nd ed., J. B. Lippincott Co., Philadelphia, Pa.

Therapeutics of the present invention may be assayed by any method known within the art for determining efficacy in treating or preventing malignancies and related disorders. Such assays include, but are not limited to, in vitro assays utilizing transformed cells or cells derived from the patient's tumor, as well as in vivo assays using animal models of cancer or malignancies. Potentially effective therapeutics are those that, for example, inhibit the proliferation of tumor-derived or transformed cells in culture or cause a regression of tumors in animal models, in comparison to the controls.

In the practice of the present invention, once a malignancy or cancer has been shown to be amenable to treatment by modulating (i.e., inhibiting, antagonizing, or agonizing) activity, that cancer or malignancy may subsequently be treated or prevented by the administration of a therapeutic that serves to modulate polypeptide function.

Disorders Related to Organ Transplantation

BLAA has been implicated in disorders related to organ transplantation, in particular, but not limited to, organ rejection. Therapeutics of the invention, particularly those that modulate (or supply) activity, may be effective in treating or preventing diseases or disorders related to organ transplantation. Therapeutics of the invention (particularly therapeutics that modulate the levels or activity of an aforementioned protein) can be assayed by any method known in the art for efficacy in treating or preventing such diseases and disorders related to organ transplantation. Such assays include in vitro assays for using cell culture models as described below, or in vivo assays using animal models of diseases and disorders related to organ transplantation, see e.g., below. Potentially effective therapeutics, for example, but not by way of limitation, reduce immune rejection responses in animal models in comparison to controls.

Accordingly, once diseases and disorders related to organ transplantation are shown to be amenable to treatment by modulation of activity, such diseases or disorders can be treated or prevented by administration of a therapeutic that modulates activity.

T lymphocyte Growth and Activation Cell Proliferation/Differentiation Activity

The BLAA polypeptide disclosed in the instant invention is a new B7 family member. B7 family members, such as B7-1 and B7-2, are members of the immunoglobulin superfamily and bind to activated T lymphocytes and provide regulatory signals for T lymphocyte cell growth than activation.

Immune Stimulating or Suppressing Activity

A BLAA polypeptide of the present invention may also exhibit immune stimulating or immune suppressing activity, including without limitation the activities for which assays are described herein. A protein may be useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies may be genetic or be caused by viral (e.g., HIV) as well as bacterial or fungal infections, or may result from autoimmune disorders. More specifically, infectious diseases causes by vital, bacterial, fungal or other infection may be treatable using a polypeptide of the present invention, including infections by HIV, hepatitis viruses, herpesviruses, mycobacteria, Leishmania species, malaria species, and various fungal infections such as candidiasis. Of course, in this regard, a polypeptide of the present invention may also be useful where a boost to the immune system generally may be desirable, i.e., in the treatment of cancer.

Autoimmune disorders which may be treated using a polypeptide of the present invention include, for example, connective tissue disease, multiple sclerosis, systemic lupus erythematosus, rheumatoid arthritis, autoimmune pulmonary inflammation, Guillain-Barre syndrome, autoimmune thyroiditis, insulin dependent diabetes mellitus, myasthenia gravis, graft-versus-host disease and autoimmune inflammatory eye disease. Such a polypeptide of the present invention may also to be useful in the treatment of allergic reactions and conditions, such as asthma (particularly allergic asthma) or other respiratory problems. Other conditions, in which immune suppression is desired (including, for example, organ transplantation), may also be treatable using a polypeptide of the present invention.

Using the polypeptide of the invention to modulate immune responses in a number of ways. Down regulation may be in the form of inhibiting or blocking an immune response already in progress or may involve preventing the induction of an immune response. The functions of activated T cells may be inhibited by suppressing T cell responses or by inducing specific tolerance in T cells, or both. Immunosuppression of T cell responses is generally an active, non-antigen-specific, process which requires continuous exposure of the T cells to the suppressive agent. Tolerance, which involves inducing non-responsiveness or energy in T cells, is distinguishable from immunosuppression in that it is generally antigen-specific and persists after exposure to the tolerizing agent has ceased. Operationally, tolerance can be demonstrated by the lack of a T cell response upon re-exposure to specific antigen in the absence of the tolerizing agent.

Down regulating or preventing one or more antigen functions (including without limitation B lymphocyte antigen functions (such as, for example, B7)), e.g., preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. The administration of a molecule which inhibits or blocks interaction of a B7 lymphocyte antigen with its natural ligand(s) on immune cells (such as a soluble, monomeric form of a peptide having B7-2 activity alone or in conjunction with a monomeric form of a peptide having an activity of another B lymphocyte antigen (e.g., B7-1, B7-3) or blocking antibody), prior to transplantation can lead to the binding of the molecule to the natural ligand(s) on the immune cells without transmitting the corresponding costimulatory signal. Blocking B lymphocyte antigen function in this matter prevents cytokine synthesis by immune cells, such as T cells, and thus acts as an immunosuppressant. Moreover, the lack of costimulation may also be sufficient to energize the T cells, thereby inducing tolerance in a subject. Induction of long-term tolerance by B lymphocyte antigen-blocking reagents may avoid the necessity of repeated administration of these blocking reagents. To achieve sufficient immunosuppression or tolerance in a subject, it may also be necessary to block the function of B lymphocyte antigens.

The efficacy of particular blocking reagents in preventing organ transplant rejection or GVHD can be assessed using animal models that are predictive of efficacy in humans. Examples of appropriate systems which can be used include allogeneic cardiac grafts in rats and xenogeneic pancreatic islet cell grafts in mice, both of which have been used to examine the immunosuppressive effects of CTLA4Ig fusion proteins in vivo as described in Lenschow et al., Science 257:789–792 (1992) and Turka et al., *Proc Natl Acad Sci USA*, 89:11102–11105 (1992). In addition, murine models of GVHD (see Paul ed., *FUNDAMENTAL IMMUNOLOGY*, Raven Press, New York, 1989, pp. 846–847) can be used to determine the effect of blocking B lymphocyte antigen function in vivo on the development of that disease.

Blocking antigen function may also be therapeutically useful for treating autoimmune diseases. Many autoimmune disorders are the result of inappropriate activation of T cells that are reactive against self tissue and which promote the production of cytokines and auto-antibodies involved in the pathology of the diseases. Preventing the activation of autoreactive T cells may reduce or eliminate disease symptoms. Administration of reagents which block costimulation of T cells by disrupting receptor:ligand interactions of B lymphocyte antigens can be used to inhibit T cell activation and prevent production of auto-antibodies or T cell-derived cytokines which may be involved in the disease process. Additionally, blocking reagents may induce antigen-specific tolerance of autoreactive T cells which could lead to long-term relief from the disease. The efficacy of blocking reagents in preventing or alleviating autoimmune disorders can be determined using a number of well-characterized animal models of human autoimmune diseases. Examples include murine experimental autoimmune encephalitis, systemic lupus erythematosis in MRL/1pr/1pr mice or NZB hybrid mice, murine autoimmune collagen arthritis, diabetes mellitus in NOD mice and BB rats, and murine experimental myasthenia gravis (see Paul ed., *FUNDAMENTAL IMMUNOLOGY*, Raven Press, New York, 1989, pp. 840–856).

Upregulation of an antigen function (preferably a B lymphocyte antigen function), as a means of up regulating immune responses, may also be useful in therapy. Upregulation of immune responses may be in the form of enhancing an existing immune response or eliciting an initial immune response. For example, enhancing an immune response through stimulating B lymphocyte antigen function may be useful in cases of viral infection. In addition, systemic vital diseases such as influenza, the common cold, and encephalitis might be alleviated by the administration of stimulatory forms of B lymphocyte antigens systemically.

Alternatively, anti-viral immune responses may be enhanced in an infected patient by removing T cells from the patient, costimulating the T cells in vitro with viral antigen-pulsed APCs either expressing a peptide of the present invention or together with a stimulatory form of a soluble peptide of the present invention and reintroducing the in vitro activated T cells into the patient. Another method of enhancing anti-vital immune responses would be to isolate infected cells from a patient, transfect them with a nucleic acid encoding a protein of the present invention as described herein such that the cells express all or a portion of the protein on their surface, and reintroduce the transfected cells into the patient. The infected cells would now be capable of delivering a costimulatory signal to, and thereby activate, T cells in vivo.

In another application, up regulation or enhancement of antigen function (preferably B lymphocyte antigen function) may be useful in the induction of tumor immunity. Tumor cells (e.g., sarcoma, melanoma, lymphoma, leukemia, neuroblastoma, carcinoma) transfected with a nucleic acid encoding at least one peptide of the present invention can be administered to a subject to overcome tumor-specific tolerance in the subject. If desired, the tumor cell can be transfected to express a combination of peptides. For example, tumor cells obtained from a patient can be transfected ex vivo with an expression vector directing the expression of a peptide having B7-2-like activity alone, or in conjunction with a peptide having B7-1-like activity and/or B7-3-like activity. The transfected tumor cells are returned to the patient to result in expression of the peptides on the surface of the transfected cell. Alternatively, gene therapy techniques can be used to target a tumor cell for transfection in vivo.

The presence of the peptide of the present invention having the activity of a B lymphocyte antigen(s) on the surface of the tumor cell provides the necessary costimulation signal to T cells to induce a T cell mediated immune response against the transfected tumor cells. In addition, tumor cells which lack MHC class I or MHC class II molecules, or which fail to reexpress sufficient amounts of MHC class I or MHC class II molecules, can be transfected with nucleic acid encoding all or a portion of (e.g., a cytoplasmic-domain truncated portion) of an MHC class I $\alpha$ chain protein and $\beta_2$ microglobulin protein or an MHC class II a chain protein and an MHC class II $\beta$ chain protein to thereby express MHC class I or MHC class II proteins on the cell surface. Expression of the appropriate class I or class II MHC in conjunction with a peptide having the activity of a B lymphocyte antigen (e.g., B7-1, B7-2, B7-3) induces a T cell mediated immune response against the transfected tumor cell. Optionally, a gene encoding an antisense construct which blocks expression of an MHC class II associated protein, such as the invariant chain, can also be cotransfected with a DNA encoding a peptide having the activity of a B lymphocyte antigen to promote presentation of tumor associated antigens and induce tumor specific immunity. Thus, the induction of a T cell mediated immune response in a human subject may be sufficient to overcome tumor-specific tolerance in the subject.

The activity of a polypeptide of the invention may, among other means, be measured by the following methods: Suitable assays for thymocyte or splenocyte cytotoxicity include, without limitation, those described In: *CURRENT PROTOCOLS IN IMMUNOLOGY*. Coligan et al., eds. Greene Publishing Associates and Wiley-Interscience (Chapter 3, Chapter 7); Herrmann et al., *Proc Natl Acad Sci USA* 78:2488–2492, 1981; Herrmann et al., *J Immunol* 128:1968–1974, 1982; Handa et al., *J Immunol* 135:1564–1572, 1985; Takai et al., *J Immunol* 137:3494–3500, 1986; Takai et al.,*J Immunol* 140:508–512, 1988; Herrmann et al., *Proc Natl Acad Sci USA* 78:2488–2492, 1981; Herrmann et al., *J Immunol* 128:1968–1974, 1982; Handa et al., *J Immunol* 135:1564–1572, 1985; Takai et al., *J Immunol* 137:3494–3500, 1986; Bowman et al., *J Virology* 61:1992–1998; Takai et al, *J Immunol* 140:508–512, 1988; Bertagnolli et al, *Cell Immunol* 133:327–341, 1991; Brown et al., *J Immunol* 153:3079–3092, 1994.

Assays for T-cell-dependent immunoglobulin responses and isotype switching (which will identify, among others, proteins that modulate T-cell dependent antibody responses and that affect Th1/Th2 profiles) include, without limitation, those described in: Maliszewski, *J Immunol* 144:3028–3033, 1990; and Mond and Brunswick In: *CURRENT PROTOCOLS IN IMMUNOLOGY*. Coligan et al., (eds.) Vol 1 pp. 3.8.1–3.8.16, John Wiley and Sons, Toronto 1994.

Mixed lymphocyte reaction (MLR) assays (which will identify, among others, proteins that generate predominantly Th1 and CTL responses) include, without limitation, those described In: *CURRENT PROTOCOLS IN IMMUNOLOGY*. Coligan et al., eds. Greene Publishing Associates and Wiley-Interscience (Chapter 3, Chapter 7); Takai et al., *J Immunol* 137:3494–3500, 1986; Takai et al.,*J Immunol* 140:508–512, 1988; Bertagnolli et al., *J Immunol* 149:3778–3783, 1992.

Dendritic cell-dependent assays (which will identify, among others, proteins expressed by dendritic cells that activate naive T-cells) include, without limitation, those described in: Guery et al., *J Immunol* 134:536–544, 1995; Inaba et al.,*J Exp Med* 173:549–559, 1991; Macatonia et al., *J Immunol* 154:5071–5079, 1995; Porgador et al.,*J Exp Med* 182:255–260, 1995; Nair et al.,*J Virol* 67:4062–4069, 1993; Huang et al., *Science* 264:961–965, 1994; Macatonia et al., *J Exp Med* 169:1255–1264, 1989; Bhardwaj et al., *J Clin Investig* 94:797–807, 1994; and Inaba et al., *J Exp Med* 172:631–640, 1990.

Assays for lymphocyte survival/apoptosis (which will identify, among others, proteins that prevent apoptosis after superantigen induction and proteins that regulate lymphocyte homeostasis) include, without limitation, those described in: Darzynkiewicz et al., *Cytometry* 13:795–808, 1992; Gorczyca et al., *Leukemia* 7:659–670, 1993; Gorczyca et al., *Cancer Res* 53:1945–1951, 1993; Itoh et al., *Cell* 66:233–243, 1991; Zacharchuk,*J Immunol* 145:4037–4045, 1990; Zamai et al., *Cytometry* 14:891–897, 1993; Gorczyca et al., *Internat J Oncol* 1:639–648, 1992.

Assays for proteins that influence early steps of T-cell commitment and development include, without limitation, those described in: Antica et al., *Blood* 84:111–117, 1994; Fine et al., *Cell Immunol* 155: 111–122, 1994; Galy et al., *Blood* 85:2770–2778, 1995; Toki et al., *Proc Nat Acad Sci USA* 88:7548–7551, 1991.

Other Activities

A polypeptide of the invention may also exhibit one or more of the following additional activities or effects: inhibiting the growth, infection or function of, or killing, infectious agents, including, without limitation, bacteria, viruses, fungi and other parasites; effecting (suppressing or enhancing) bodily characteristics, including, without limitation, height, weight, hair color, eye color, skin, fat to lean ratio or other tissue pigmentation, or organ or body part size or shape (such as, for example, breast augmentation or diminution, change in bone form or shape); effecting biorhythms or circadian cycles or rhythms; effecting the fertility of male or female subjects; effecting the metabolism, catabolism, anabolism, processing, utilization, storage or elimination of dietary fat, lipid, protein, carbohydrate, vitamins, minerals, cofactors or other nutritional factors or component(s); effecting behavioral characteristics, including, without limitation, appetite, libido, stress, cognition (including cognitive disorders), depression (including depressive disorders) and violent behaviors; providing analgesic effects or other pain reducing effects; promoting differentiation and growth of embryonic stem cells in lineages other than hematopoietic lineages; hormonal or endocrine activity; in the case of enzymes, correcting deficiencies of the enzyme and treating deficiency-related diseases; treatment of hyperproliferative disorders (such as, for example, psoriasis); immunoglobulin-like activity (such as, for example, the ability to bind antigens or complement); and the ability to act as an antigen in a vaccine composition to raise an immune response against such protein or another material or entity which is cross-reactive with such protein.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

The contents of all references, patents and published patent applications cited throughout this application are hereby incorporated by reference.

EQUIVALENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

We Claim:

1. An isolated nucleic acid molecule encoding a B lymphocyte activation antigen (BLAA), wherein said molecule comprises a nucleotide sequence encoding the polypeptide defined by SEQ ID NO:2 or the full length complement of said nucleic acid molecule.

2. The nucleic acid molecule of claim 1, wherein said molecule hybridizes under stringent conditions to a nucleic acid sequence fully complementary to a nucleic acid molecule comprising the sequence of nucleotides of SEQ ID NO:1, wherein the stringent conditions comprise a high salt buffer comprising 6×SSC, 50 mM Tris-HCl (pH 7.5), 1 mM EDTA, 0.02% PVP, 0.02% Ficoll, 0.02% BSA, and 50 mg/ml denatured salmon sperm DNA at 65° C. followed by one or more washes in 0.2×SSC, 0.01% BSA at 50° C.

3. The nucleic acid molecule of claim 1, wherein said nucleotide sequence encodes a human BLAA.

4. A vector comprising the nucleic acid molecule of claim 1.

5. The vector of claim 4, wherein said vector is an expression vector.

6. The vector of claim 4, further comprising a regulatory element operably linked to said nucleic acid molecule.

7. A method of producing the polypeptide of SEQ ID NO:2, said method comprising culturing a cell comprising the nucleic acid molecule of claim 1 under conditions allowing for expression of a polypeptide encoded by said nucleic acid molecule and recovering said polypeptide.

8. A composition comprising the nucleic acid molecule of claim 1 and a pharmaceutically acceptable carrier.

9. A kit comprising in one or more containers the composition of claim 8.

* * * * *